(12) United States Patent
Dunn et al.

(10) Patent No.: US 10,114,020 B2
(45) Date of Patent: *Oct. 30, 2018

(54) SYSTEM AND DEVICE FOR ANALYZING A FLUIDIC SAMPLE

(71) Applicant: MBio Diagnostics, Inc., Boulder, CO (US)

(72) Inventors: John S. Dunn, Arvada, CO (US);
Jeffrey T. Ives, Arvada, CO (US);
Michael J. Lochhead, Boulder, CO (US); Kurt R. Vogel, Boulder, CO (US); Keagan B. Rowley, Boulder, CO (US)

(73) Assignee: MBio Diagnostics, Inc., Boulder, CO (US)

( * ) Notice: Subject to any disclaimer, the term of this patent is extended or adjusted under 35 U.S.C. 154(b) by 112 days.

This patent is subject to a terminal disclaimer.

(21) Appl. No.: 13/831,809

(22) Filed: Mar. 15, 2013

(65) Prior Publication Data

US 2013/0244313 A1 Sep. 19, 2013

Related U.S. Application Data

(63) Continuation-in-part of application No. PCT/US2011/055844, filed on Oct. 11, 2011.
(Continued)

(51) Int. Cl.
*G01N 33/569* (2006.01)
*G01N 15/14* (2006.01)
(Continued)

(52) U.S. Cl.
CPC .... *G01N 33/56972* (2013.01); *B01L 3/50273* (2013.01); *G01N 15/1456* (2013.01);
(Continued)

(58) Field of Classification Search
CPC ............ B01L 3/50273; B01L 2200/16; B01L 2300/069; B01L 2300/0636;
(Continued)

(56) References Cited

U.S. PATENT DOCUMENTS

| 5,104,619 A | 4/1992 | De Castro et al. |
| 5,348,859 A | 9/1994 | Brunhouse et al. |

(Continued)

FOREIGN PATENT DOCUMENTS

| EP | 1 500 937 A1 | 1/2005 |
| EP | 1 356 420 B1 | 10/2006 |

(Continued)

OTHER PUBLICATIONS

English language translation of JP 2009-121985, translated on Apr. 4, 2016.*

(Continued)

*Primary Examiner* — Michael L Hobbs
*Assistant Examiner* — Liban M Hassan
(74) *Attorney, Agent, or Firm* — Lathrop Gage LLP

(57) ABSTRACT

A device for analyzing an analyte in a sample includes a first substrate, a second substrate, a fluidic channel, an inlet port and an outlet port. Each of the first substrate and the second substrate has an inner surface and an outer surface, the inner surface of the first substrate forming, at least in part, the lower wall of the fluidic channel, and the inner surface of the second substrate forming, at least in part, the upper wall of the fluidic channel. The fluidic channel is connected to the inlet port and the outlet port. The fluidic channel includes a reagent region and a detection region, at least a portion of the reagent region being coated with one or more dried reagents. The device further includes a wicking pad located on the outer surface of the second substrate, the wicking pad being positioned at a pre-determined distance from the outlet port.

23 Claims, 52 Drawing Sheets

Related U.S. Application Data

(60) Provisional application No. 61/391,911, filed on Oct. 11, 2010, provisional application No. 61/732,858, filed on Dec. 3, 2012, provisional application No. 61/719,812, filed on Oct. 29, 2012.

(51) Int. Cl.
  *B01L 3/00* (2006.01)
  *G01N 15/10* (2006.01)
  *G01N 35/00* (2006.01)

(52) U.S. Cl.
  CPC ...... *G01N 15/1484* (2013.01); *B01L 2200/16* (2013.01); *B01L 2300/0636* (2013.01); *B01L 2300/0816* (2013.01); *B01L 2400/0406* (2013.01); *G01N 2015/1006* (2013.01); *G01N 2035/00158* (2013.01)

(58) Field of Classification Search
  CPC ..... B01L 2300/0816; B01L 2300/0819; B01L 2400/0406; G01N 33/56972; G01N 15/1484; G01N 15/1456; G01N 2035/00158; G01N 2015/1006
  USPC .............................. 435/287.2, 288.7
  See application file for complete search history.

(56) References Cited

U.S. PATENT DOCUMENTS

| | | | |
|---|---|---|---|
| 5,426,029 A | 6/1995 | Rittershaus et al. | |
| 5,547,849 A | 8/1996 | Baer et al. | |
| 5,585,246 A | 12/1996 | Dubrow et al. | |
| 5,674,457 A | 10/1997 | Williamsson et al. | |
| 5,677,196 A | 10/1997 | Herron et al. | |
| 5,747,265 A | 5/1998 | Parsons et al. | |
| 5,790,710 A | 8/1998 | Price et al. | |
| 5,891,656 A | 4/1999 | Zarling et al. | |
| 5,922,604 A * | 7/1999 | Stapleton et al. | 436/46 |
| 5,932,428 A | 8/1999 | Dubrow et al. | |
| 5,962,238 A | 10/1999 | Sizto et al. | |
| 5,972,721 A | 10/1999 | Bruno et al. | |
| 6,008,052 A | 12/1999 | Davis et al. | |
| 6,143,247 A | 11/2000 | Sheppard, Jr. et al. | |
| 6,238,874 B1 | 5/2001 | Jarnagin et al. | |
| 6,468,807 B1 | 10/2002 | Svensson et al. | |
| 6,495,104 B1 | 12/2002 | Unno et al. | |
| 6,890,426 B2 | 5/2005 | Terstappen et al. | |
| 6,991,939 B2 | 1/2006 | Walt et al. | |
| 7,067,263 B2 | 6/2006 | Parce et al. | |
| 7,190,832 B2 | 3/2007 | Frost et al. | |
| 7,248,361 B2 | 7/2007 | Kiesel et al. | |
| 7,268,868 B2 | 9/2007 | Kiesel et al. | |
| 7,282,180 B2 | 10/2007 | Tibbe et al. | |
| 7,314,763 B2 | 1/2008 | Song et al. | |
| 7,386,199 B2 | 6/2008 | Schmidt et al. | |
| 7,456,953 B2 | 11/2008 | Schmidt et al. | |
| 7,522,811 B2 | 4/2009 | Schmidt et al. | |
| 7,529,438 B2 | 5/2009 | Schmidt et al. | |
| 7,629,165 B2 | 12/2009 | Wyatt et al. | |
| 7,738,094 B2 | 6/2010 | Goldberg | |
| 7,764,821 B2 | 7/2010 | Coumans et al. | |
| 7,781,226 B2 | 8/2010 | McDevitt et al. | |
| 7,828,968 B2 | 11/2010 | Tibbe et al. | |
| 7,927,561 B2 | 4/2011 | Kirakossian et al. | |
| 7,943,397 B2 | 5/2011 | Tibbe et al. | |
| 8,009,894 B2 | 8/2011 | Lindberg et al. | |
| 8,040,494 B2 | 10/2011 | Ermantraut et al. | |
| 8,092,758 B2 | 1/2012 | Lindberg et al. | |
| 8,110,160 B2 | 2/2012 | Assmann et al. | |
| 8,224,058 B2 | 7/2012 | Lindberg et al. | |
| 8,248,597 B2 | 8/2012 | Goldberg | |
| 8,300,933 B2 | 10/2012 | Moll et al. | |
| 8,300,993 B2 | 10/2012 | Moll et al. | |
| 8,586,347 B2 | 11/2013 | Lochhead et al. | |
| 8,753,894 B2 | 6/2014 | Tondra | |
| 2001/0039057 A1* | 11/2001 | Douglas et al. | 436/169 |
| 2002/0094147 A1 | 7/2002 | Herron et al. | |
| 2002/0186874 A1 | 12/2002 | Price et al. | |
| 2003/0096324 A1 | 5/2003 | Matveev et al. | |
| 2003/0124623 A1* | 7/2003 | Yager et al. | 435/7.5 |
| 2004/0018523 A1* | 1/2004 | Hawkins | 435/6 |
| 2004/0161143 A1 | 8/2004 | Dietz et al. | |
| 2004/0248213 A1 | 12/2004 | Karlsson et al. | |
| 2004/0265171 A1* | 12/2004 | Pugia et al. | 422/58 |
| 2005/0016844 A1* | 1/2005 | Burke | G01N 33/558 204/403.01 |
| 2005/0048597 A1 | 3/2005 | Smith et al. | |
| 2005/0048599 A1 | 3/2005 | Goldberg et al. | |
| 2005/0088648 A1 | 4/2005 | Grace et al. | |
| 2005/0249641 A1 | 11/2005 | Blankenstein et al. | |
| 2006/0024756 A1 | 2/2006 | Tibbe et al. | |
| 2006/0063274 A1 | 3/2006 | Schremp | |
| 2006/0216195 A1* | 9/2006 | Blankenstein | B01L 3/50273 422/400 |
| 2006/0257992 A1 | 11/2006 | McDevitt et al. | |
| 2006/0292559 A1 | 12/2006 | Reddy et al. | |
| 2007/0039835 A1* | 2/2007 | Rossier | B01L 3/50273 205/792 |
| 2007/0190525 A1 | 8/2007 | Gu et al. | |
| 2007/0202538 A1 | 8/2007 | Glezer et al. | |
| 2007/0231851 A1 | 10/2007 | Toner et al. | |
| 2007/0297949 A1 | 12/2007 | Wu et al. | |
| 2008/0050830 A1 | 2/2008 | Floriano et al. | |
| 2008/0176209 A1* | 7/2008 | Muller | A01N 1/00 435/2 |
| 2008/0176253 A1 | 7/2008 | Christodoulides et al. | |
| 2008/0200342 A1* | 8/2008 | Rao et al. | 506/9 |
| 2009/0014360 A1 | 1/2009 | Toner et al. | |
| 2009/0038939 A1 | 2/2009 | Popovich | |
| 2009/0059222 A1* | 3/2009 | Tan | B01L 3/502753 356/318 |
| 2009/0060303 A1 | 3/2009 | Douglass et al. | |
| 2009/0079963 A1 | 3/2009 | Ermantraut et al. | |
| 2009/0203126 A1* | 8/2009 | Hung et al. | 435/325 |
| 2009/0215072 A1 | 8/2009 | McDevitt et al. | |
| 2009/0286692 A1 | 11/2009 | Wainwright et al. | |
| 2009/0305231 A1 | 12/2009 | Weidemaier et al. | |
| 2010/0056387 A1 | 3/2010 | Schulz et al. | |
| 2010/0159611 A1 | 6/2010 | Song et al. | |
| 2010/0179068 A1 | 7/2010 | Kaiser et al. | |
| 2010/0220318 A1 | 9/2010 | Moll et al. | |
| 2010/0261197 A1 | 10/2010 | Goldberg et al. | |
| 2010/0291588 A1 | 11/2010 | McDevitt et al. | |
| 2011/0044527 A1 | 2/2011 | Tibbe et al. | |
| 2011/0049388 A1 | 3/2011 | Delaney et al. | |
| 2011/0052037 A1 | 3/2011 | Coumans et al. | |
| 2011/0065209 A1 | 3/2011 | Heil et al. | |
| 2011/0111425 A1 | 5/2011 | Rylatt | |
| 2011/0256549 A1 | 10/2011 | Gaylord et al. | |
| 2012/0015392 A1 | 1/2012 | Guo | |
| 2012/0058464 A1 | 3/2012 | Ermantraut et al. | |
| 2012/0071342 A1 | 3/2012 | Lochhead et al. | |
| 2012/0088230 A1 | 4/2012 | Givens et al. | |
| 2012/0122084 A1 | 5/2012 | Wagner et al. | |
| 2013/0098775 A1 | 4/2013 | Pei et al. | |
| 2014/0004539 A1 | 1/2014 | Simon et al. | |

FOREIGN PATENT DOCUMENTS

| | | |
|---|---|---|
| EP | 1 801 564 A1 | 6/2007 |
| EP | 2 169 387 A2 | 3/2010 |
| EP | 2 090 889 B1 | 1/2012 |
| EP | 2 559 488 A1 | 2/2013 |
| JP | 2007-171182 A | 7/2007 |
| JP | 2009121985 A * | 6/2009 |
| WO | 2002/008762 A1 | 1/2002 |
| WO | 2008/092075 A2 | 7/2008 |
| WO | 2009/112030 A1 | 9/2009 |

(56) References Cited

FOREIGN PATENT DOCUMENTS

| WO | 2011/026030 A1 | 3/2011 |
|---|---|---|
| WO | 2011/143075 A2 | 11/2011 |
| WO | WO 2012/048096 | 4/2012 |

OTHER PUBLICATIONS

PCT/US2011/055844 International Search Report and Written Opinion dated Jun. 12, 2012, 19 pages.
PCT/US2011/055844 Response to Written Opinion filed Sep. 12, 2012, 12 pages.
PCT/US2011/055844 Written Opinion of the International Preliminary Examining Authority dated Nov. 26, 2012, 5 pages.
PCT/US2011/055844 International Preliminary Report on Patentability dated Feb. 27, 2013, 23 pages.
Notice of Allowance corresponding to U.S. Appl. No. 13/878,611, dated Jan. 15, 2016, 9 pages.
Beck et al. (2012) "On-Chip Sample Preparation by Controlled Release of Antibodies for Simple CD4 Counting," Lab Chip. 12:167-173.
Cheng et al. (2007) "A Microchip Approach for Practical Label-Free CD4+ T-Cell Counting of HIV-Infected Subjects in Resource-Poor Settings," Acquir Immune Defic Syndr. 45(3):257-261.
Cheng et al. (2007) "A Microfluidic Device for Partial Label-Free CD4+ T-Cell Counting of HIV-Infected Subjects," Lab Chip. 7:170-178.
Cheng et al. (2007) "Cell detection and counting through cell lysate impedance spectroscopy in microfluidic devices," Lab Chip. 7:746-755.
Cheng et al. (2009) "Enhancing the Performance of a Point-Of-Care CD4+ T-Cell Counting Microchip Through Monocyte Depletion for HIV/AIDS Diagnostics," Lab Chip. 9:1357-1364.
Erickson et al. (2004) "Integrated Microfluidic Devices," Analytics Chimica Acta. 507:11-26.
Glynn et al. (Jul. 21, 2013) "CD4 Counting Technologies for HIV Therapy Monitoring in Resource-Poor Settings—State-Of-The-Art and Emerging Microtechnologies," Lab Chip. 13(14):2731-2748.
Gupta et al. (2003) "Whole-Blood Agglutination Assay for On-Site Detection of Human Immunodeficiency Virus Infection," Journal of Clinical Microbiology. 41(7):2814-2821.
Hirschkorn et al. (1999) "Automated enumeration of CD4 and CD8 lymphocyte counts: a multisite evaluation of the IMAGN 2000 microvolume fluorimeter," Laboratory Hematology. 5:1-xx. pp. 1-6.
Hosokawa et al. (2012) "Leukocyte Counting From a Small Amount of Whole Blood Using a Size-Controlled Microcavity Array," Biotechnology and Bioengineering. 109(8):2017-2024.
Ji et al. (2004) "Real-Time Detection of Bacterial Contamination in Dynamic Aqueous Environments Using Optical Sensors," Anal. Chem. 76(5):1411-1418.
Jokerst et al. (2008) "Integration of Semiconductor Quantum Dots Into Nano-Bio-Chip Systems for Enumeration of CD4+ T-Cell Counts at the Point-Of-Need," Lab Chip. 8:2079-2090.
Jokerst et al. (2010) "Programmable Nano-Bio-Chip Sensors: Analytical Meets Clinical," Analytical Chemistry. 82(5):1571-1579.
Kachouie et al. (2009) "Arraycount, an algorithm for automatic cell counting in microwell arrays," BioTechniques. 47(3):x-xvi.
Kim et al. (2012) "A quartz nanopillar hemocytometer for high-yield separation and counting of CD4+ T lymphocytes," Nanoscale. 4:2500-2507.
Lab Now (Aug. 3, 2008) "A Comparison of the LabNow CD4 System to Flow Cytometry in Determining Absolute CD4 Counts, Total Lymphocyte Counts, and CD4 Percent in Whole Blood," pp. 1-5.
Li et al. (2007) "CD4+ Lymphocytes Enumeration by an Easey-To-Use Single Platform Image Cytometer for HIV Monitoring in Resource-Constrained Settings," Cytom. B. Clin. Cytom. 72(5):397-407.
Li et al. (2009) "CD4 and CD8 Enumeration for HIV Monitoring in Resource-Constrained Settings," Cytom. B. Clin. Cytom. 76:118-126.
Li et al. (2010) "Clinical Evaluation of a Simple Image Cytometer for CD4 Enumeration on HIV-Infected Patients," Cytom. B Clin. Cytom. 78:31-36.
Lochhead et al. (2010) "Low-cost fluorescence microscopy for point-of-care cell imaging," Proc. of SPIE. 7572:75720B. pp. 1-6.
Lochhead et al. (2011) "Rapid Multiplexed Immunoassay for Simultaneous Serodiagnosis of HIV-1 and Coinfections," J. Clin. Microbiol. Oct. 49(10):3584-9350.
Meijering et al. (2006) "Biological Image Analysis Primer," Biomedical Imaging Group, Applied Optical Imaging Center. Erasmus MC—University Medical Center. Rotterdam, The Netherlands. pp. 1-37.
Moon et al. (2009) "Integrating Microfluidics and Lensless Imaging for Point-of-Care Testing," Biosens Bioelectron. 24(11):3208-3214.
Moon et al. (2011) "Enumeration of CD4+ T-Cell Using a Portable Microchip Count Platform in Tanzanian HIV-Infected Patients," PLoS One. 6(7):e21409. pp. 1-8.
Ozcan et al. (2008) "Ultra wide-field lens-free monitoring of cells on-chip," Lab Chip. 8:98-106.
Rodriquez et al. (2005) "A Microchip CD4 Counting Method for HIV Monitoring in Resource-Poor Settings," PLoS Medicine. 2(7):e182. pp. 663-672.
Sahoo et al. (1988) "A Survey of Thresholding Techniques," Computer Vision, Graphics, and Image Processing. 41:233-260.
Schembri et al. (1992) "Portable Simultaneous Multiple Analyte Whole-Blood Analyzer for Point-Of-Care Testing," Clinical Chemistry. 38(9):1665-1670.
Schembri et al. (1995) "Centrifugation and Capillarity Integrated Into a Multiple Analyte Whole Blood Analyser," Journal of Automatic Chemistry. 17(3):99-104.
Schmidt et al. (2007) "Fluorescence spectrometer-on-a-fluidic-chip," Lab Chip. 7:626-629.
Schmidt et al. (2008) "Optofluidic Waveguides: I. Concepts and Implementations," In; Microfluidics and Nanofluidics. vol. 4. Springer-Verlag. pp. 3-16.
Singh et al. (2004) "Analysis of Cellular Structure by Light Scattering Measurements in a New Cytometer Design Based on a Liquid-Core Waveguide," In; IEE Proc.-Nanobiotechnol. Feb. 2004. 151(1):10-16.
Vincent (1993) "Morphological Grayscale Reconstruction in Image Analysis: Applications and Efficient Algorithms," IEEE Transactions on Image Processing. 2(2):176-201.
Vincent et al. (1991) "Watersheds in Digital Spaces: An Efficient Algorithm Based on Immersion Simulations," IEEE Transactions on Pattern Analysis and Machine Intelligence. 13(6):583-598.
Wang et al. (2010) "Microfluidic CD4+ T-Cell Counting Device Using Chemiluminescence-Based Detection," Anal. Chem. 82:36-40.
Watkins et al. (2011) "A Microfabricated Electrical Differential Counter for the Selective Enumerations of CD4+ T-Lymphocytes," Lab Chip. 11(8): 1437-1447.
Yin et al. (2004) "Integrated optical waveguides with liquid cores," Applied Physics Letters. 85(16):3477-3479.
Ymeti et al. (2007) "A Single Platform Image Cytometer Fro Resource-Poor Settings to Monitor Disease Progression in HIV Infection," Cytom. A. 71:132-142.
Zhu et al. (2008) "A microdevice for multiplexed detection of T-cell-secreted cytokines," Lab Chip. 8:2197-2205.
Zhu et al. (2008) "A miniature cytometry plafform for capture and characterization of T-lymphocytes from human blood," Analytica Chimica Acta. 608:186-196.
International Preliminary Report on Patentability corresponding to International Patent Application No. PCT/US2011/055817, dated Jan. 15, 2013, 27 pgs.
International Search Report with Written Opinion corresponding to International Patent Application No. PCT/US2013/031811, dated Jul. 22, 2013, 11 pgs.
Office Action corresponding to U.S. Appl. No. 13/831,757, dated Sep. 14, 2016, 21 pgs.

(56) References Cited

OTHER PUBLICATIONS

Office Action corresponding to U.S. Appl. No. 13/831,757, dated Sep. 15, 2015, 13 pgs.
Partial European Search Report corresponding to European Patent Application No. 13850163.0, dated May 24, 2016, 6 pgs.
Response to Office Action corresponding to U.S. Appl. No. 13/831,757, filed Nov. 16, 2015, 23 pgs.
Supplementary European Search Report corresponding to European Patent Application No. 13850163.0, dated Oct. 4, 2016, 12 pgs.

\* cited by examiner

K

| 0 | 0 | 0 | 1 | 1 | 1 | 1 | 1 | 0 | 0 | 0 |
|---|---|---|---|---|---|---|---|---|---|---|
| 0 | 0 | 1 | 1 | 1 | 1 | 1 | 1 | 1 | 0 | 0 |
| 0 | 1 | 1 | 1 | 1 | 1 | 1 | 1 | 1 | 1 | 0 |
| 1 | 1 | 1 | 1 | -1 | -1 | -1 | 1 | 1 | 1 | 1 |
| 1 | 1 | 1 | -1 | -3 | -5 | -3 | -1 | 1 | 1 | 1 |
| 1 | 1 | 1 | -1 | -5 | -7 | -5 | -1 | 1 | 1 | 1 |
| 1 | 1 | 1 | -1 | -3 | -5 | -3 | -1 | 1 | 1 | 1 |
| 1 | 1 | 1 | 1 | -1 | -1 | -1 | 1 | 1 | 1 | 1 |
| 0 | 1 | 1 | 1 | 1 | 1 | 1 | 1 | 1 | 1 | 0 |
| 0 | 0 | 1 | 1 | 1 | 1 | 1 | 1 | 1 | 0 | 0 |
| 0 | 0 | 0 | 1 | 1 | 1 | 1 | 1 | 0 | 0 | 0 |

| 0 | 0 | 0 | .04 | .04 | .04 | .04 | .04 | 0 | 0 | 0 |
|---|---|---|---|---|---|---|---|---|---|---|
| 0 | 0 | .04 | .04 | .04 | .04 | .04 | .04 | .04 | 0 | 0 |
| 0 | .04 | .04 | .04 | .04 | .04 | .04 | .04 | .04 | .04 | 0 |
| .04 | .04 | .04 | .04 | -.04 | -.04 | -.04 | .04 | .04 | .04 | .04 |
| .04 | .04 | .04 | -.04 | -.12 | -.2 | -.12 | -.04 | .04 | .04 | .04 |
| .04 | .04 | .04 | -.04 | -.2 | -.28 | -.2 | -.04 | .04 | .04 | .04 |
| .04 | .04 | .04 | -.04 | -.12 | -.2 | -.12 | -.04 | .04 | .04 | .04 |
| .04 | .04 | .04 | .04 | -.04 | -.04 | -.04 | .04 | .04 | .04 | .04 |
| 0 | .04 | .04 | .04 | .04 | .04 | .04 | .04 | .04 | .04 | 0 |
| 0 | 0 | .04 | .04 | .04 | .04 | .04 | .04 | .04 | 0 | 0 |
| 0 | 0 | 0 | .04 | .04 | .04 | .04 | .04 | 0 | 0 | 0 |

*FIG. 18B*

SYSTEM AND DEVICE FOR ANALYZING A FLUIDIC SAMPLE

CROSS-REFERENCE TO RELATED APPLICATIONS

This application is filed as a continuation-in-part of PCT application PCT/US2011/055844 filed Oct. 11, 2011, which claims priority to U.S. Provisional Patent Application Ser. No. 61/391,911, filed Oct. 11, 2010. This application also claims priority to U.S. Provisional Patent Application Ser. No. 61/719,812, filed Oct. 29, 2012, and U.S. Provisional Patent Application Ser. No. 61/732,858, filed Dec. 3, 2012. The above-identified patent applications are incorporated herein by reference in their entireties.

U.S. GOVERNMENT RIGHTS

This invention was made with Government support under NIH Grant Nos. AI070052 and AI068543, both awarded by the National Institutes of Health. The Government has certain rights in this invention.

BACKGROUND

Identification and enumeration of analytes in complex sample matrices are used in medical, biological, industrial, and environmental applications. Example analytes include particles such as viruses, bacteria, parasites, and specific cell types, typically found in a complex matrix of confounding substances. Sample preparation methods such as filtration, lysis, homogenization and dilution are often required to enable specific particle identification and enumeration in these complex matrices. Particle identification and enumeration are often based on expensive, laboratory-based measurement devices or instrumentation.

A useful example is the identification and enumeration of CD4+ T-helper lymphocytes (CD4 cells) for monitoring and managing conditions in persons with HIV/AIDS. HIV mediated CD4 cell destruction is the central immunologic feature of HIV infection. Thus, the CD4 count is a critical measurement in initial assessment of infection and disease staging, in monitoring antiretroviral therapy and in managing primary and secondary prophylaxis for opportunistic infections. In fact, quantitative T helper cell counts in the range of 0 to 1000 cells per microliter are a critical indicator for initiating and optimizing anti-retroviral treatment and preventing viral drug resistance. Flow cytometry is the current standard-of-care for CD4 cell counting. Unfortunately, flow cytometry is a central lab-based technique; transport, equipment, and operational costs render the technique cost-prohibitive in limited resource settings where HIV prevalence is highest.

SUMMARY

In an embodiment, a particle identification system includes: a cartridge for containing a sample with fluorescently labeled particles; illumination for illuminating a region within the cartridge to stimulate emission from fluorescently labeled particles in the region; imager for generating wavelength-filtered electronic images of the emission within at least one measurement field of the region; and particle identifier for processing the electronic images to determine a superset of particles of interest and determining fluorescently labeled particles within the superset based on properties of the fluorescently labeled particles in the at least one measurement field.

In an embodiment, a method determines fluorescently labeled particles within a sample, by: processing at least one electronic image from at least one focal position within the sample; determining dimmest separation lines between brighter areas in the electronic image; and, for each of the brighter areas, determining local background level based on pixel values of the separation lines forming a perimeter therearound, to determine each of the fluorescently labeled particles.

In an embodiment, a system determines fluorescently labeled particles within a sample and includes: means for processing at least one electronic image from at least one focal position within the sample; means for determining dimmest separation lines between brighter areas in the electronic image; and, for each of the brighter areas, means for determining local background level based on pixel values of the separation lines forming a perimeter therearound, to determine each of the fluorescently labeled particles.

A software product comprising instructions, stored on computer-readable media, wherein the instructions, when executed by a computer, perform steps determining fluorescently labeled particles within a sample, the instructions comprising: instructions for processing at least one electronic image from at least one focal position within the sample; instructions for determining dimmest separation lines between brighter areas in the electronic image; and, for each of the brighter areas, instructions for determining local background level based on pixel values of the separation lines forming a perimeter therearound, to determine each of the fluorescently labeled particles.

In an embodiment, a cartridge is provided for detecting target analytes in a sample. The cartridge includes an inlet port and fluidic channel with a detection region, and a dried reagent coating, disposed in the cartridge, for rehydrating into the sample upon input through the inlet port for the detection region.

In an embodiment, a device for analyzing an analyte in a sample includes a first substrate, a second substrate, a fluidic channel, an inlet port and an outlet port. Each of the first substrate and the second substrate has an inner surface and an outer surface, the inner surface of the first substrate forming, at least in part, the lower wall of the fluidic channel, and the inner surface of the second substrate forming, at least in part, the upper wall of the fluidic channel. The fluidic channel is connected to the inlet port and the outlet port. The fluidic channel includes a reagent region and a detection region, at least a portion of the reagent region being coated with one or more dried reagents. The device further includes a wicking pad located on the outer surface of the second substrate, the wicking pad being positioned at a pre-determined distance from the outlet port.

BRIEF DESCRIPTION OF DRAWINGS

FIG. 18A depicts a kernel that may be convoluted with image data to help identify particles, in an embodiment.

FIG. 18B depicts a normalized version of the kernel of FIG. 18A, that may also be convoluted with image data to help identify particles, in an embodiment.

DETAILED DESCRIPTION OF DRAWINGS

Figure 1:
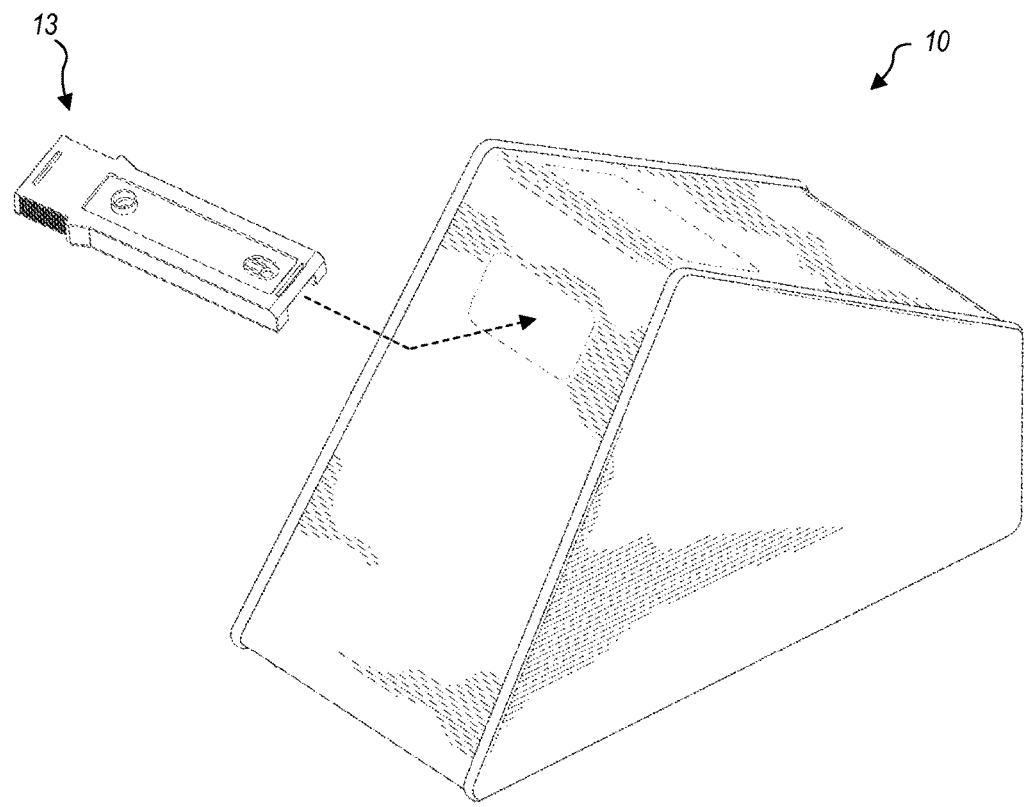
FIG. 1 illustrates a particle identification system that is configured to receive and analyze a sample that is contained within a cartridge, in an embodiment.

The present disclosure may be understood by reference to the following detailed description taken in conjunction with the drawings briefly described below. It is noted that, for purposes of illustrative clarity, certain elements in the drawings may not be drawn to scale. Specific instances of an item may be referred to by use of a numeral in parentheses (e.g., 16(1)) while numerals without parentheses refer to any such item (e.g., 16).

The present disclosure is divided into the following main sections for clarity: System Level Overviews; Particle Counting Methods and Software; Fluidic Features and Methods; and Cartridge Features and Methods.

I. System Level Overviews

The methods described here may be collectively referred to as "static cytometry" using an inventive implementation of an optical system and sample chamber. The term "cytometry" technically refers to the counting or enumeration of cells, particularly blood cells. The term "cytometry" is used generically in this disclosure to refer to the enumeration of any of a number of analytes, particularly particle analytes, described in more detail below. The term "static" implies that the disclosed system and methods do not require that target analytes (for example, cells or particles) move or flow at the time of identification and enumeration. This in contrast to "flow cytometry," a technical method in which target analytes (e.g., cells or particles) are identified and/or enumerated as they move past a detector or sets of detectors. Examples of static cytometry include hemocytometers such as the Petroff-Hauser counting chamber, which is used with a conventional light microscope to enumerate cells in a sample. Cell staining apparatus and fluorescence microscopy instrumentation can be used to perform fluorescence-based static cytometry. The present disclosure provides methods, devices, and instruments for performing static cytometry analysis on a sample.

The methods and systems described herein generally relate to assays that use fluorescence signals to identify and/or enumerate analyte(s) present in a sample. In exemplary applications, target analytes are specifically labeled with fluorophore-conjugated molecules such as an antibody or antibodies (immunostaining). Other molecular recognition elements may be used, including but not limited to aptamers, affibodies, nucleic acids, molecular recognition elements, or biomimetic constructs. Non-specific fluorophores may also be used, including but not limited to stains such as propidium iodide, membrane specific fluorophores, and fluorescent nuclear stains. Generally speaking, electronic images are formed of the fluorescence signals, wherein labeled analytes generate local maxima in the electronic images. Image processing is later utilized to identify the maxima and determine their correspondence to analytes or particles of interest.

In exemplary embodiments, excitable tags are used as detection reagents in assay protocols. Exemplary tags include, but are not limited to, fluorescent organic dyes such as fluorescein, rhodamine, and commercial derivatives such as Alexa dyes (Life Technologies) and DyLight products; fluorescent proteins such as R-phycoerythrin and commercial analogs such as SureLight P3; luminescent lanthanide chelates; luminescent semiconductor nanoparticles (e.g., quantum dots); phosphorescent materials, and microparticles (e.g., latex beads) that incorporate these excitable tags. For the purpose of this disclosure, the term "fluorophore" is used generically to describe all of the excitable tags listed here. The terms "fluorophore-labeled," "fluor-labeled," "dye-labeled," "dye-conjugated," "tagged," and "fluorescently tagged" may be used interchangeably in this disclosure.

The terms "color" and "color images" in this disclosure are intended as follows. "Color" may refer to a specific wavelength or wavelength band. However, "color images" are intended as meaning grayscale images formed while a sample is illuminated under a specific color. Thus, "two color images" is to be interpreted as two grayscale images formed under illumination by different colors at separate times. Similarly, a "color channel" refers to operation of a system herein during illumination with a specific color. For example, "electronic images recorded in different color channels" is to be interpreted as electronic images formed under illumination by different colors.

The embodiments described herein may be applicable to assays beyond fluorescence-based signal transduction. For example, the methods and systems may also be compatible with luminescence, phosphorescence, and light scattering based signal transduction.

In one embodiment, two color fluorescence microscopy based on laser illumination and differential immunostaining are used to identify and enumerate analytes in a sample. The present disclosure provides a method and system for performing this analysis. In one example, differential immunostaining with anti-CD4 and anti-CD14 antibodies may be used to identify CD4 T helper lymphocytes in blood. In another example, differential immunostaining with anti-CD4 and anti-CD3 antibodies are used to identify CD4 T helper lymphocytes in blood.

In another example, differential immunostaining with anti-CD4, anti-CD3, and anti-CD45 (three color system) are used to identify CD4 T helper cell percentage (% CD4) in a blood sample. In still another example, differential immunostaining with anti-CD4, anti-CD3, and anti-CD8 antibodies is used to identify and enumerate both CD4 and CD8 T lymphocytes such that the CD4/CD8 T lymphocyte ratio is obtained in addition to the CD4 T helper lymphocyte count.

The terms "T cells" and "T lymphocytes" may be used interchangeably in this disclosure. The terms "T helper cells," "CD4 T helper cells" and "CD4 T cells" may be used interchangeably in this disclosure to refer to those T helper cells that express CD4 on their surface.

For purposes of this disclosure, a cell that binds to a labeling molecule with substantial affinity may be termed "positive" for that particular labeling molecule. Conversely, a cell that does not bind to a labeling molecule with substantial affinity may be termed "negative" for that particular labeling molecule. For instance, a cell that binds an anti-CD4 antibody with a fluorescence tag and shows up as a detectable fluorescence event when illuminated may be termed "CD4 positive." Conversely, a cell that does not show up as a detectable fluorescence event after incubation with an anti-CD4 antibody with a fluorescence tag under the same or similar conditions may be termed "CD4 negative."

Plural or singular forms of a noun may be used interchangeably unless otherwise specified in the disclosure.

FIG. 1 illustrates a particle identification system 10 that is configured to receive and analyze a sample contained within a cartridge 13. Cartridge 13 accepts a fluid sample as described herein, and loads into system 10, as illustrated. Particle identification system 10 is operable to identify and/or count particles within the sample. Examples of particles include analytes such as CD4+ T-helper cells, other cell types, bacteria, viruses, fungi, protozoa, and plant cells. System 10 may also be operable to identify and/or count non-particle analytes such as proteins, peptides, prions, antibodies, micro RNAs, nucleic acids, and sugars.

Figure 2:
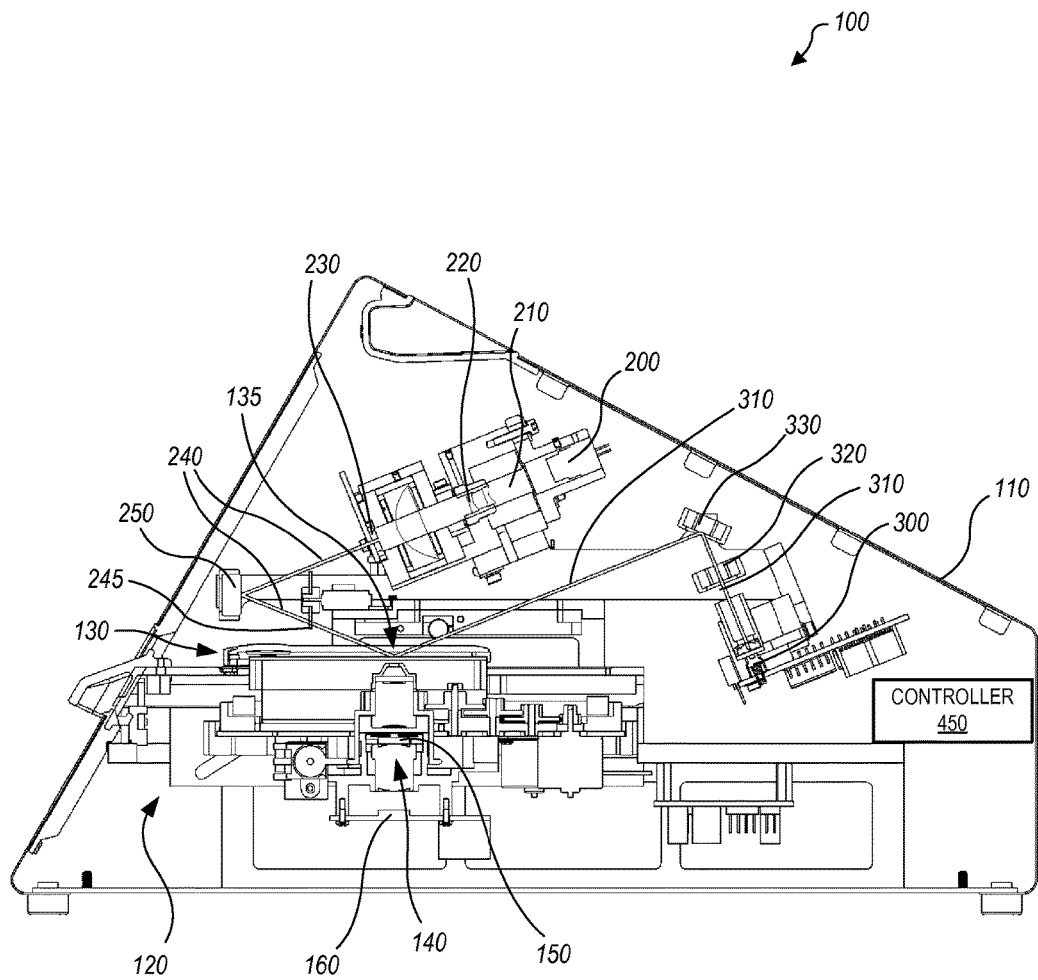
FIG. 2 shows a schematic cross sectional view of a particle identification system, in an embodiment.

FIG. 2 shows a schematic cross sectional view of one particle identification system 100. Particle identification system 100 is an example of particle identification system 10, FIG. 1. Elements of system 100 include:

- an enclosure 110 that provides mechanical support and optical isolation for system 100;
- a cartridge handling system 120 shown with a cartridge 130 in a measurement position; cartridge 130 containing the sample under test;
- imaging optics 140 including an emission filter 150, a focus adjusting system that adjusts focus of imaging optics with respect to cartridge 130 is not labeled in FIG. 2 (see FIG. 11);
- a sensor 160 that provides electronic images of a measurement field (MF) 135 of cartridge 130 that is imaged through imaging optics 140 and emission filter 150, imaging optics 140 and sensor 160 are sometimes referred to collectively herein as an imager;
- a first illumination module 200 emitting first electromagnetic radiation 210;
- a beam expander 220 and an aperture 230 for defining a first illumination beam 240 from first electromagnetic radiation 210;
- a first folding mirror 250 that reflects beam 240 so that beam 240 intersects cartridge 130 at measurement field 135;
- a rotating phase plate 245 through which beam 240 passes;
- a second illumination module 300 that emits second electromagnetic radiation as a second illumination beam 310;
- an excitation filter 320;
- a second folding mirror 330 that reflects beam 310 so that beam 310 also intersects cartridge 130 at measurement field 135; and
- a controller 450. FIG. 2 shows controller 450 within enclosure 110, and controller 450 may be provided within enclosure 110 but may, alternatively, be provided externally to enclosure 110 (e.g., through electrical and/or wireless connections to a computer or network). Controller 450 is described in greater detail in connection with FIG. 11.

System 100 works by sequentially illuminating a stained sample within cartridge 130 to cause fluorescence of particles within the sample, capturing images of the fluorescence, and analyzing the images to identify particles in the sample and to determine the presence of biological markers therein. The illumination is by electromagnetic radiation which is typically visible light, but radiation of other types (e.g., infrared, ultraviolet) may also be utilized by adapting the modalities described herein. The systems and methods described herein provide a user interface and robust clinical capabilities by identifying and counting analytes in even unfiltered whole blood samples, although they can also work with lysed, diluted, and/or filtered samples. Details of system 100, cartridge 130 and associated methods and software to do so are now provided. It should be clear that cartridge 130 is compatible with system 100, but it is appreciated that cartridge 130 may also be usable in other readers. Likewise, other cartridges could be usable in system 100.

As shown in FIG. 2, the optical paths of illumination beams 240 and 310 are separate, permitting separate optimization thereof. Given the typical sense of "copropagating" in optics as meaning that two light beams share an optical path (as is often the case in microscopes and flow cytometers), beams 240 and 310 are nowhere copropagating. Illumination beam 240 may be nominally green light (e.g., having a peak wavelength of about 510 to 550 nm), which is strongly absorbed by red blood cells. Use of light in this wavelength range can lead to localized heating of a blood sample, causing motion of cells in the sample that may complicate measurements. The optical path of illumination beam 240 can therefore include an aperture that limits the size of, and thus the optical power transmitted by, beam 240 toward cartridge 130. Illumination beam 310 may be nominally red light (e.g., having a peak wavelength of about 625 to 670 nm). Illumination modules 200 and 300 may be any type of electromagnetic radiation sources such as, without limitation, solid state lasers, gas lasers, fiber lasers, LEDs, superluminous LEDs or filtered incandescent or fluorescent light sources.

Figure 3:
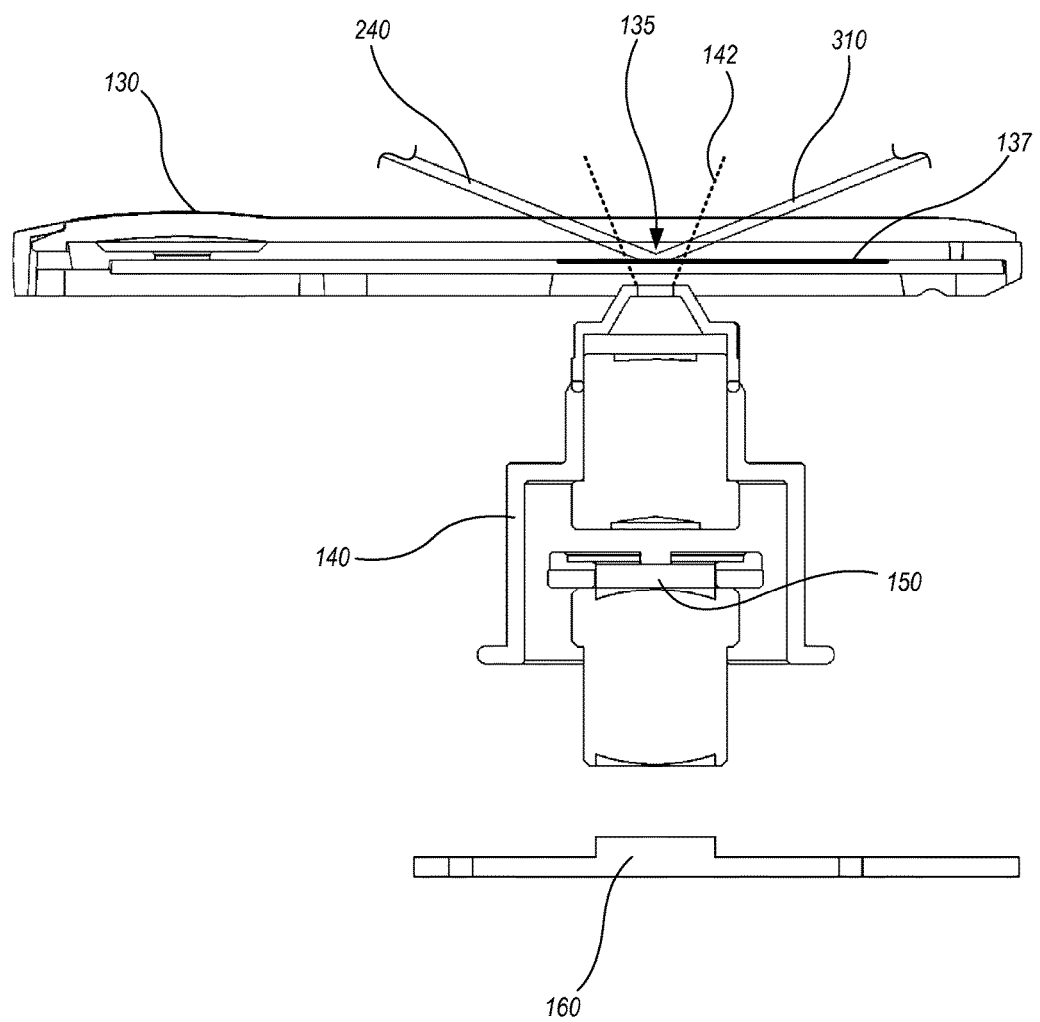
FIG. 3 shows an enlarged, schematic cross sectional view of a portion of the system of FIG. 2, with certain structure removed for clarity.
Figure 4:
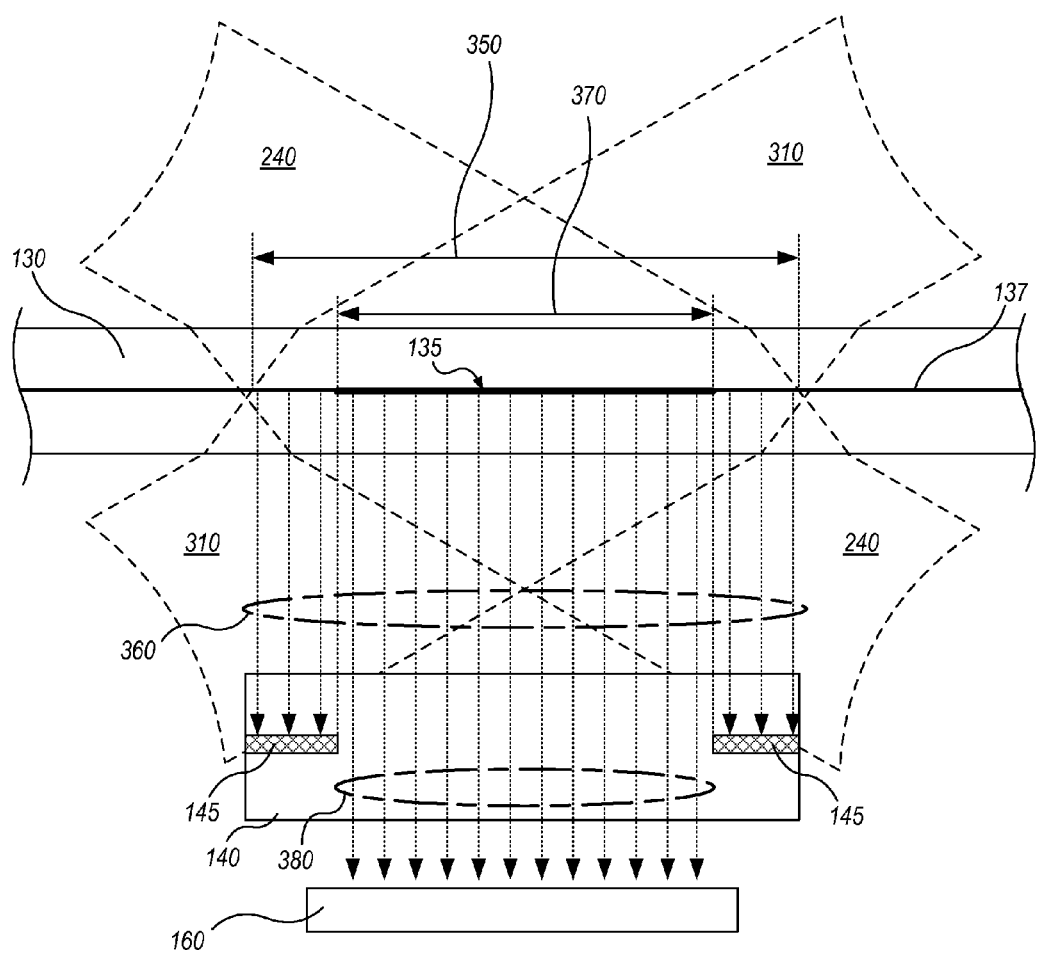
FIG. 4 schematically shows a region immediately surrounding a measurement field within the system of FIG. 2.

Illumination beams 240 and 310 may be advantageously arranged such that their incidence on, and reflections from, cartridge 130 are at angles that fall outside a numerical aperture of imaging optics 140. This helps improve signal to noise ratio of images captured by sensor 160. Although FIG. 2 shows illumination beams 240 and 310 impinging on MF 135 from one side of cartridge 130 and imaging optics 140 being on the other side of cartridge 130, it is contemplated that one or both (or more) illumination beams may be on the same side of cartridge 130 as imaging optics 140. In FIGS. 2-4, illumination beams 240 and 310 are shown as being coplanar (that is, each of beams 240 and 310 lies in the plane of the cross-section). Alternatively, in embodiments, illumination beams may be reconfigured so as not to be coplanar.

It is also appreciated by one skilled in optics that similar systems could be implemented without or with fewer or more folding mirrors than are shown in system 100, FIG. 2. Also, additional illumination modules and optical paths may be included to form, e.g., a three-wavelength or four-wavelength system.

Phase plate 245, through which beam 240 passes, has a characteristic feature size and a rotation rate to decohere laser light such that laser speckle effects or other interference-induced illumination nonuniformity in beam 240 are averaged out over the duration of a measurement. As shown, system 100 includes phase plate 245 only in the path of beam 240, but it is contemplated beam 310 could pass through an identical or similar phase plate if similar effects are expected in beam 310.

FIG. 3 shows an enlarged, schematic cross sectional view of a portion of the system of FIG. 2, with certain structure removed for clarity of illustration. Illumination beams 240 and 310 are directed towards measurement field 135, where cartridge 130 holds a sample within a detection region 137 (detection region 137 is an example of detection region 2700; see FIGS. 47, 48). Detection region 137 is depicted as a heavy line and is not to scale. Imaging optics 140 image measurement field 135 onto sensor 160, which generates electronic images of measurement field 135 that are further processed to identify analytes in the sample. In the context of the present document, a "measurement field" is therefore a portion of a sample within detection region 137, and corresponds to a field of view of imaging optics 140 through detection region 137, or a portion of such field of view as imaged by sensor 160, as described below. Imaging optics 140 include an emission filter 150 that filters out light that is not within the wavelength range(s) corresponding to fluorescence emitted by the analytes, and light that is in the wavelength range(s) corresponding to illumination 240 and 310 when incident on cartridge 130, thus improving signal to noise ratio of the electronic images. Although emission filter 150 is shown within optics 140 in FIGS. 2 and 3, other embodiments may include emission filter at other locations, or may omit emission filter 150 completely. FIG. 3 also shows an admittance cone 142 of imaging optics 140 that is defined by the numerical aperture of optics 140. Although the angles of admittance cone 142 and illumination beams 240 and 310 may not be to scale in FIG. 3, the numerical aperture of optics 140 and therefore the angle of admittance cone 142 are chosen such that illumination beams 240 and 310 will not enter imaging optics 140. It is appreciated that this choice helps keep illumination beams 240 and 310 themselves, or partial reflections thereof propagated at similar angles through cartridge 130, from entering imaging optics 140 where they could degrade the signal to noise ratio of the system.

Emission filter 150 may be a dual-bandpass filter with one bandpass set to transmit at least a portion of the fluorescence emission produced when illuminating with illumination beam 240, and the other bandpass set to transmit at least a portion of the fluorescence emission produced when illuminating with illumination beam 310, while blocking light at the wavelengths of illumination beams 240 and 310. If more illuminations are added, the number of bandpasses in emission filter 150 may be increased (e.g., three lasers and a triple-bandpass filter). In one embodiment, multiple single-bandpass emission filters are placed in a filter-changing mechanism that is motorized and controlled by a control system. In yet another embodiment, fluorophores are chosen to share an emission wavelength range and have significantly different excitation spectra, such that they are selectively excited by individual illumination beams but detected using a single emission filter having a single bandpass. In a further embodiment, fluorophores are chosen to share an excitation wavelength range and have significantly different emission spectra, such that all fluorophores are excited by the same illumination while a filter-changing mechanism with multiple single-bandpass filters is used to selectively detect emission from different fluorophores.

FIG. 4 schematically shows a region immediately surrounding measurement field 135, which is depicted as a heavy line that is not to scale. Illumination beams 240 and 310 intersect, and are refracted by, cartridge 130 to form an illuminated region of detection region 137 that has a width 350, as shown. Fluorescently tagged analytes within detection region 137, if present, may emit fluorescence in all directions; only fluorescent rays 360 propagating in the direction of imaging optics 140 are depicted in FIG. 4. Imaging optics 140 may include an aperture stop 145 that is shown schematically in FIG. 4; one skilled in the art will appreciate that the location and geometry of aperture stop 145 within optics 140 may be different from the exact location and geometry shown in FIG. 4. In particular, aperture stop 145 may be located on a surface of optics 140 that faces cartridge 130. If aperture stop 145 is located within optics 140 at a position where the image of measurement field 135 is not at 1:1 magnification, then aperture stop 145 may be sized differently than shown in FIG. 4. Aperture stop 145 stops fluorescent rays 360 except for rays 380 that emanate from a width 370 within detection region 137. Rays 380 continue to sensor 160. Width 370 therefore laterally defines measurement field 135.

In alternative embodiments, imaging optics 140 do not include aperture stop 145, but may instead create an image of rays 360 that exceeds a size of sensor 160 at a focal plane of the optics, in which case the size of sensor 160 laterally defines width 370 and measurement field 135. In another embodiment, imaging optics 140 may include a field stop (not shown in FIG. 4) to increase the depth of field.

Several aspects of cartridge 130 are advantageously arranged to improve sensitivity of system 100 to particles bearing biological markers. In one embodiment, cartridge 130 is fabricated of an optical grade, clear material to enable distortion free and loss free imaging of the sample therethrough. The material may be a low autofluorescence plastic such as cyclic olefin polymer, cyclic olefin copolymer, polystyrene, polymethylmethacrylate, polycarbonate, etc. to avoid generating stray background light, from which fluorescence of sample particles would have to be distinguished. A precisely known height of a fluidic channel within cartridge 130, including each of the MFs to be measured, may be a critical dimension. If a field of view of optics 140 determines a two-dimensional area of a measurement field of the sample being measured, the channel height times the area will determine the volume, such that knowing the height precisely limits the measurement accuracy of particle concentration by volume. Filling of the channel from floor to ceiling (e.g., in the dimension parallel to the optical axis of the imaging system) can be achieved through an appropriate combination of channel height and surface energy. The surface energy can be increased by, e.g., plasma cleaning and/or chemical surface modification. Cartridge 130 may be configured with an advantageously small channel height to aid filling. A small channel height dimension further reduces the absorption of excitation illumination and fluorescence emission by sample components such as red blood cells.

A wide viewing angle in optics 140 limits a depth of field of the imaging system formed by imaging optics 140 and sensor 160. It is advantageous to count all particles within a MF in a single image, rather than acquiring several images at varying focus depths within a sample and sorting unique from non-unique particles within the images. For this reason, it may be desirable to match the depth of field of the imaging system to the channel height. That is, the imager having a depth of field that is commensurate with channel height may be regarded as the channel height being within ±20% of the depth of field of the imager along a viewing axis of the imager. Alternatively, if depth occupied by fluorescently labeled particles within the cartridge is known, it may be desirable to match the depth of field of an imager to such depth. That is, the imager having a depth of field that is commensurate with depth occupied by fluorescently labeled particles within the cartridge may be regarded as that depth being within ±20% of the depth of field of the imager along a viewing axis of the imager. It may also be desirable to make portions of cartridge 130 adjacent to the MF much thicker than the depth of field (so that stray material such as dust and fingerprints outside the sample chamber is substantially out of focus, minimizing the chances that such material will distort images or be mistaken for a target analyte). This is illustrated further in FIG. 5.

Figure 5:
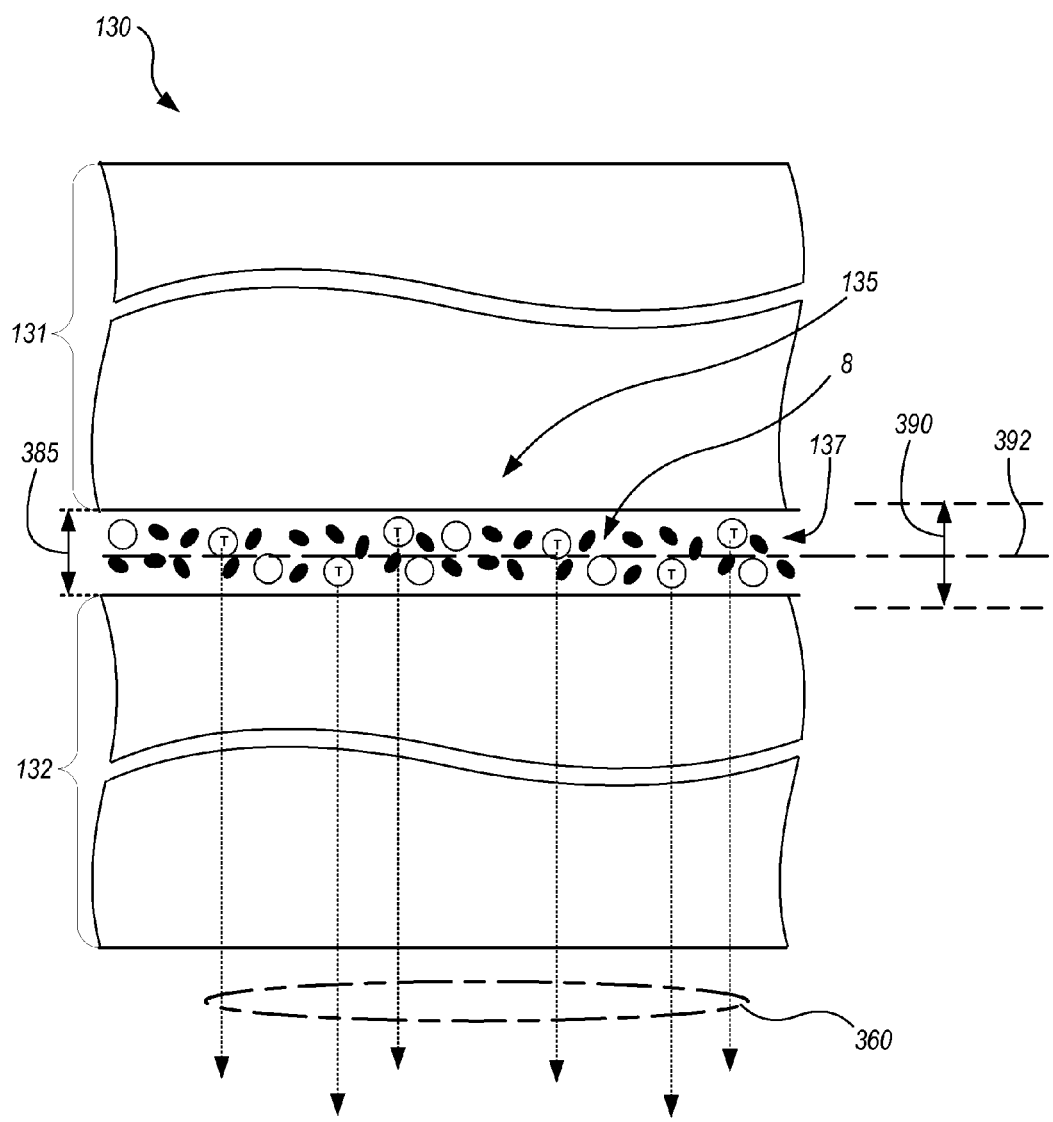
FIG. 5 shows details of structures at and surrounding the measurement field depicted in FIG. 4.

FIG. 5 shows details of structures within, and vertically surrounding, a portion of measurement field 135 within cartridge 130. Measurement field 135 is shown with a sample 8 therein. When illuminated by illumination beams 240 and/or 310 (see FIGS. 2 through 4), fluorescently labeled analytes designated as T emit fluorescent rays. Although only fluorescent rays 360 propagating in the direction of the imaging optics 140 are shown in FIG. 4, it is understood that fluorescently labeled analytes T may emit in all directions. As discussed above, imaging optics 140 and/or sensor 160 laterally define measurement field 135 outside of the portion shown in FIG. 5. Detection region 137 within cartridge 130 has a channel height 385, which as discussed above is another dimension needed to define a volume of sample 8. Imaging optics 140 (see FIGS. 2 through 4) have a depth of field 390 centered about a focal plane 392 within detection region 137. In the embodiment shown in FIG. 5, depth of field 390 is advantageously about the same as, or slightly greater than, channel height 385. Cartridge 130 includes upper and lower elements 131, 132 that bound detection region 137 and, to the extent that these elements are optically transmissive, they are much thicker than depth of field 390, to keep nuisance artifacts outside cartridge 130 out of focus. For example, either or both of upper and lower elements 131, 132 may be an optically transmissive, planar substrate that is at least three times thicker than a depth of field of imaging optics 140 along a viewing axis of the imager. In other embodiments, channel height 385 may be greater than depth of field 390; in these embodiments imaging may be coordinated with focus adjustments of imaging optics 140 to provide multiple measurement fields separated by height within cartridge 130.

When a measurement of analyte concentration within a volume is based on a number of analytes detected within a two-dimensional projection of the volume, the accuracy of the measurement is limited by the accuracy to which the third dimension, eliminated in the projection, is known. This situation is encountered, for example, when the number of analytes in a volume is determined by two-dimensional imaging of the volume, like the situation presented in FIGS. 2-5. In cases where uncertainty in the third dimension is the dominant contributor to the uncertainty of the analyte concentration, the relative uncertainty of the analyte concentration equals the relative uncertainty of the extent of the third dimension. This is critically important when a particle identification system is designed to operate on microliter or picoliter quantities of biological samples (e.g., one or two drops of blood) because the channel height that defines the third dimension may be on the order of tens of microns, and such heights are difficult to provide with high precision (e.g., with tolerances of less than around 10%). Surfaces may be either physical (e.g., defined by physical materials) or defined by aspects of the detection. Examples of physical surfaces include substrates, membranes, and material discontinuities. Examples of non-physical surfaces include detection aspects such as the depth of field of an imaging system or endpoints of a scan along the direction of projection.

The average analyte concentration n in a volume V is given by n=N/V, where N is the number of analytes within the volume. The volume V is the local volume height, $h_{local}$, integrated over the projected area, A, included in the measurement. This integration reduces to the area-weighted average of the local height, $h_{average}$. With these definitions, the volume V can be written as V=A×$h_{average}$. Consequently, the analyte concentration is given by n=N/(A×$h_{average}$). This equation underlines the importance of an accurate determination of the volume height. Actual knowledge of the local volume height, $h_{local}$, is not required. It is sufficient to determine the $h_{average}$, i.e., the area-weighted average of the local height.

Figure 6:
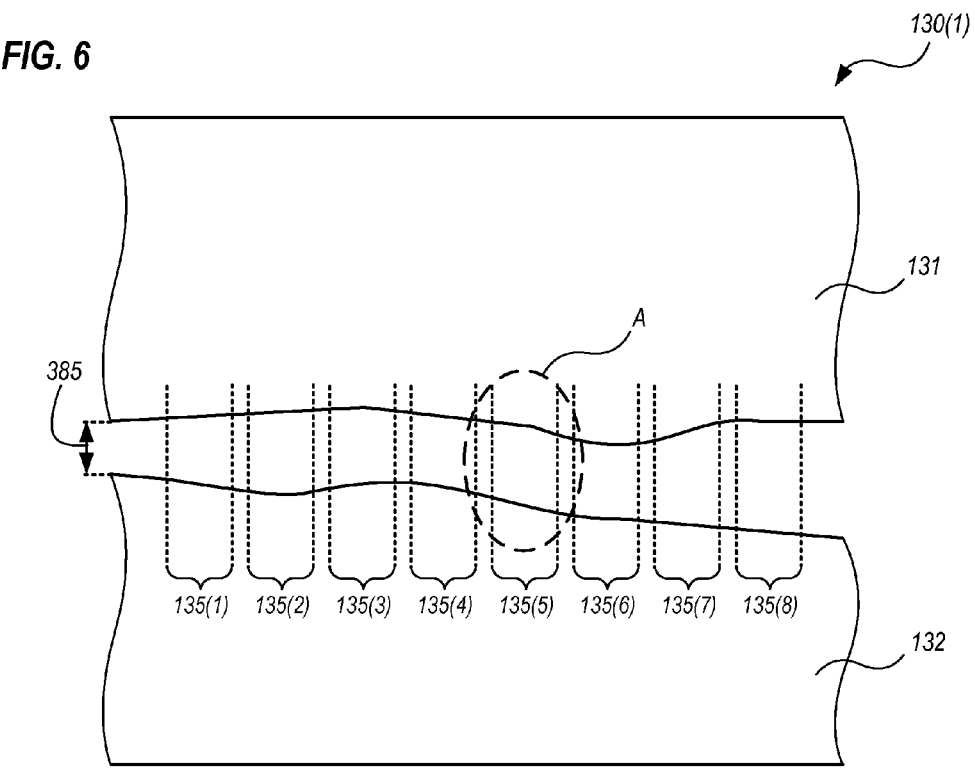
FIG. 6 schematically shows a portion of a cartridge, formed of upper and lower elements, in an embodiment.
Figure 7:
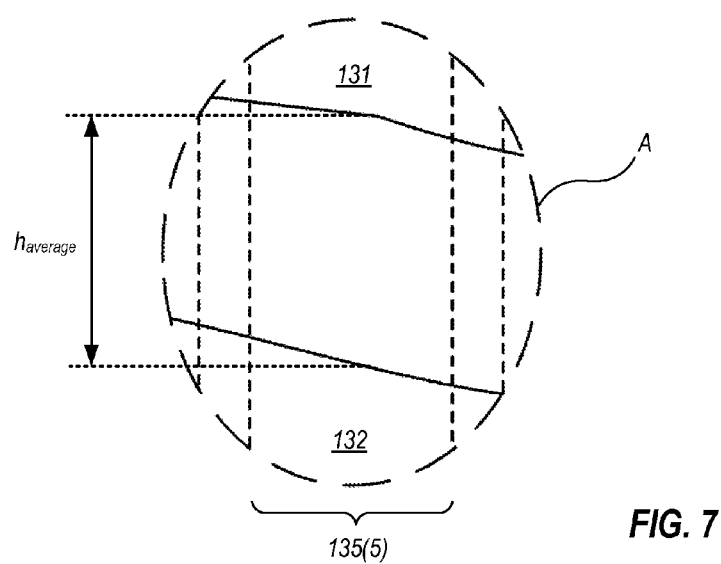
FIG. 7 is a detail view of a portion of the cartridge shown in FIG. 6.

Channel height 385 (FIG. 5) is often determined by parameters that are not intrinsic to the detection system (the cartridge-reading instrument only, excluding the cartridge) for instance a distance between upper and lower elements 131, 132 in cartridge 130. FIG. 6 schematically shows a portion of a cartridge 130(1), formed of upper and lower elements 131, 132. Cartridge 130(1) exhibits variation of channel height 385 across measurement fields 135(1) through 135(8) (represented by dashed lines crossing detection region 137, since measurement fields 135 are defined as areas imaged by optics of a reader, as per the discussion above, in connection with FIG. 4). Certain features in FIG. 6 are exaggerated for illustrative purposes. A portion of FIG. 6 designated as A is shown in detail in FIG. 7, indicating $h_{average}$ within measurement field 135(5) of cartridge 130(1).

In one embodiment, measurement of analytes may be performed together with a measurement of $h_{average}$ for each measurement field. In another embodiment, channel height 385 may be mapped out and recorded in advance of the analyte measurement and applied in the calculation of the deduced analyte concentration. For instance, a channel height measurement may be performed during production of cartridge 130. In an embodiment, a characterization of channel height 385, in the form of, e.g., a single $h_{average}$ or a map consisting of a series of $h_{average}$ values, may be encoded on cartridge 130 and read either by an operator or by an instrument. For instance, a barcode or other machine-readable information that contains channel height information may be labeled on a cartridge 130, and the barcode may be read by a barcode reader at the time of analyte measurement. The barcode reader may be integrated in the instrument performing the analyte measurement (e.g., system 100), it may be connected to the instrument, or it may be separate from the instrument.

A channel height characterization for individual cartridge 130 may be integrated in the cartridge production process. The characterization may be performed on all cartridges or it may be performed on a subset of devices, for instance a suitable number of cartridge 130 may be extracted from each production run or each lot of cartridges provided to a customer. Techniques for characterizing channel height include but are not limited to white light interferometry in transmission or reflection mode. Ideally, for preservation of materials, the measurement is non-destructive. That is, the cartridges exposed to the measurement are still usable for analyte concentration measurements. Optical interrogation methods are ideal for this purpose as long as the relevant surfaces of the cartridges can be accessed optically. In the case of analyte detection systems based on imaging or other optical detection schemes, an optical path through the cartridge that is used by the detection system can be used for characterizing the channel height. Other access paths, if available, may also be used.

Figure 8:
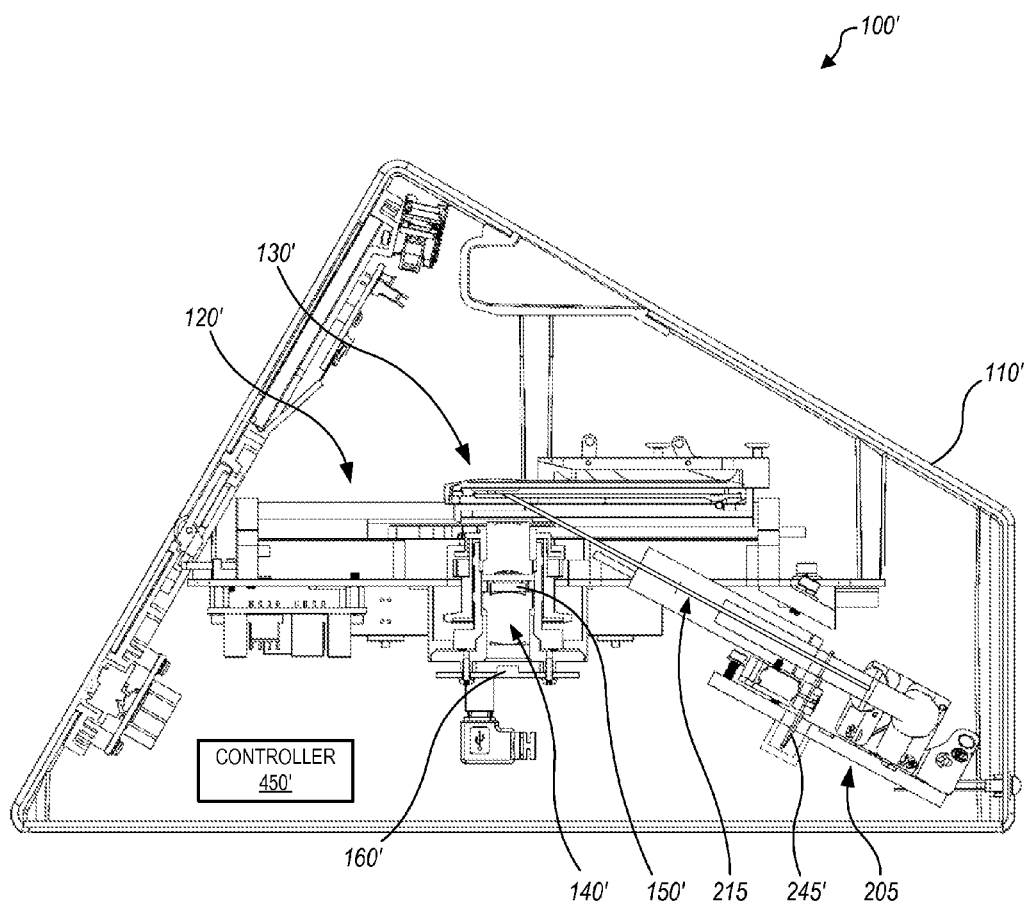
FIG. 8 shows a schematic cross sectional view of a particle identification system, in an embodiment.

FIG. 8 shows a schematic cross sectional view of one particle identification system 100'. Particle identification system 100' is an example of particle identification system 10, FIG. 1. Elements of system 100' include:

- an enclosure 110' that provides mechanical support and optical isolation for system 100';
- a cartridge handling system 120' shown with a cartridge 130' in a measurement position; cartridge 130' containing the sample under test;
- imaging optics 140' including an emission filter 150', a focus adjusting system that adjusts focus of imaging optics with respect to cartridge 130' is not labeled in FIG. 8 (see FIG. 11);
- a sensor 160' that provides electronic images of a measurement field (MF) of cartridge 130' that is imaged through imaging optics 140' and emission filter 150' imaging optics 140' and sensor 160' are sometimes referred to collectively herein as an imager;
- an illumination subassembly 205 that includes first and second illumination modules (not shown in the cross-sectional plane of FIG. 8) emitting first and second illumination along a common beam path 215 that intersects cartridge 130' at measurement field 135';
- a rotating phase plate 245' through which beam path 215 passes; and
- a controller 450'. FIG. 8 shows controller 450' within enclosure 110', and controller 450' may be provided within enclosure 110' but may, alternatively, be provided externally to enclosure 110' (e.g., through electrical and/or wireless connections to a computer or network). Controller 450' is described in greater detail in connection with FIG. 11.

Cartridge handling system 120' accepts cartridge 130' from an operator that loads cartridge 130' into a slot (not shown) in a front panel of enclosure 110'. Thereafter, cartridge handling system 120' moves cartridge 130' into place for imaging by sensor 160' through imaging optics 140', including repositioning cartridge 130' for imaging of specific measurement fields therein. As opposed to the arrangement of particle identification system 100, FIG. 2, particle identification system 100' is configured for same side imaging, that is, beam path 215 impinges on cartridge 135' from the same side as the optics used to image measurement fields within cartridge 135'. Consequently, optical access to the sample is required from one side only, and cartridge materials on the opposite side of the detection region from the illumination and the optics need not be transparent. This has multiple benefits. For instance, labels can be applied to the side of the cartridge that does not face the illumination and optics. Also, the same side of the cartridge can be formed of opaque and/or light absorbing material that is well-suited for laser welding. The same side of the cartridge may also be of any color, for easy identification, and requires no particular optical performance or features.

Illumination subassembly 205 utilizes a dichroic beam-combiner to combine two illumination beams (e.g., of different wavelength bands, for stimulating different fluorescent labels) prior to the beams being directed along beam path 215 toward cartridge 135'. This allows for complete assembly and alignment of illumination subassembly 205 before installation into system 110', as well as minimizing a number of optical paths into the cartridge area.

Figure 9:
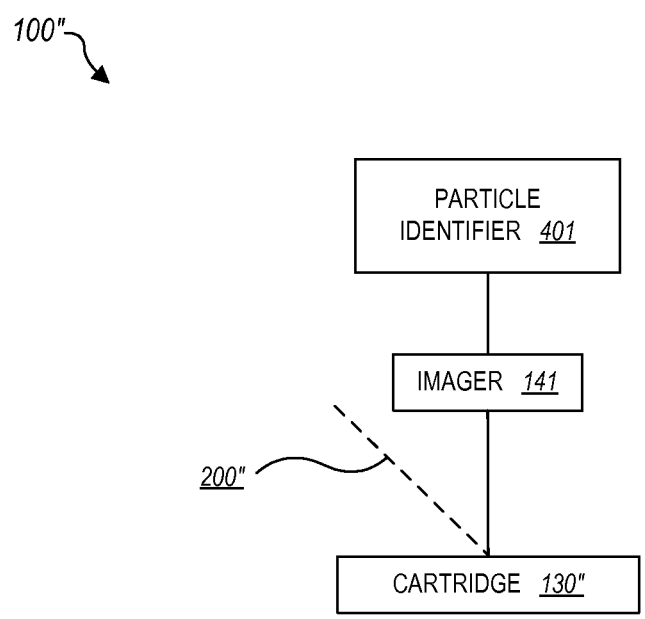
FIG. 9 is a schematic block diagram of a particle identification system, in an embodiment.

FIG. 9 is a schematic block diagram of a particle identification system 100". Particle identification system 100" is an example of particle identification systems 10, 100, 100'. System 100 includes a cartridge 130" that contains a sample with fluorescently labeled particles. A region within cartridge 130" is illuminated by illumination 200"; at least one measurement field of cartridge 130" is imaged by imager 141 that provides wavelength-filtered electronic images of the measurement fields to a particle identifier 401, as shown. Particle identifier 401 processes the electronic images to determine a superset of particles of interest, and determines fluorescently labeled particles within the superset based on properties of the fluorescently labeled particles in the at least one measurement field.

Figure 10:
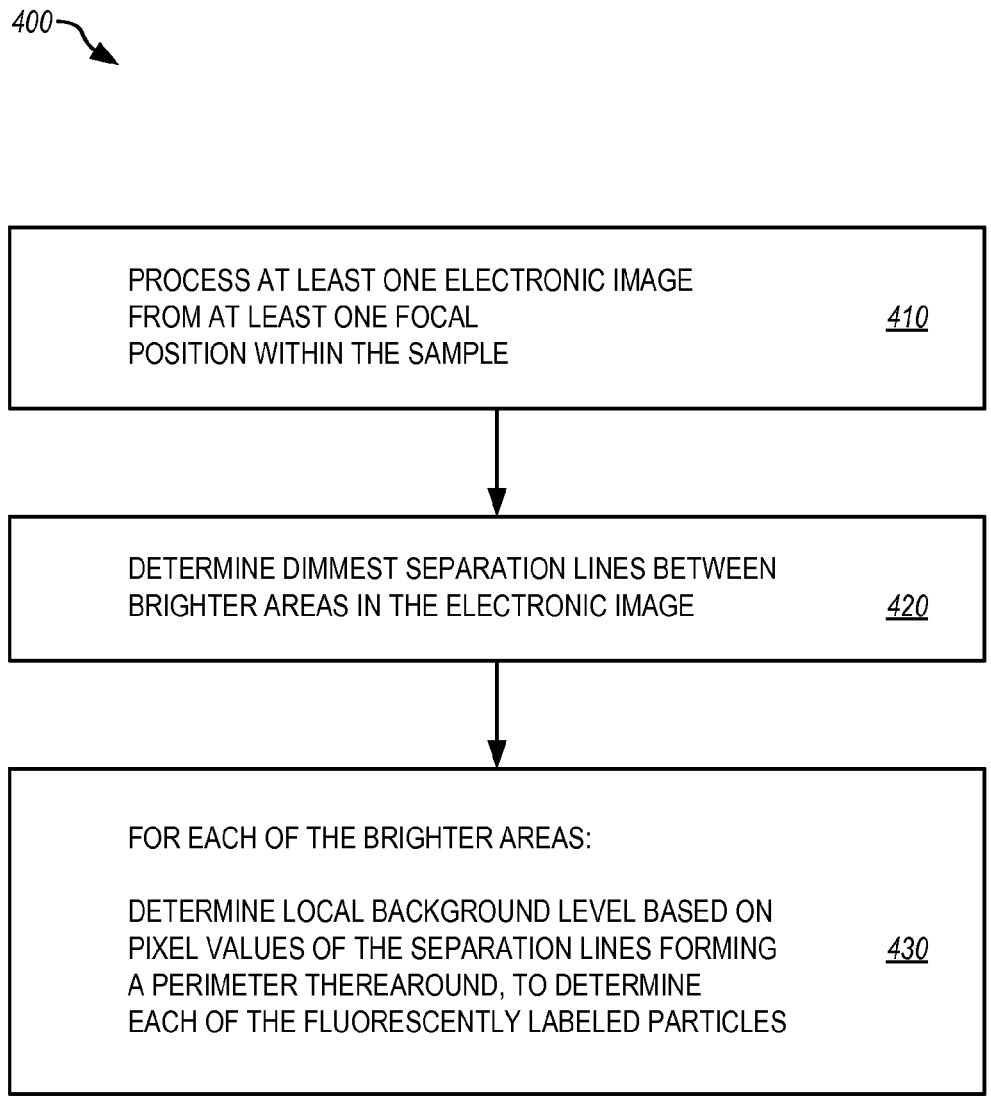
FIG. 10 is a flowchart of a method for determining fluorescently labeled particles within a sample, in an embodiment.

FIG. 10 is a flowchart of a method 400 for determining fluorescently labeled particles within a sample. Step 410 processes at least one electronic image from at least one focal position within the sample. Step 420 determines dimmest separation lines between brighter areas in the electronic image. Step 430, for each of the brighter areas, determines local background level based on pixel values of the separation lines forming a perimeter therearound, to determine each of the fluorescently labeled particles. Examples and details of steps 410 through 430 are provided below in connection with FIGS. 11 through 30.

Figure 11:
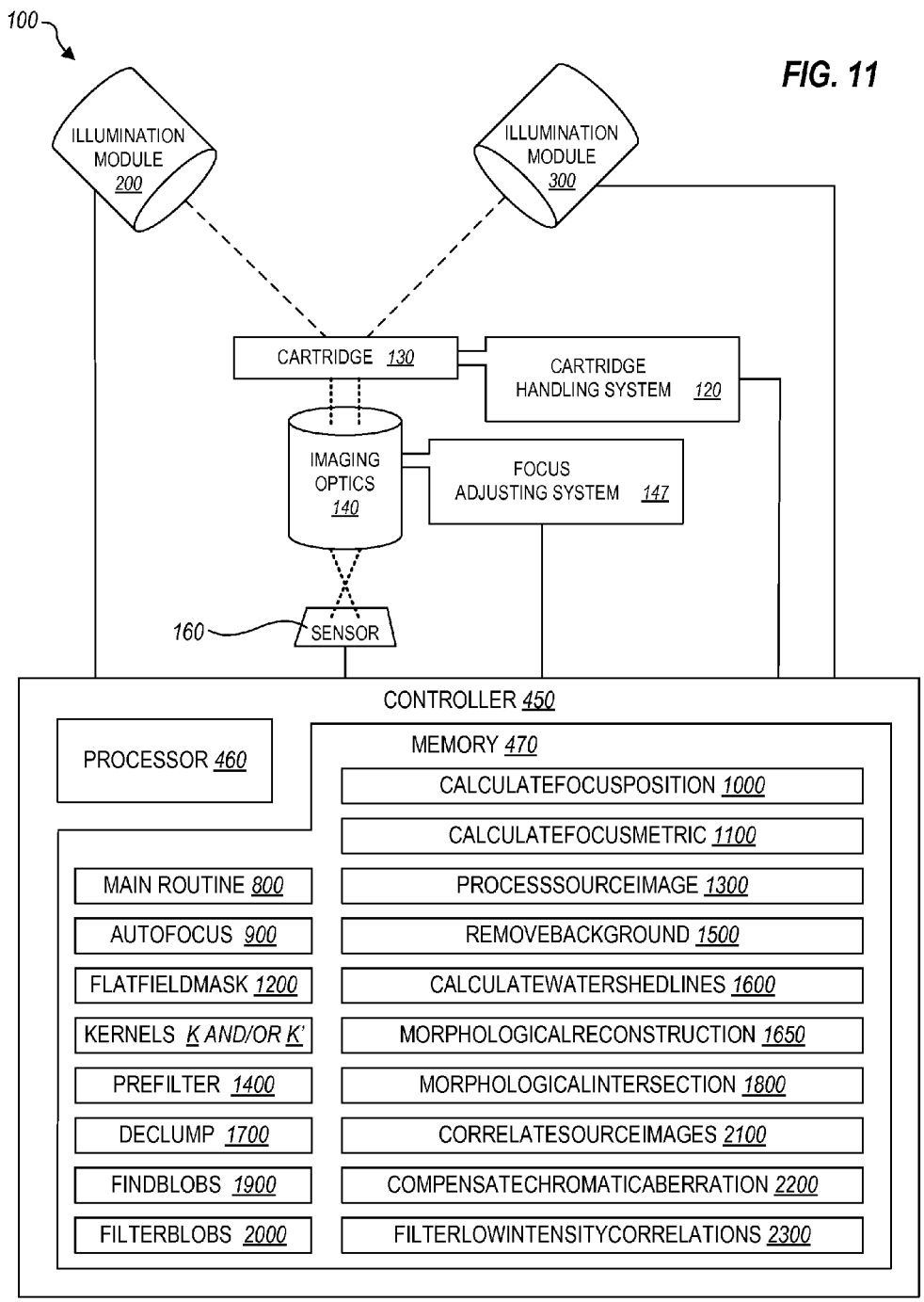
FIG. 11 is a schematic block diagram of a particle identification system, in an embodiment.

FIG. 11 is a schematic block diagram illustrating functional relationships between certain components of systems 100, 100' and/or 100" (labeled collectively in FIG. 11 as 100) and illustrating features of controllers 450 thereof (the components shown in FIG. 8 are referenced by their corresponding numbers in FIG. 2 for simplicity in the discussion of FIG. 11). Cartridge 130 is positioned by cartridge handling system 120 with respect to imaging optics 140. Illumination modules 200, 300 provide illumination for cartridge 130. Imaging optics 140 are focused by focus adjusting system 147 as discussed further below, to adjust focus of cartridge 130 on sensor 160. As noted above, controller 450 may be integrated within enclosure 110 of systems 100, 100', or may be provided externally to enclosure 110 through electrical or wireless connections. Connections between controller 450 and other components of systems 100, 100' that provide information transfer, image transfer or control are shown in solid lines, while optical relationships among some of the components are shown as broken lines. Connections within controller 450 are not shown, for clarity of illustration.

Controller 450 includes a processor 460 that is typically a microprocessor or microcontroller, but could be implemented in other known ways (e.g., with discrete logic, ASIC or FPGA semiconductors, or other electronic hardware with equivalent functionality). Controller 450 also includes memory 470 for storing software, filter kernels, images, calculations and results thereof. FIG. 11 shows memory 470 storing filter kernels K and/or K', and exemplary software instructions for methods including main routine 800, auto focus 900, calculate focus position 1000, calculate focus metric 1100, flat field mask 1200, process source image 1300, prefilter 1400, remove background 1500, calculate watershed lines 1600, morphological reconstruction 1650, declump 1700, morphological intersection 1800, find blobs 1900, filter blobs 2000, correlate source images 2100, compensate chromatic aberration 2200 and filter low intensity correlations 2300. Kernels K and/or K', and the software instructions illustrated in FIG. 11 are described in greater detail below, in connection with FIGS. 13-30. Upon executing some or all of the software noted above, controller 450 functions as particle identifier 401, FIG. 9.

Figure 12:
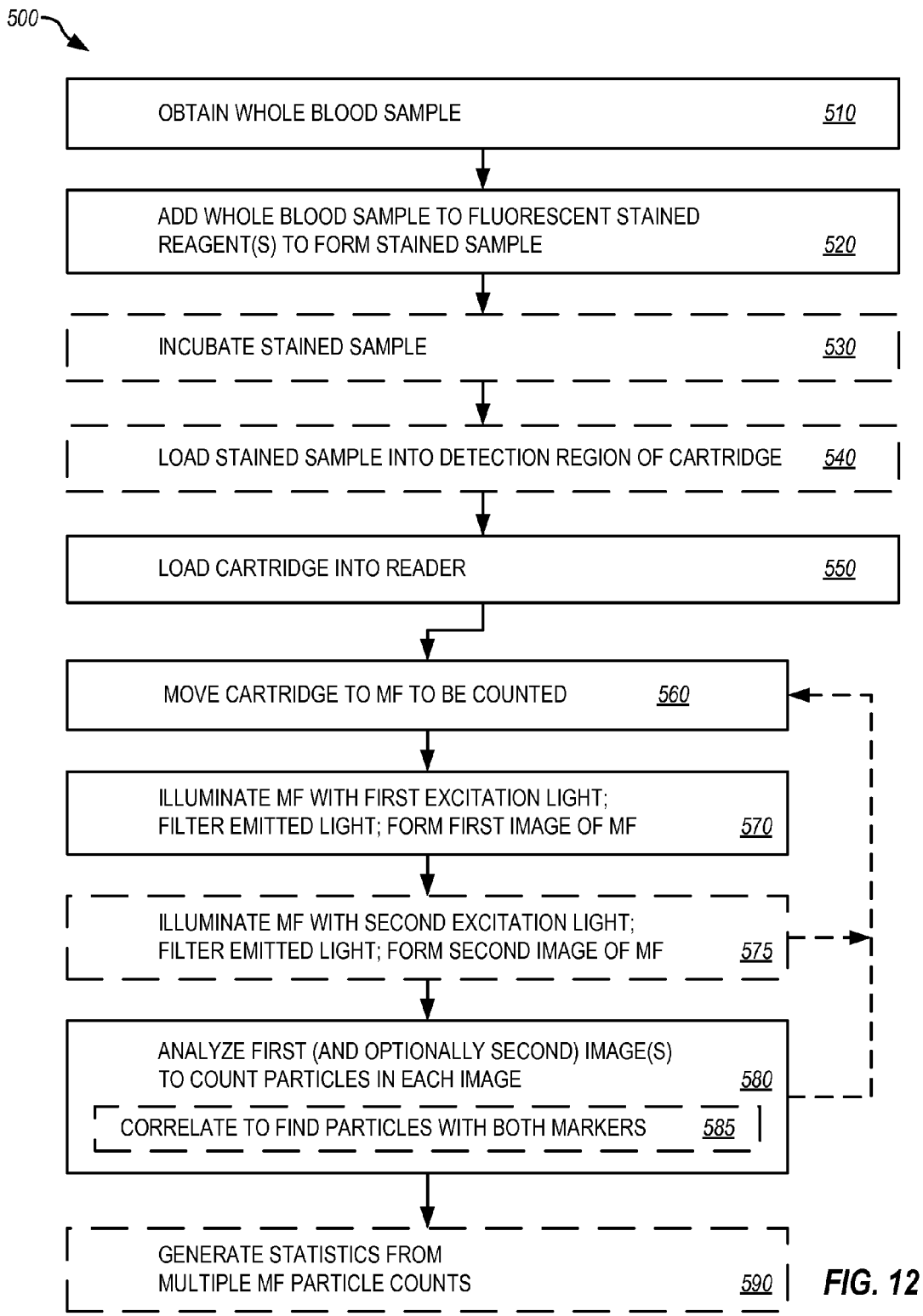
FIG. 12 is a flowchart of a method of determining fluorescently labeled particles in a sample, in an embodiment.

FIG. 12 is a flowchart of a method 500 of counting particles in a sample. Steps 550 through 590 are steps that may be performed entirely by particle identification systems described herein; steps 510 through 530 may be performed utilizing some of the system described herein or with other tools, while steps 580 through 590 are image processing and statistical analysis steps that may be performed by certain embodiments but could also be performed utilizing a computer, calculator or the like, or not at all. Certain steps of method 500 shown in FIG. 12 are high-level descriptions of exemplary procedures that will be described in greater detail below. It is appreciated that some of the procedures described further below are optional, but may increase precision of particle counts. Also, method 500 is described in the context of both physical, data-taking steps (e.g., the steps wherein a sample is obtained, processed and imaged) and image processing that results in particle counts, but the image processing steps can also be performed on images that are stored or obtained by other means than the physical data-taking steps. Where the following discussion pertains to specific components noted in FIG. 2, it also pertains to the same-named components noted in FIG. 8 (e.g., sensor 160 pertains to sensor 160', controller 450 pertains to controller 450' etc.).

Step 510 obtains a whole blood sample from a patient. In embodiments, a cartridge (e.g., cartridge 13 or 130, FIGS. 1-5) includes an inlet port that can be touched directly to a capillary whole blood droplet (e.g., from a finger stick). Such cartridge may also include features that promote capillary action to draw the blood droplet into the cartridge (see also FIGS. 45 through 50). Alternatively, the capillary blood sample may be collected via an uncalibrated or calibrated transfer pipette. In another embodiment, the sample is venous whole blood collected in a blood tube (e.g., BD Vacutainer®). Step 520 adds the whole blood sample to one or more fluorescently stained reagent(s) to form a stained sample. In embodiments, the fluorescently stained reagent(s) may be provided in the cartridge; alternatively, the reagent(s) may be combined externally to the cartridge (for example, in a microtube) to form the stained sample, which is then loaded into the cartridge. An optional step 530 incubates the stained sample to provide time for the reagent(s) to mix and/or react with the whole blood sample. Step 530 may also be performed while the stained sample is outside the cartridge, and/or in the cartridge. Also, step 530 may be performed partly while the sample is in the detection region. Step 540 loads the stained sample into a detection region of the cartridge. In the case of a cartridge supplied with reagents therein, step 540 is the same as steps 510 and 520, that is, the cartridge itself obtains the whole blood sample and draws the sample into the detection region. Reagents may be located in a reagent region upstream from the detection region and/or in the detection region. In other embodiments, the sample and reagents are mixed outside the cartridge, and are loaded into the cartridge (including a detection region thereof) in step 540.

Step 550 loads the cartridge into a reader (e.g., systems 100, 100', FIG. 2 and FIG. 8). Step 560 moves the cartridge to a measurement field to be counted, that is, the reader operates a mechanism that moves the cartridge to a location such that illumination sources and imaging optics can cooperate to perform steps 570 and 575. Step 560 may be performed, for example, as part of main routine 800, described later in connection with FIG. 13. There may be only one, or many, such measurement fields within a cartridge; having multiple measurement fields provides improved statistical accuracy for particle counts. Step 570 illuminates a measurement field with a first excitation light, filters emitted light from the sample, and forms a first image of the measurement field. Step 570 may be performed, for example, as part of main routine 800, described later in connection with FIG. 13. An example of step 570 is utilizing first illumination module 200 and associated optics (see, e.g., FIG. 2) to form illumination beam 240, illuminating the measurement field with beam 240, passing fluorescence from stained particles within the sample through imaging optics 140 and emission filter 150, and acquiring an image of the measurement field with sensor 160. The image acquired in step 570 may be sufficient for some purposes. An optional step 575 illuminates the same measurement field with a second excitation light, filters emitted light from the sample, and forms a second image of the measurement field. Step 575 may also be performed, for example, as part of main routine 800, described later in connection with FIG. 13. An example of step 575 is utilizing second illumination module 300 and associated optics (see, e.g., FIG. 2) to form illumination beam 310, illuminating the measurement field with beam 310, passing fluorescence from stained particles within the sample through imaging optics 140 and emission filter 150, and acquiring an image of the measurement field with sensor 160.

Step 580 analyzes at least the first, and optionally the second image(s) to count fluorescent particles in each image. Step 580 may include execution of the software instructions illustrated in FIGS. 16, 17, 19-27 and 30, and may include convolution of images with kernels K or K' illustrated in FIG. 18. Step 580 may be performed as soon as steps 570 and 575 are complete; alternatively, the first and second images generated in steps 570 and 575 may be stored for later analysis in steps 580. That is to say, images stored at any time may be analyzed in step 580 independently from the acquisition of the images; in fact, images analyzed in step 580 may or may not have been acquired exactly as shown in steps 510 through 575. As part of step 580, an optional step 585 correlates the first and second image to find particles that are fluorescent in both images. Step 585 may include execution of the software instructions illustrated in FIGS. 28-30.

Although not shown in FIG. 12, automatic or manual focusing, or focus adjustments (e.g., based on measurements from a focus routine) may be performed before or in between any of the illuminating and imaging steps of method 500. For example, an autofocus routine may be performed by executing the software instructions illustrated in FIGS. 14-17, which may include convolution of images with kernel K illustrated in FIG. 18.

After step 575 or 580, method 500 optionally reverts to step 560 so that the cartridge moves to another measurement field to be counted, and steps 570 through 575 (and optionally step 580) are repeated. In an alternative embodiment, steps 560 and 570 may be performed for all fields of view prior to steps 560 and 575 being performed for all fields of view. If multiple fields of view are measured, when all such fields of view have been measured, an optional step 590 generates statistics from the particle counts generated in step 590.

II. Particle Counting Methods and Software

Figure 13:
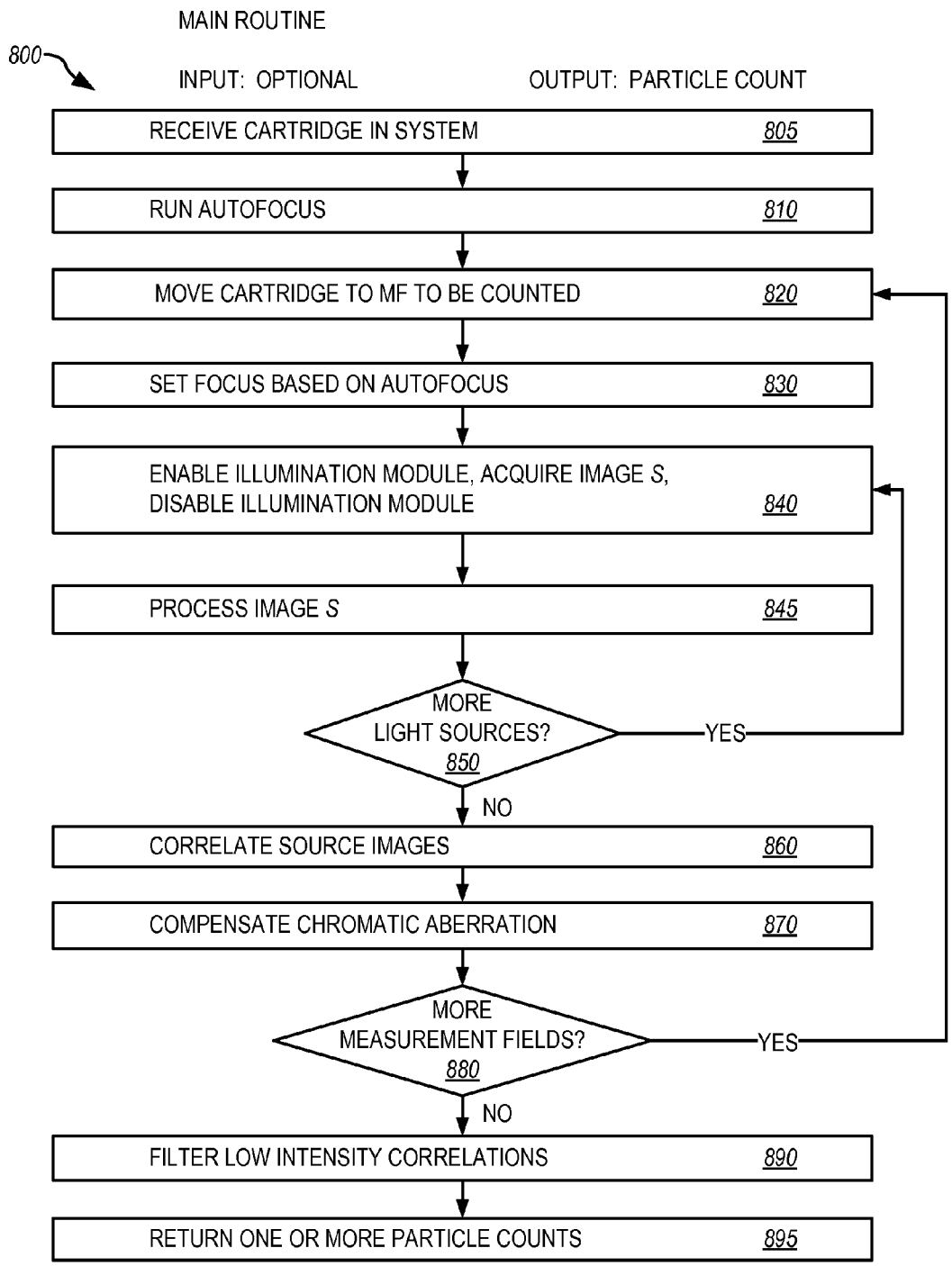
FIG. 13 is a flowchart of an exemplary method for gathering and processing data in a particle identification system, in an embodiment.

FIG. 13 is a flowchart of an exemplary method for gathering and processing data in a particle identification system. The illustrated method is called herein main routine 800, and may be performed by systems 100, 100' to provide a particle count for a sample within a cartridge (e.g., cartridges 130, 130', FIGS. 2 and 8, or cartridges 2600, 2600', 2600", FIGS. 45-50). "Routine" is used here in the sense of a computer program or subprogram (e.g., subroutine). In an embodiment, main routine 800 requires no data input and provides one or more particle counts or other measurements as output. In another embodiment, main routine 800 receives input data in the form of parameters related to the cartridge being utilized or what kinds of particles or other events are to be counted. Such input data may be in the form of information read from indicia located on the cartridge (e.g., as a barcode or 2D barcode) or may be manually entered into systems 100, 100'. The steps of main routine 800, and the subroutines performed therein, will be described in roughly the order that they are typically used; however, in embodiments certain steps may be performed in a different order or not at all. That is, no particular step of main routine 800 or the methods further detailed below is considered indispensable, some of these steps may be omitted for cost or time savings, possibly resulting in less accurate particle counts).

One exemplary feature of main routine 800 is that care is taken to establish precise focus of imaging optics 140 on measurement fields of cartridges 130, 130' for particle measurement by generating focus metrics related to the actual particles of a given sample, rather than by focusing on artifacts in the sample or on the cartridge. Therefore certain image processing steps will be initially discussed in relation to their support of autofocus routines, but as seen later the same steps will also be utilized for image processing for the particle counting. It should also be noted that various routines called by main routine 800 first identify "blobs" within images of the sample, then apply screens to the blobs to distinguish those blobs that likely represent particles of interest from those that do not. In this context, "blobs" are areas of local brightness within an image. The screens disclosed herein are described in order to enable one of ordinary skill in the related art to make and/or use particle identification systems, but not every screen mentioned is critical; certain of the screens may be performed in an order different from that specified here, or omitted, while other screens may be added. Generally speaking, the routines disclosed herein identify blobs or other events within at least one image of a measurement field that can be considered a superset of particles or events of interest, and determine fluorescently labeled particles or other events within the superset based on properties of the particles or events in the measurement field.

Step 805 of main routine 800 receives a cartridge into a system. An example of step 805 is systems 100, 100' receiving cartridges 130, 130', FIGS. 2, 8. Step 810 of main routine 800 runs an autofocus routine to establish appropriate focus adjustment of imaging optics on the cartridge. An example of step 810 is utilizing autofocus 900, FIG. 14, and its called subroutines to establish appropriate setting of focus mechanism 147 such that one or more measurement fields of cartridges 130, 130' are focused by imaging optics 140 on sensor 160. Step 820 of main routine 800 moves the cartridge to a measurement field to be counted. Step 830 sets focus of the imaging optics based on results of the autofocus routine. An example of step 830 is utilizing the results of autofocus 900 to control focus mechanism 147 to focus an image of cartridges 130, 130' on sensor 160 for the particular measurement field to be counted.

Step 840 of main routine 800 enables an illumination module, acquires an electronic image S, and disables the illumination module. A first example of step 840 is turning on illumination module 200 of systems 100, 100', acquiring an image S of a measurement field within cartridges 130, 130' from sensor 160 while illumination module 200 is on, then turning illumination module 200 off. Step 845 processes image S to identify and perform preliminary filtering on "blobs" identified within image S. As used herein, "blobs" are local areas of high intensity pixels within an electronic image. Such areas may or may not correspond to particles to be counted, many of the steps described in connection with FIGS. 19-30 are designed to help discriminate blobs that should be counted as particles of interest from those that should not. An example of step 845 is controller 450 performing process source image 1300, FIG. 19 (including its called subroutines). Step 845 involves only data processing as opposed to hardware manipulation, therefore step 845 may be performed within the sequence of main routine 800 as illustrated, or at any time after step 840 is performed. For example, main routine 800 may be repeatedly executed to generate multiple images S that can be saved in memory 470 for later processing. Also, images S can be transmitted from systems 100, 100' to a remote computer for processing (e.g., the remote computer is considered to form part of controller 450).

Step 850 makes a decision according to the number of illumination modules to be utilized for counting particles. If another image S and its associated processing are required, main routine 800 returns to step 840 to acquire another image S (and optionally process the image S in step 845). Accordingly, another example of step 840 is turning on illumination module 300, acquiring an image S while illumination module 300 is on, and turning illumination module 300 off. If images S associated with all appropriate illumination modules have been acquired, main routine 800 advances from step 850 to step 860.

Step 860 correlates images S that have been acquired using different illumination sources. An example of step 860 is performing correlate source images 2100, FIG. 28 (including its called subroutines). Step 870 compensates for chromatic aberration and other sources of misregistration of two or more images. An example of step 870 is performing compensate chromatic aberration 2200, FIGS. 29A-29B.

Step 880 makes a decision according to whether further measurement fields are to be measured. If so, main routine 800 returns to step 820. If not, main routine 800 proceeds to step 890.

Step 890 filters, based on intensity correlations out of the data taken in previous steps, if necessary, based on the data itself. In embodiments herein, it may be advantageous to combine data for multiple measurement fields before step 890 is performed, so that the data is statistically well behaved. However, in embodiments wherein the number of events found per measurement field is high, step 890 could be performed on data from a single measurement field, or on separate data sets from separate measurement fields before merging the data. This could be advantageous for cases where particle brightness changes significantly from one measurement field to the next, for example due to illumination intensity drift or fluorescence staining variation from one part of a sample to another.

Figure 30A:
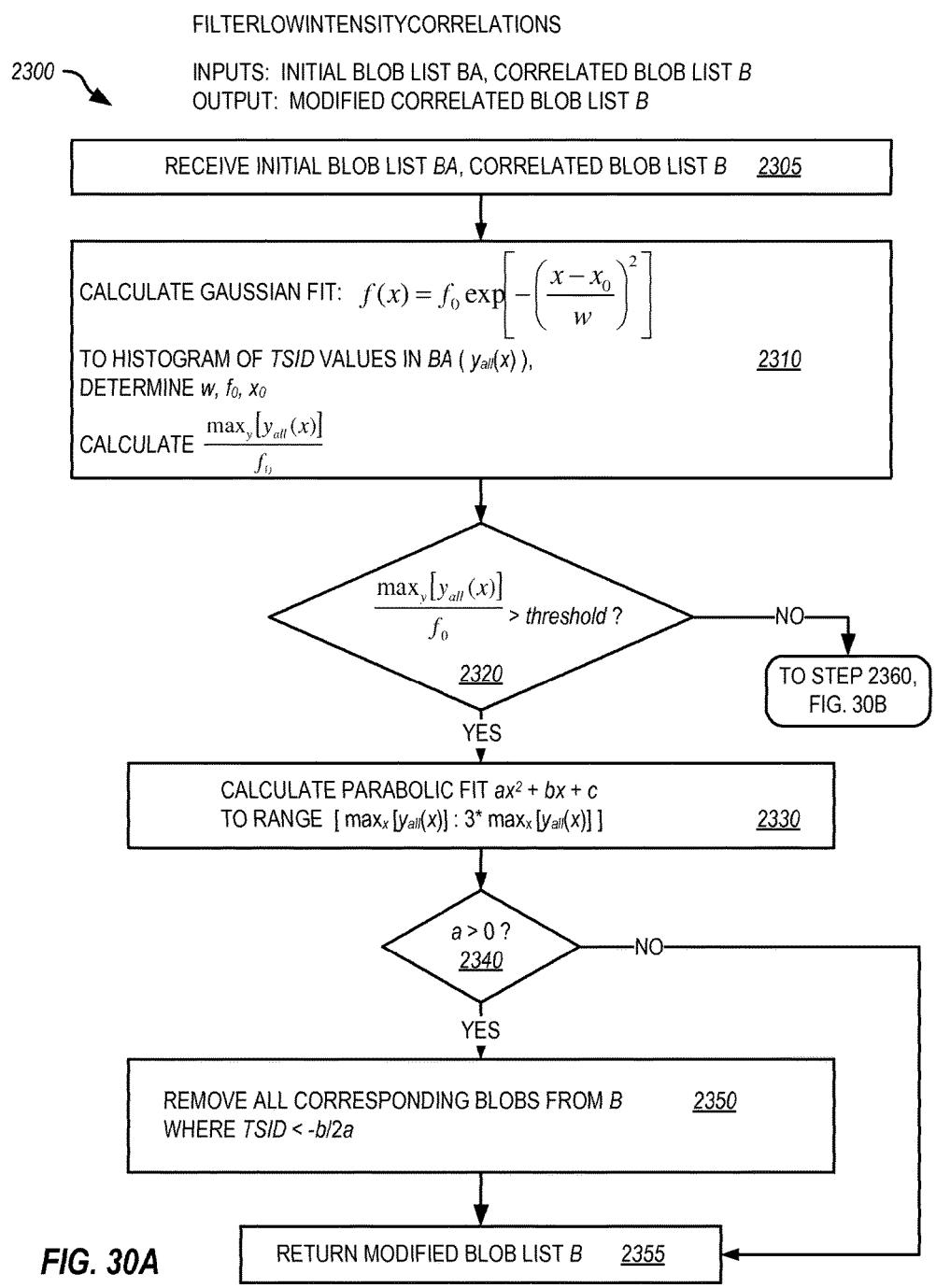
FIGS. 30A and 30B are flowcharts of a subroutine that filters blobs of a correlated blob list based on correlation of low intensity blobs to a main population of the blobs.
Figure 30B:
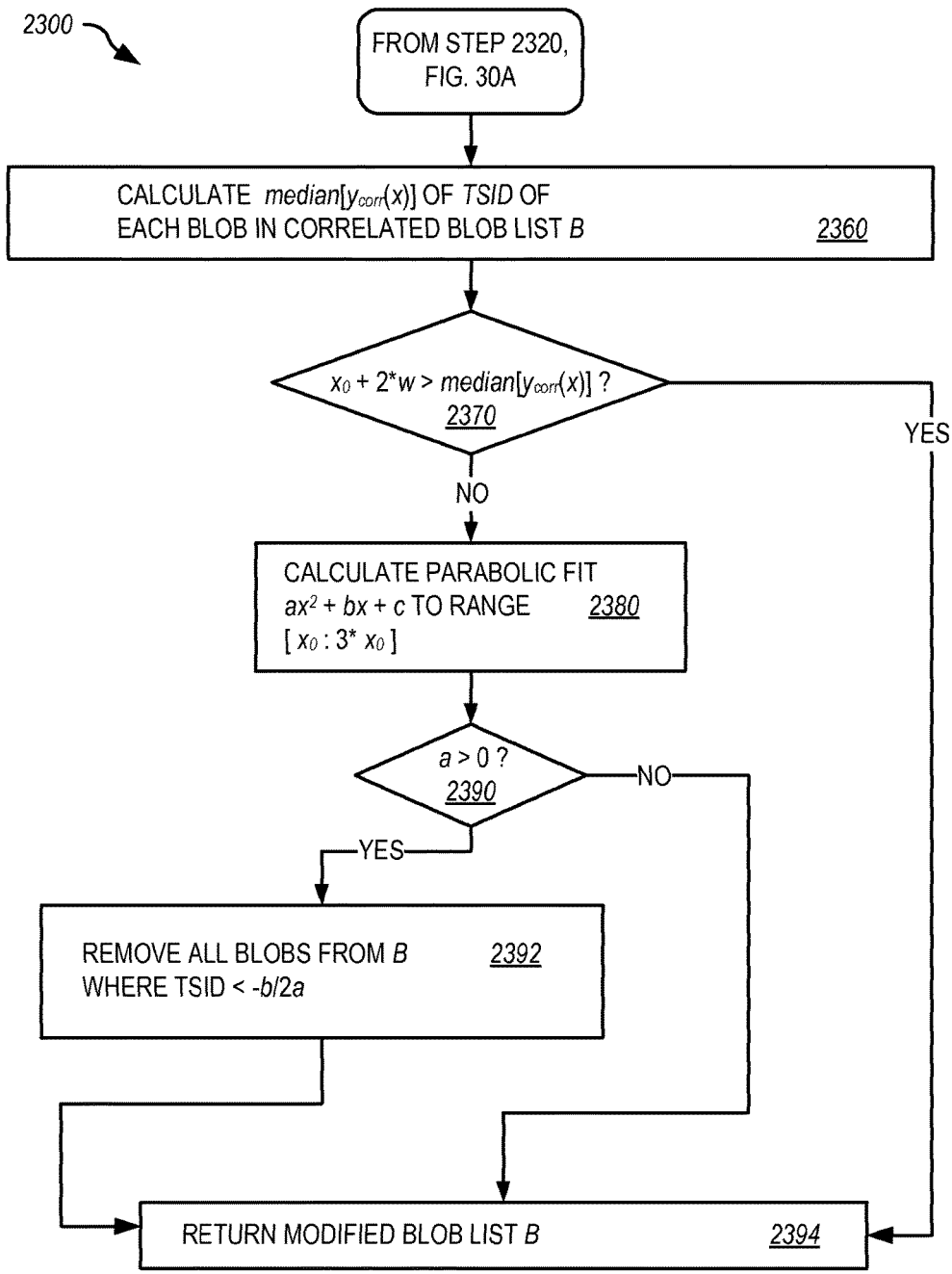

An example of step 890 is performing filter low intensity correlations 2300, FIGS. 30A-30B. A final step 895 of main routine 800 returns one or more particle counts. One example of step 895 is returning a single particle count from a single measurement field. Another example of step 895 is returning a set of particle counts from multiple measurement fields, and/or statistics derived therefrom.

Figure 14:
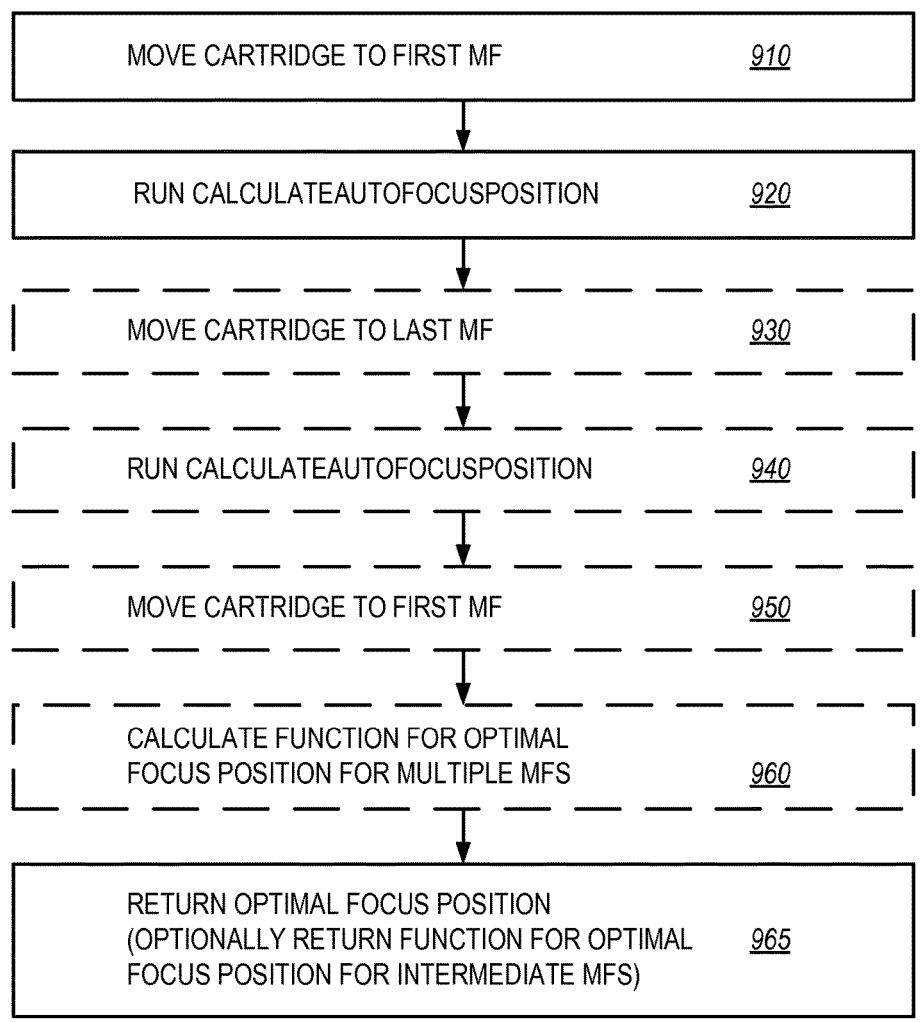
FIG. 14 is a flowchart of one exemplary autofocus method for optimizing optical focus of a particle identification system on a cartridge, in an embodiment.

FIG. 14 is a flowchart of one exemplary method called autofocus 900, for optimizing optical focus of a particle identification system on a cartridge. The illustrated method is called herein autofocus 900, and may be performed by systems 100, 100' to provide an optimal focus position for optics 140 relative to one or more measurement fields within a cartridge (e.g., cartridges 130, 130', FIGS. 2 and 8, or cartridges 2600, 2600', 2600", FIGS. 45-50). In an embodiment, autofocus 900 requires no data input and provides at least an optimal focus position for one measurement field within a cartridge as output. In another embodiment, autofocus 900 provides a function that identifies optimal focus position across multiple measurement fields of the cartridge as output. The function may for example be a linear ramp function that interpolates optimal focus settings between first and last measurement fields within the cartridge. Step 910 of autofocus 900 moves the cartridge to the first measurement field (herein, moving a cartridge "to a measurement field" should be understood to mean that the measurement field on the cartridge is positioned where imaging optics can image the measurement field). An example of step 910 is controller 450, 450' of systems 100, 100' (FIGS. 2, 6) controlling cartridge handling system 120 or 120' to move cartridge 130 or 130' to a first measurement field.

Step 920 of autofocus 900 runs a calculate autofocus position routine. An example of step 920 is running calculate autofocus position 1000, described below in connection with FIG. 15. Calculate autofocus position 1000 returns an optimal focus setting for at least one illumination module; it may also return an optimal focus setting for other illumination modules by adding offset(s) to the first optimal focus setting.

Steps 930 through 960 of autofocus 900 are optional. If performed, steps 930 through 960 provide measurements and calculate a function that provides optimal focus positions for multiple measurement fields on a cartridge. Step 930 moves the cartridge to a last measurement field. An example of step 930 is controller 450, 450' of systems 100, 100' (FIGS. 2, 6) controlling cartridge handling system 120 or 120' to move cartridges 130, 130' to a last measurement field. Step 940 runs the calculate autofocus position routine again. An example of step 940 is running calculate autofocus position 1000 again. Optional step 950 returns the cartridge to the first measurement field. An example of step 950 is controller 450, 450' of systems 100, 100' (FIGS. 2, 6) controlling cartridge handling system 120 or 120' to move a cartridge 130 or 130' back to the first measurement field. If steps 930 and 940 were performed, an optional step 960 calculates a function that provides optimal focus position for multiple measurement fields. An example of step 960 is calculating a linear ramp function that interpolates between optimal focus positions of the first and last measurement fields, to provide an optimal focus position for measurement fields that are between the first and last measurement field. Step 965 of autofocus 900 returns either a single optimal focus position, or a function that provides optimal focus positions for a plurality of measurement fields.

It should be understood that more measurement fields may be measured by adapting step 930 to move a cartridge to such measurement fields rather than a last measurement field, and that step 940 may be repeated. Doing so can provide information that allows optional step 960 to calculate functions for optimal focus that may be more accurate for intermediate fields than the linear ramp function discussed above.

Figure 15:
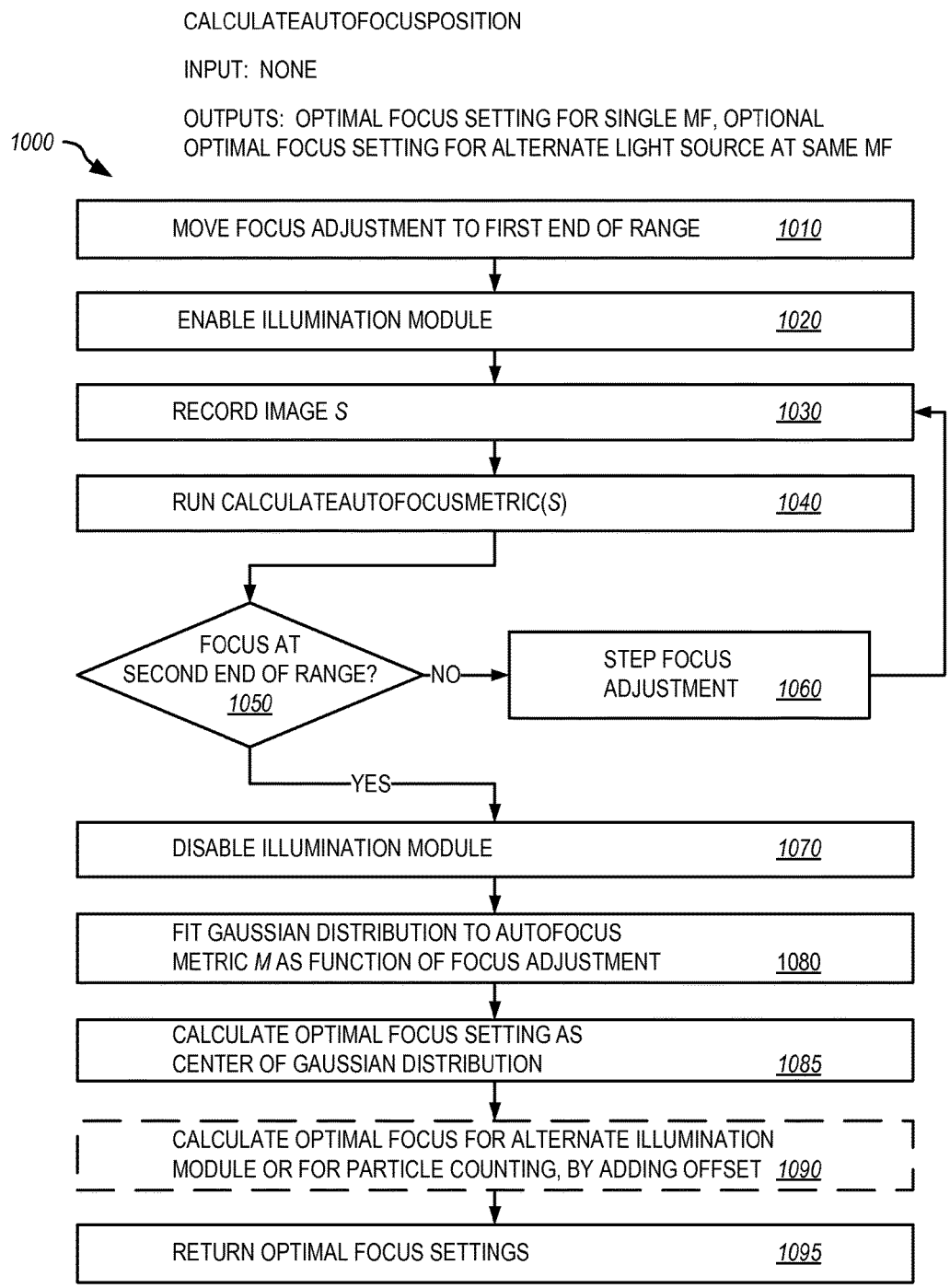
FIG. 15 is a flowchart of a subroutine for calculating autofocus position that may be utilized as part of the method of FIG. 14, in an embodiment.

FIG. 15 is a flowchart of a method called calculate autofocus position 1000 for generating an optical focus position of a particle identification system on a single measurement field of a cartridge. Calculate autofocus position 1000 may, for example, be performed by systems 100, 100' to provide an optimal focus position for optics 140 or 140' relative to one measurement field of a sample within a cartridge (e.g., cartridges 130, 130', FIGS. 1-5, or cartridges 2600, 2600', 2600", FIGS. 45-50). In an embodiment, calculate autofocus position 1000 provides an optimal focus position for one measurement field within a cartridge, for one illumination module, as output. In another embodiment, calculate autofocus position 1000 also provides optimal focus position (s) for the same measurement field, but for second or further illumination module(s), as output. Calculate autofocus position 1000 derives the optimal focus setting by analyzing images of the sample within the cartridge, rather than by analyzing images of the cartridge itself or images of other objects added to the sample. Specifically, calculate autofocus position 1000 analyzes images of a particle set that includes the particles to be counted, and other particles having the same focusing properties, using an analysis algorithm similar to that used to identify particles for counting. This ensures that the focus position found by calculate autofocus position 1000 is close to that optimal for counting particles of interest.

Calculate autofocus position 1000 requires no data input but begins when a measurement field of a cartridge is in position for imaging within a reader. Step 1010 of calculate autofocus position 1000 moves a focus adjustment to a first end of a range of focus adjustments. An example of step 1010 is controller 450 controlling focus mechanism 147 to move imaging optics 140 of systems 100, 100' to one end of its focus range. Step 1020 enables an illumination module to illuminate the measurement field. Step 1030 records an image S of the measurement field. Examples of steps 1020 and 1030 are controller 450 turning on illumination module 200 or 300 and recording an image S generated by sensor 160, FIG. 2. Step 1040 runs a calculate autofocus metric routine on image S (e.g., calculate autofocus metric 1100, FIG. 16). It is understood that step 1040 may be executed in the sequence shown, or may be postponed until steps 1050, 1060 and 1070 are performed. That is, calculate autofocus metric 1100 is a data analysis routine that can be performed either in real time with acquisition of images S, or later after the image acquisitions are complete. Step 1050 is a decision; if a second end of the range of focus adjustments has been reached, calculate autofocus position 1000 advances to step 1070. If the second end has not been reached, calculate autofocus position 1000 proceeds to step 1060, which steps focus adjustment to a position that is incrementally different from the previous focus adjustment, then returns to step 1030 to record another image S. An example of step 1060 is controller 450 controlling focus mechanism 147 to move imaging optics 140 of systems 100, 100' to an incrementally different position in its focus range.

Step 1070 of calculate autofocus position 1000 disables the illumination module that was enabled in step 1020. At this point, calculate autofocus position 1000 has at least gathered an image S at a plurality of focus positions; if steps 1040 corresponding to each image S have not been performed, they are now performed before proceeding to step 1080. Step 1080 fits a Gaussian distribution to the autofocus metrics returned from each instance of step 1040, with respect to the focus adjustment value associated with each such instance. Step 1085 calculates the optimal focus setting (for the illumination module enabled in step 1020) as the center focus setting with respect to the Gaussian distribution. In an alternative embodiment, steps 1080 and 1085 are replaced by a step in which the optimal focus position is set to be the recorded position with the optimal calculated autofocus metric.

An optional step 1090 of calculate autofocus position 1000 calculates optimal focus for an alternate illumination module, or for particle counting, by adding an offset to the optimal focus setting calculated in step 1085. The offset added in step 1090 may for example correct for chromatic aberration expected in optics (e.g., imaging optics 140) due to a wavelength change between two illumination modules. Also, as a practical matter, the offset added in step 1090 may correct for other effects. Such effects may include, for example, mechanical hysteresis or backlash in a focusing mechanism depending on the direction of movement of such mechanism. The offset may also be empirically derived between the optimal focus setting calculated in step 1085, and a focus setting that works ideally for particle counting purposes. For example, data may be obtained during calibration of systems 100, 100' that can be utilized to empirically derive such an offset. Step 1095 of calculate autofocus position 1000 thus returns at least the optimal focus setting calculated in step 1085, and may also return other optimal focus settings as calculated in step 1090.

Figure 16:
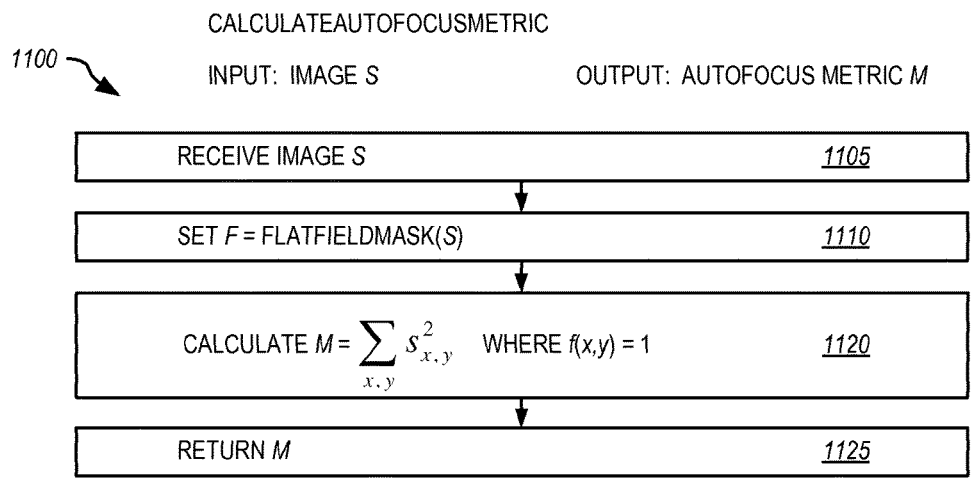
FIG. 16 is a flowchart of a subroutine for calculating a metric for evaluating autofocus quality, in an embodiment.

FIG. 16 is a flowchart of a method called calculate autofocus metric 1100 that provides a focus metric M for use by calculate autofocus position 1000 to optimize focus position, as discussed above. Calculate autofocus metric 1100 may, for example, be executed by processor 460 of systems 100, 100' to provide focus metric M for optics 140 relative to one measurement field of a sample within a cartridge (e.g., cartridges 130, 130', FIGS. 1-5, or cartridges 2600, 2600', 2600", FIGS. 45-50). Calculate autofocus metric 1100 derives focus metric M by analyzing images of the sample within the cartridge, rather than by analyzing images of the cartridge itself. However, it should be emphasized that calculate autofocus metric 1100 is but one way to derive a focus metric, and other ways of deriving a focus metric may be used in place of calculate autofocus metric 1100 in the context of step 1040 of calculate autofocus position 1000 described above.

Step 1105 of calculate autofocus metric 1100 receives an image S. Pixels of image S have values according to the light intensity received by a sensor at the corresponding location within the image. An example of step 1105 is receiving image S from calculate autofocus position 1000 (e.g., when step 1040 of calculate autofocus position 1000 initiates calculate autofocus metric 1100, as discussed above, it passes image S to calculate autofocus metric 1100). Step 1110 creates a processed pseudo image F from S by utilizing S as input for a flat field mask subroutine. An example of step 1110 is creating pseudo image F from S by performing flat field mask 1200, FIG. 17, discussed below. Flat field mask 1200 returns a binary image N wherein a pixel value of 1 corresponds with likelihood of the corresponding pixel of S belonging to a particle, and a pixel value of 0 corresponds with likelihood of the corresponding pixel of S not belonging to a particle.

At this point, it is noted that when this document discusses images and pixels thereof, the standard convention will be followed in which an upper case variable will be utilized for the image as a whole (e.g., S), and lower case variables will be utilized for pixels thereof (e.g., sx,y or s(x,y)). Also, certain techniques and parameters that are described in terms of pixels herein are appreciated as sensitive to distance in object space that a single pixel spans in image space. In this document, the term "image scale" is sometimes used as a reference to a distance in object space that maps to the size of one pixel in a detected image thereof. For example, if a system has an image scale of 2 μm/pixel, an object with a physical length of 10 μm will span 5 pixels in an image thereof.

Step 1120 calculates metric M by summing the square of each pixel of S that is associated with a pixel of F whose value is 1. That is, when f(x,y)=1, the corresponding s(x,y) is squared and added to the summation. This has the effect of increasing M when more pixels of S are identified as belonging to particles to be counted (as determined by flat field mask 1200, as discussed below). It also increases M when the pixels that are counted are bright (the corresponding values of s(x,y) are large) thereby favoring particles in focus. Step 1125 returns M for use by calculate autofocus position 1000.

Figure 17:
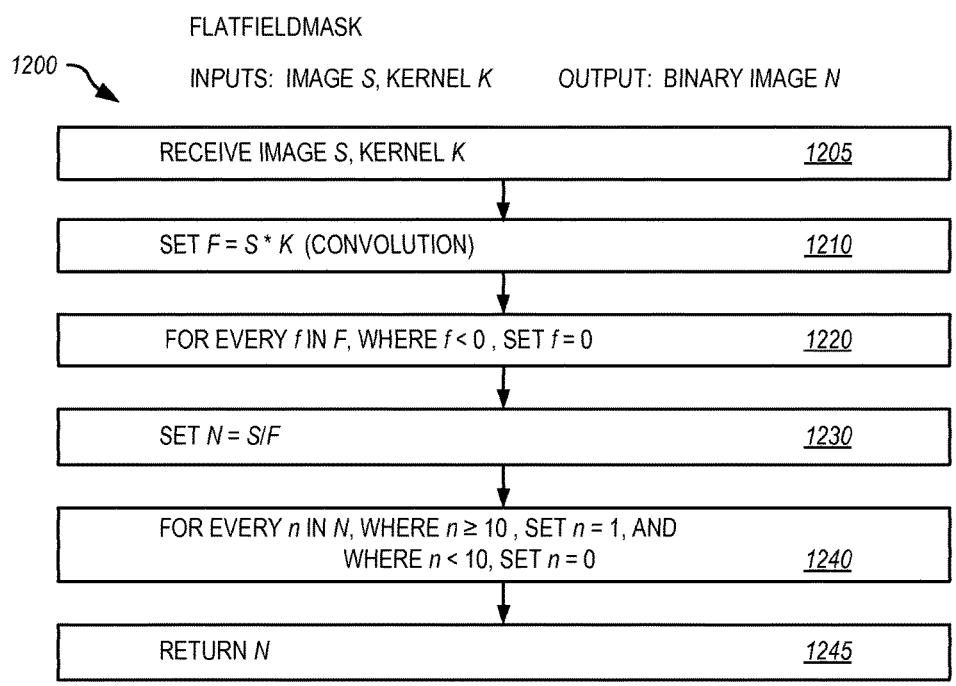
FIG. 17 is a flowchart of a flat field mask subroutine, in an embodiment.

FIG. 17 is a flowchart of a method called flat field mask 1200 that generates binary mask N for use by calculate autofocus metric 1100 and by process source image 1300, as described further below. Flat field mask 1200 may, for example, be performed by processor 460 of systems 100, 100' to provide binary mask N, received by calculate autofocus metric 1100 as F, for use therein. Flat field mask 1200 receives an image S as input and convolves the image with a filter kernel K to form a temporary pseudo image F that has zero or near-zero values for pixels that are likely associated with particles to be counted. Individual pixels are further enhanced in a temporary pseudo image N that divides each pixel s by the corresponding f. Finally, pseudo image N is thresholded to provide a final binary image N wherein pixel values of 1 correspond to image pixels that likely belong to a particle.

Step 1205 of flat field mask 1200 receives input image S and kernel K. Step 1210 creates a pseudo image F by convolving S with K. Filter kernel K is now discussed before completing the explanation of flat field mask 1200.

FIG. 18A depicts an exemplary kernel K for use in step 1210 of flat field mask 1200. It will be appreciated by one skilled in image processing that a convolution of kernel K with an image S having blobs of relatively high intensity against a relatively dark background will generate a pseudo image having negative values associated with pixels of the blobs, but likely positive values elsewhere. It should be noted that kernel K is set up in the expectation that the corresponding image has an image scale of about 2 μm/pixel and that the particles of interest are about 10 microns across; therefore the region of K having negative coefficients approximates a circle of diameter 5 pixels. Kernel K is composed of two contributions: a mean filter of radius 6 and an approximately Gaussian kernel based on the size of the cells to be detected. The mean filter component averages the image in an 11-pixel neighborhood and leads to a flat-field image centered around 1. The (negative) Gaussian component selectively identifies cell-sized features and results in large pixel values (the initial values of image N, as described below in connection with step 1230) for a flat-field image in the neighborhood of a cell. The relative strengths of the two components determines the amount of contrast that a cell must have relative to the background, to be detected. Both the absolute size of the kernel, (e.g., the number of pixels in the kernel) as well as the size scale, in pixels, of the Gaussian contribution to the kernel scale with the size of the particle of interest in pixels. Hence, the absolute size of the kernel, in pixels, and the size scale, in pixels, of the Gaussian contribution to the kernel scale with the physical size of the particle of interest and the image scale.

Exemplary kernel K shown in FIG. 18A is not normalized; the sum of the elements of K is equal to 25, such that convolution of an image with K will increase the net average values of pixels in the resulting image to increase. A normalized kernel K' shown in FIG. 18B could also be utilized; kernel K' corresponds to K wherein each element is divided by 25 such that the net average values of pixels in an image convoluted with K' remain the same (e.g., overall, the pixel values are multiplied by one).

Reverting to FIG. 17, after the convolution of S with K to form F, step 1220 of flat field mask 1200 sets each pixel f to zero when f is less than zero. Thus, given the exemplary K and image conditions discussed above, pixels likely associated with blobs will now have values of zero or near zero while other pixels will have positive values. Step 1230 generates a pseudo image N by dividing each pixel of S by the corresponding pixel of F. Because the blob pixels have values of zero or near zero, the corresponding pixels of N now have very large values, or values of infinity. Step 1240 modifies N by replacing any pixel n with a value of 10 or greater with 1, and any pixel n with a value of less than 10 with zero, to generate binary image N. It will be appreciated that utilizing 10 as the cutoff value for binary image N is not the only possible choice; other suitable cutoff values may be determined by reviewing pseudo images N that are created in step 1230. However, given the field values of K shown in FIG. 18, the flat-field image will have a value of approximately 1 in the absence of particles to be counted, so a cutoff value at least greater than 1 would be required. Step 1245 returns binary image N to the step that called flat field mask 1200.

Figure 19:
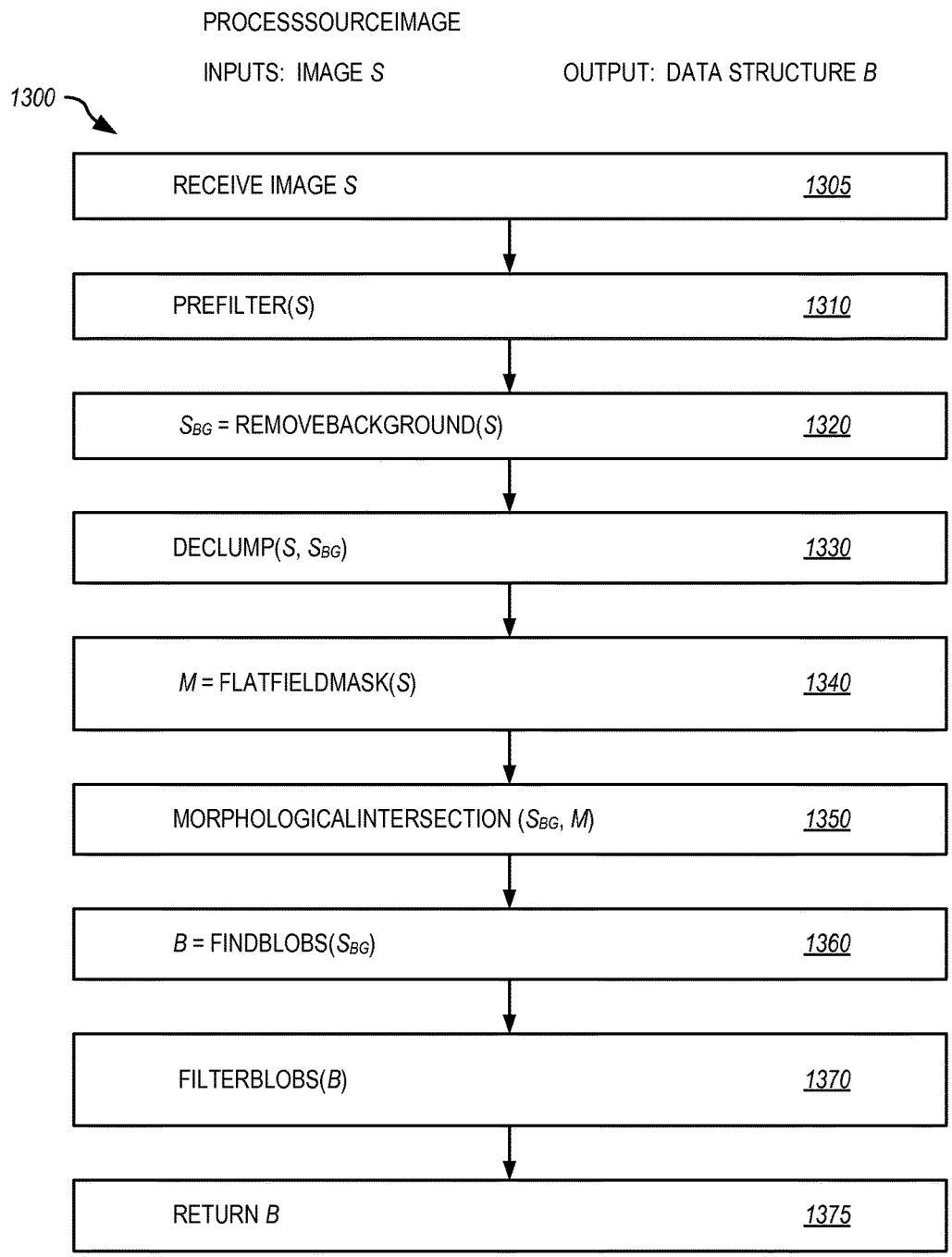
FIG. 19 is a flowchart of an exemplary method for processing a source image to identify particles within the image, in an embodiment.

FIG. 19 is a flowchart of an exemplary method called process source image 1300 for processing a source image to provide a data structure of particles within the image. Process source image 1300 may be performed, for example, by processor 460 of systems 100, 100', taking an image S as input that is generated by sensor 160 of a measurement field of a sample in a cartridge 130 or 130', and returning a data structure B of blobs identified in S. It should be emphasized that the steps listed in process source image 1300 form an exemplary embodiment that should enable one skilled in the art to practice at least the method specified, however certain steps thereof are optional and need not always be executed in the manner or order described. In particular, it should be evident that certain subroutines, individual steps and groups of steps may serve to increase accuracy of particle counting methods, but could be modified or omitted to simplify processing or reduce cost.

Step 1305 of process source image 1300 receives image S as input. Step 1310 calls a subroutine prefilter(S) that removes line noise, large scale features and electronic noise offsets in image S. An example of step 1310 is calling subroutine prefilter 1400, described below. Step 1320 calls a subroutine remove background(S) that generates a pseudo image SBG that subtracts local background both from background regions and neighboring regions. An example of step 1320 is calling subroutine remove background 1500, described below. Step 1330 calls a subroutine declump (S, SBG) that identifies connected regions within pseudo image SBG that may contain multiple particles to be counted, and splits the connected regions for further processing. An example of step 1330 is calling subroutine declump 1700, described below. Step 1340 generates a binary mask M by calling the flat field mask(S) subroutine described previously. An example of step 1340 is calling flat field mask 1200. Step 1350 calls a subroutine morphological intersection (SBG,M) that modifies pseudo image SBG by filtering connected regions of SBG where binary mask M is 0 within an entire region. An example of step 1350 is calling subroutine morphological intersection 1800, described below. Step 1360 generates a blob list B by using a subroutine find blobs (SBG) that identifies connected regions of bright pixels within pseudo image SBG. Blob list B labels the pixels to identify which regions they belong to. An example of step 1360 is calling subroutine find blobs 1900, described below. Step 1370 calls a subroutine filter blobs (B) that modifies blob list B by calculating various statistical moments on the blobs therein, and removing blobs that do not fit criteria for a desired particle count. An example of step 1370 is calling subroutine filter blobs 2000, described below. Step 1375 returns blob list B for further processing.

Figure 20:
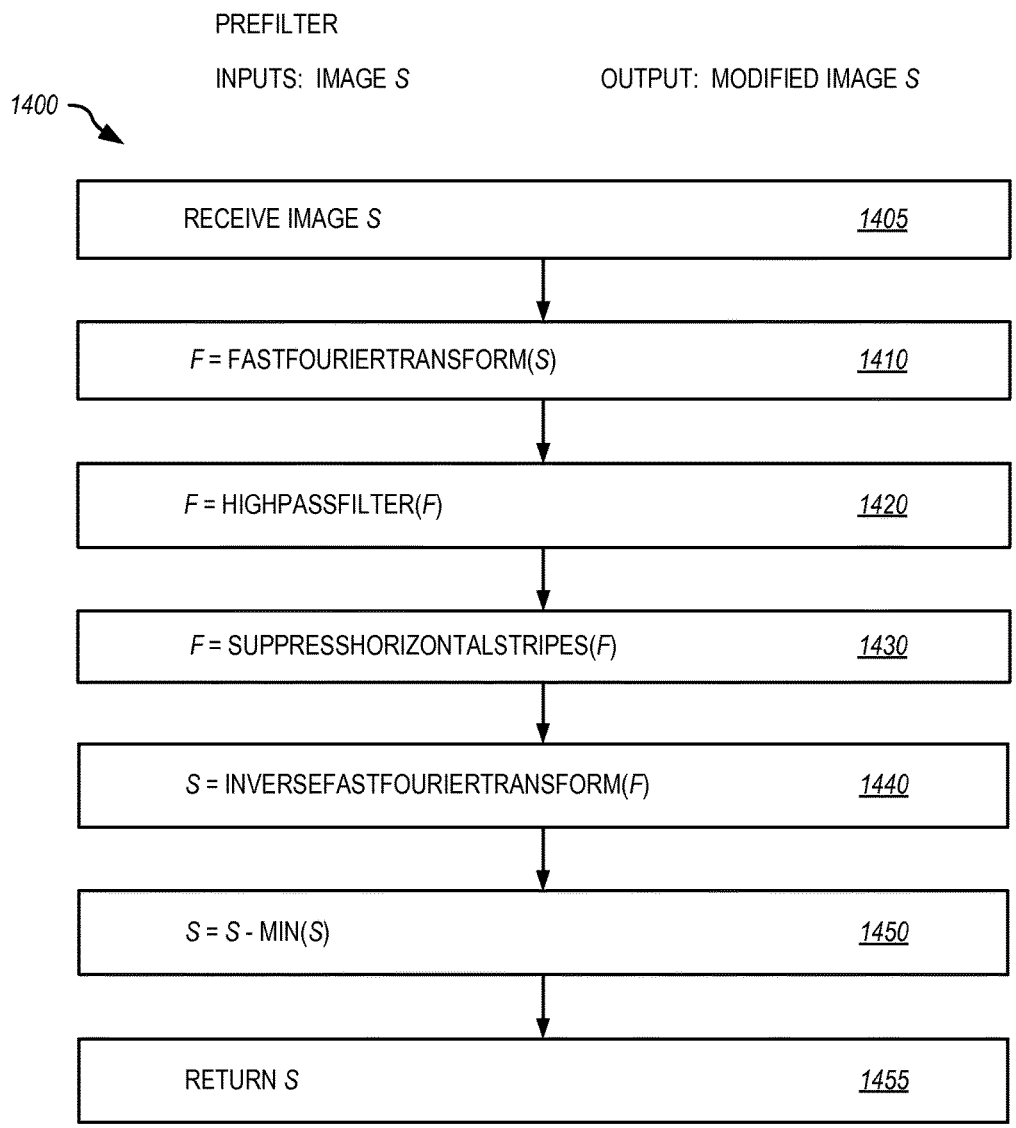
FIG. 20 is a flowchart of an exemplary method for prefiltering a source image to facilitate detection of particles therein, in an embodiment.

FIG. 20 is a flowchart of an exemplary subroutine prefilter(S) 1400 that removes line noise, large scale features and electronic noise offsets in image S. Prefilter 1400 may be performed, for example, by processor 460 of systems 100, 100', taking an image S as input that is generated by sensor 160 of a measurement field of a sample in a cartridge 130 or 130', and returning a modified image S. It is appreciated that the steps listed for prefilter 1400 are exemplary only, and that certain of these steps may be omitted for cost savings or to reduce processing complexity, with possible impact on particle count accuracy.

Step 1405 of prefilter 1400 receives image S as input. Step 1410 generates a temporary pseudo image F as a fast Fourier transform of image S, the fast Fourier transform (and its inverse) being known in the art. Step 1420 performs a high pass filtering operation on pseudo image F by removing, in the frequency domain, low frequency content that corresponds to features larger than 100 pixels in the spatial domain. This removes image content that is too large to be considered as a particle for counting; it is expedient to do this operation in the frequency domain because of the difficulty in assessing large objects in the spatial domain against a background of small objects. Also, it is understood that the present method desires to count particles on the order of 10 μm in size with an image scale of 2 μm/pixel; the low frequency content removed in step 1420 would be adjusted accordingly to screen out unreasonably large image content if smaller or larger particles were to be counted. Step 1430 sets frequency components along ky=0 to zero except at kx=0; that is, any DC component that exists at ky=kx=0 is maintained. Step 1430 therefore advantageously suppresses line-patterned dark noise that is often introduced by CMOS image sensors. Step 1440 creates a new version of image S by performing an inverse fast Fourier transform on F as modified by steps 1420 and 1430. Step 1450 determines the minimum value within S and subtracts this value from each pixel in S. Step 1455 of prefilter 1400 returns the modified image S.

Figure 21:
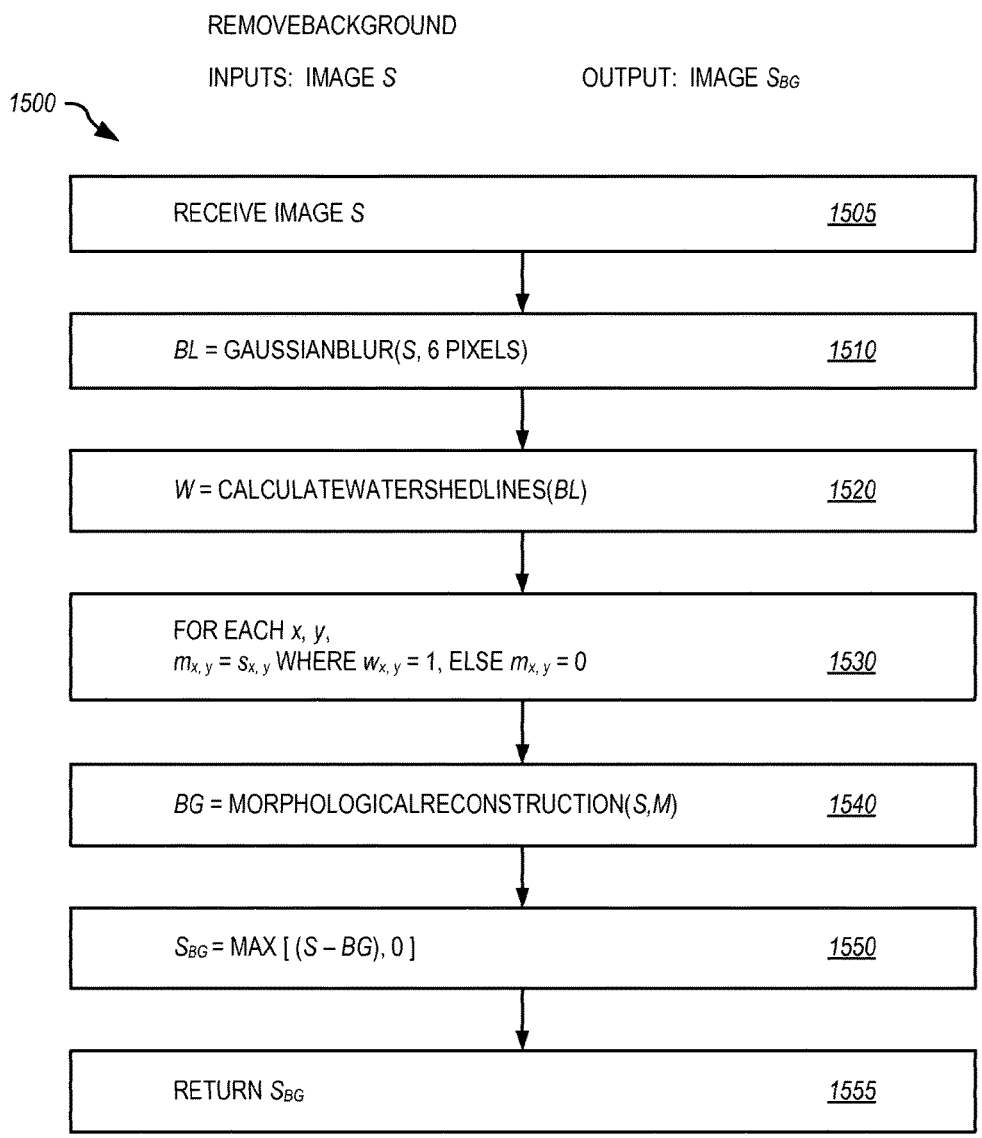
FIG. 21 is a flowchart of an exemplary method for establishing watershed lines between blobs in an image, and removing background from the image, in an embodiment.

FIG. 21 is a flowchart of an exemplary subroutine remove background(S) 1500 that generates a pseudo image SBG by subtracting local background both from background regions and neighboring regions. Remove background 1500 may be performed, for example, by processor 460 of systems 100, 100', taking an image S as input that is generated by sensor 160 of a measurement field of a sample in a cartridge 130 or 130', or as prefiltered by prefilter 1400, and returning a pseudo image SBG.

The purpose of remove background 1500 is to calculate the local background in the area of each particle to be counted. The principle of the routine is to determine the dimmest separation lines between areas of local brightness, and then define the local background for each area of local brightness as the maximum pixel value on the separation lines forming a perimeter therearound. The dimmest separation lines between areas of local brightness are equivalent to inverted watershed lines. A global image processing method is utilized to determine a maximum value of the separation line's perimeter around each area of local brightness. This method flood fills a pseudo image of the areas of local brightness up to the maximum value for the separation line perimeter around areas of local brightness. Alternatively, each perimeter contour may be traced out individually. Because local maxima may be introduced by noise, remove background 1500 blurs a temporary copy of the image to suppress such maxima for watershed line identification purposes. Also, in determining the local background, it is desirable to treat clumped cells as a single object (thus remove background 1500 is performed before declump 1700, described below).

Step 1505 of remove background 1500 receives image S as input. Step 1510 creates a pseudo image BL by applying a six-pixel radius Gaussian blur to image S. The radius of the Gaussian blur is chosen as 6 pixels because the present method desires to count particles on the order of 10 μm in size in images with a scale of 2 microns per pixel; it is understood that the Gaussian blur radius should be modified when particles that are significantly smaller or larger are to be counted or if a different image scale applies.

Also, it should be understood that in this case and in other cases herein, a Gaussian blur of radius r pixels is applied by convolving an image with a filter kernel containing values representative of a 2-dimensional Gaussian distribution of radius r pixels. For computational ease, the kernel may be truncated to consist only of the pixels that have significant values, e.g., a kernel of [r pixels]×[r pixels] may be used in the case of a Gaussian width of r pixels. Furthermore, the kernel may be normalized such that it integrates to 1, such that the effect of applying the blur is only to smooth the image, rather than scale it by increasing or decreasing the net intensity of its pixels.

In step 1510, the purpose of the Gaussian blur is to avoid erroneous watershed lines through the interior of a particle of interest due to short-scale pixel intensity variation within the perimeter of the particle. Such intensity variation can arise from, e.g., camera noise, light scattering artifacts, biological properties of the particle of interest, and the presence of other sample components within the same region of the image. The radius of the Gaussian blur is set to approximately match the size of the particle of interest, and will thus change with the physical size of the particle of interest, and with image scale. This covers characteristic scales for short-scale interior intensity variation. If only certain known characteristic scales are present, the radius of the blur applied in step 1510 can be adjusted accordingly to be a closer match to the greater of the scales present. In cases where interior intensity variation of particles of interest is already smooth, step 1510 can be eliminated altogether. Empirical optimization may be utilized to set the radius of the blur applied in step 1510.

Step 1520 creates a binary image W by calling a subroutine calculate watershed lines (BL), described below as calculate watershed lines 1600. Step 1530 creates a still further pseudo image M that depends on the values of S and the value of binary image W for a corresponding pixel therein. In step 1530, for each pixel coordinate (x, y), mx,y is set to the corresponding value sx,y when wx,y=1, otherwise mx,y is set to 0 (that is, mx,y=0 when wx,y=0).

Step 1540 of remove background 1500 creates a background image BG by calling a subroutine morphological reconstruction (S,M), described below as morphological reconstruction 1650. Step 1550 creates an output image SBG by taking the maximum value of (S-BG) and 0 for each pixel location in S and BG, that is, all negative values are converted to 0. Step 1555 returns SBG.

Figure 22:
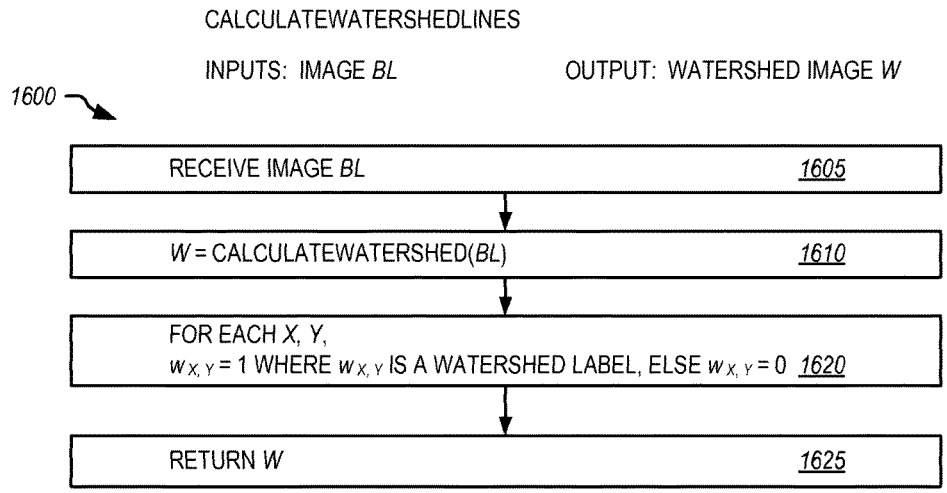
FIG. 22 is a flowchart of a subroutine for providing watershed lines in a watershed image, based on an input image, in an embodiment.

FIG. 22 is a flowchart of an exemplary subroutine calculate watershed lines (BL) 1600 that generates a binary "watershed" image. Calculate watershed lines (BL) 1600 may be performed, for example, by processor 460 of systems 100, 100', taking an image BL as input that is processed from an image S generated by sensor 160 of a measurement field of a sample in a cartridge 130 or 130', or as prefiltered by prefilter 1400 and possibly smoothed by step 1510 in remove background 1500.

Step 1605 of calculate watershed lines 1600 receives an image BL as input (e.g., image BL as generated at step 1510 of remove background 1500, described above, or image BL as generated at step 1710 of declump 1700, described further below). Step 1610 generates a pseudo image W from image BL by calculating a watershed as described in "Watersheds in Digital Spaces: An Efficient Algorithm Based on Immersion Simulations" [Vincent (1991)]. In Vincent, an input image is segmented into watersheds, or catchment basins, surrounding local maxima and labeled by the catchment basin that each pixel belongs to. A "watershed" label is sometimes inserted into the image to separate the catchment basins (by the description above, it may be seen that the separation lines are more analogous to separations between watersheds, than watersheds themselves). Step 1610 always separates adjacent basins by applying the watershed label (that is, Vincent's routine is modified to always apply the label, rather than applying it only sometimes). Step 1620 modifies pseudo image W to create a binary image by converting all of the watershed labels to pixel values of 1, and all other pixels to 0. Step 1625 returns binary image W.

Figure 23:
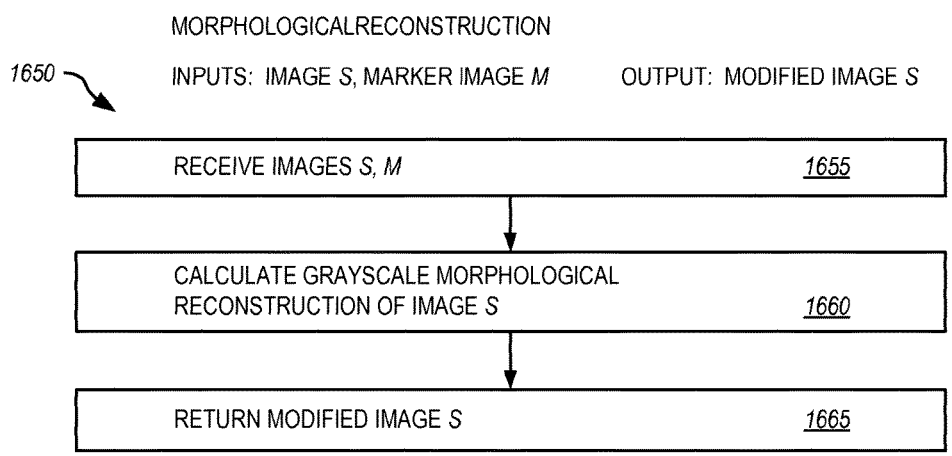
FIG. 23 is a flowchart of a subroutine for morphological reconstruction of an input image, in an embodiment.

FIG. 23 is a flowchart of an exemplary subroutine morphological reconstruction (S,M) 1650 that calculates a grayscale morphological reconstruction of an input image. Morphological reconstruction 1650 may be performed, for example, by processor 460 of systems 100, 100', taking an image S and a marker image M as input (image S may be generated by sensor 160 of a measurement field of a sample in a cartridge 130 or 130', or as prefiltered by prefilter 1400, while marker image M is a processed pseudo image generated, for instance, by step 1340 in process source image 1300).

Step 1655 of morphological reconstruction 1650 receives images S and M as input (e.g., image S as generated by sensor 160 or as prefiltered by prefilter 1400, and M as generated at step 1530 of remove background 1500, described above). Step 1660 returns a grayscale morphological reconstruction as described in "Morphological Grayscale Reconstruction in Image Analysis: Applications and Efficient Algorithms" [Vincent (1993)]. Step 1665 returns modified image S.

Figure 24:
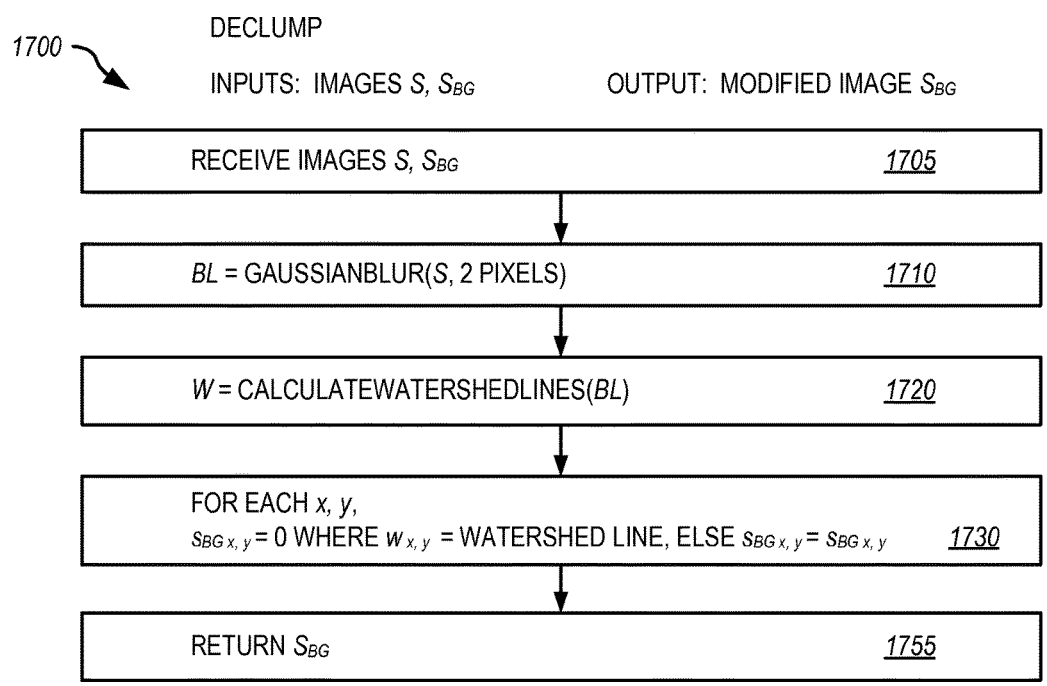
FIG. 24 is a flowchart of a subroutine for declumping a background image based on a second image, in an embodiment.

FIG. 24 is a flowchart of an exemplary subroutine declump (S,SBG) 1700 that separates multiple particles to be counted into separate image regions. Declump 1700 may be performed, for example, by processor 460 of systems 100, 100', taking images S, SBG as input (image S may be generated by sensor 160 of a measurement field of a sample in a cartridge 130 or 130', or as prefiltered by prefilter 1400, while image SBG is a processed pseudo image with local background subtracted out, e.g., as generated by remove background 1500).

Step 1705 of declump 1700 receives images S and SBG as input (e.g., image S as generated by sensor 160 or as prefiltered by prefilter 1400, and SBG as generated at step 1320 of process source image 1300, described above). Step 1710 generates a pseudo image BL by applying a Gaussian blur to image S. The radius of the blur applied in step 1710 is typically two to three pixels, and is set to suppress noise within a single particle in order to avoid splitting the particle into multiple particles, and without introducing any possibility of blurring out a watershed line between two particles. That is, this blurring step suppresses short-scale intensity variation within the perimeter of a particle of interest. Causes for such intensity variation have been discussed above in connection with FIG. 21, step 1510. In the case of step 1710, the blurring further serves to avoid watershed lines in between two or more particles that are sufficiently close to each other that the pixel intensities do not reach the true background level in regions located between the particles. The value for the radius of the Gaussian scales with the image scale. Since this routine also serves to keep together very close-lying particles, the radius value also depends on the apparent sharpness of the particles in the image. The sharpness is affected by, e.g., optical aberrations, pixel resolution, sensor electronics performance, light transmission properties of the sample and cartridge materials through which imaging is performed, and inherent light emission profile of the particle.

Step 1720 generates a binary image W by passing BL to subroutine calculate watershed lines 1600, discussed above. Step 1730 modifies SBG by leaving each pixel sBGx,y undisturbed except for pixels where W indicates a watershed line, in which case the corresponding pixel sBGx,y is set to 0. Step 1755 returns modified image SBG.

Figure 25:
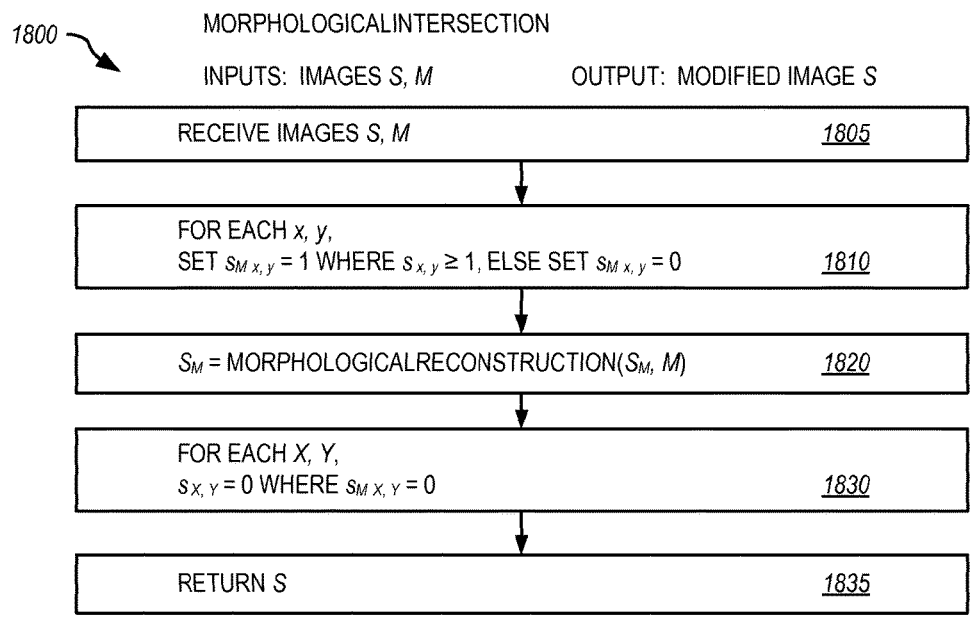
FIG. 25 is a flowchart of a subroutine for morphological intersection of an image with a marker image, in an embodiment.

FIG. 25 is a flowchart of an exemplary subroutine morphological intersection (SBG,M) 1800 that filters connected regions of input pseudo image SBG where input marker file M is zero within an entire region. Morphological intersection 1800 may be performed, for example, by processor 460 of systems 100, 100', taking images S and M as input (image S may be, for example, a processed pseudo image while marker file M may be a file coded to separate regions of interest from regions not of interest).

Step 1805 of morphological reconstruction 1650 receives images S and M as input (e.g., image SBG as generated at steps 1320 and 1330 of process source image 1300, and marker file M as generated at step 1340 of process source image 1300, as described above). Step 1810 creates a temporary binary image SM wherein for each pixel coordinate x,y, sM x,y is set to a value of 1 where s x, y has a value of at least 1, otherwise sM x, y is set to a value of 0. Step 1820 calls morphological reconstruction 1650 to calculate a grayscale morphological reconstruction of image SM utilizing marker file M. Step 1830 modifies input file S by setting each pixel s x,y to 0 where sM x, y already has a value of zero. Step 1835 returns modified image S.

Figure 26:
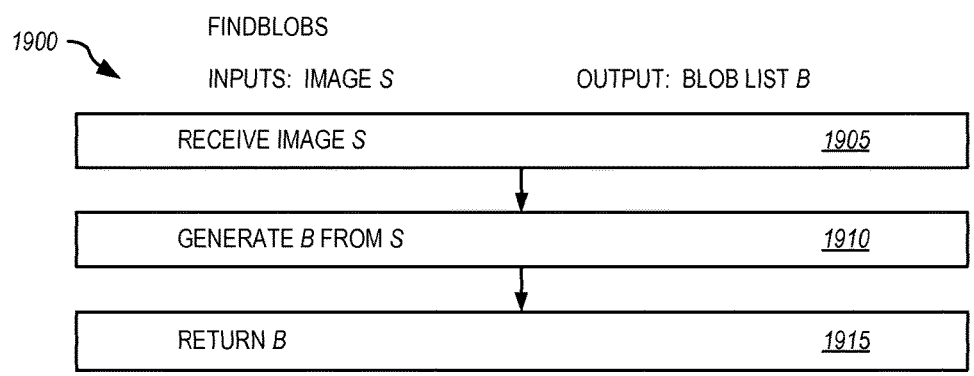
FIG. 26 is a flowchart of a subroutine that creates a list of blobs identified within an image, in an embodiment.

FIG. 26 is a flowchart of an exemplary subroutine find blobs(S) 1900 that creates a blob list B of data structures that include a label for each connected region in S and the coordinates of nonzero pixels in S that belong to each of the connected regions. Find blobs 1900 may be performed, for example, by processor 460 of systems 100, 100', taking an image S as input (image S may be, for example, a processed pseudo image).

Step 1905 of find blobs 1900 receives image S as input (e.g., image SBG as generated at step 1350 of process source image 1300, as described above). Step 1910 generates blob list B utilizing a blob extraction such as is known in the art and is generally called connected-component labeling.

Connected-component labeling consists of identifying connected regions of foreground pixels. In the present embodiment, a foreground pixel in image SBG is a pixel of value 0 while pixels of value 1, i.e. watershed lines, are background pixels. The connected-component labeling method serves to assign a unique label to each region of connected foreground pixels, i.e., blobs. In the present embodiment, connected-component labeling has been implemented as follows. A label counter and an empty queue are initialized, and a row-major scan is performed on image SBG. If an unlabeled foreground pixel is encountered, the label value is incremented and the pixel is added to the queue. This operation initiates a subroutine that serves to identify all pixels belonging to a connected region. In the subroutine, the first pixel in the queue is assigned the current label value. This pixel is then removed from the queue, and all its unlabeled foreground neighbor pixels are added to the queue ("neighbor pixels" herein are the 8 pixels closest to the pixel of interest, known from graph theory as 8-connectivity). This repeats until the queue is empty, at which point the current label value has been assigned to all pixels belonging to this connected region, and the process exits the subroutine. The scan continues to search for the next unlabeled foreground pixel, which will lead to the identification of another connected region. The scan ends when all pixels in SBG have been scanned.

Connected-component labeling can thus be described by the following pseudocode in Fortran-style:

```
FOR each foreground pixel in image SBG (following row-major scan)
    IF pixel is unlabeled
        Increment label counter
        Add foreground pixel to queue
        WHILE queue not empty
            Assign label to first pixel in queue
            FOR all foreground neighbor pixels
                IF pixel unlabeled
                    Add pixel to queue
                ENDIF
            ENDFOR
            Remove pixel from queue
        ENDWHILE
    ENDIF
ENDFOR
```

After step 1910 is complete, step 1915 returns blob list B.

Figure 27A:
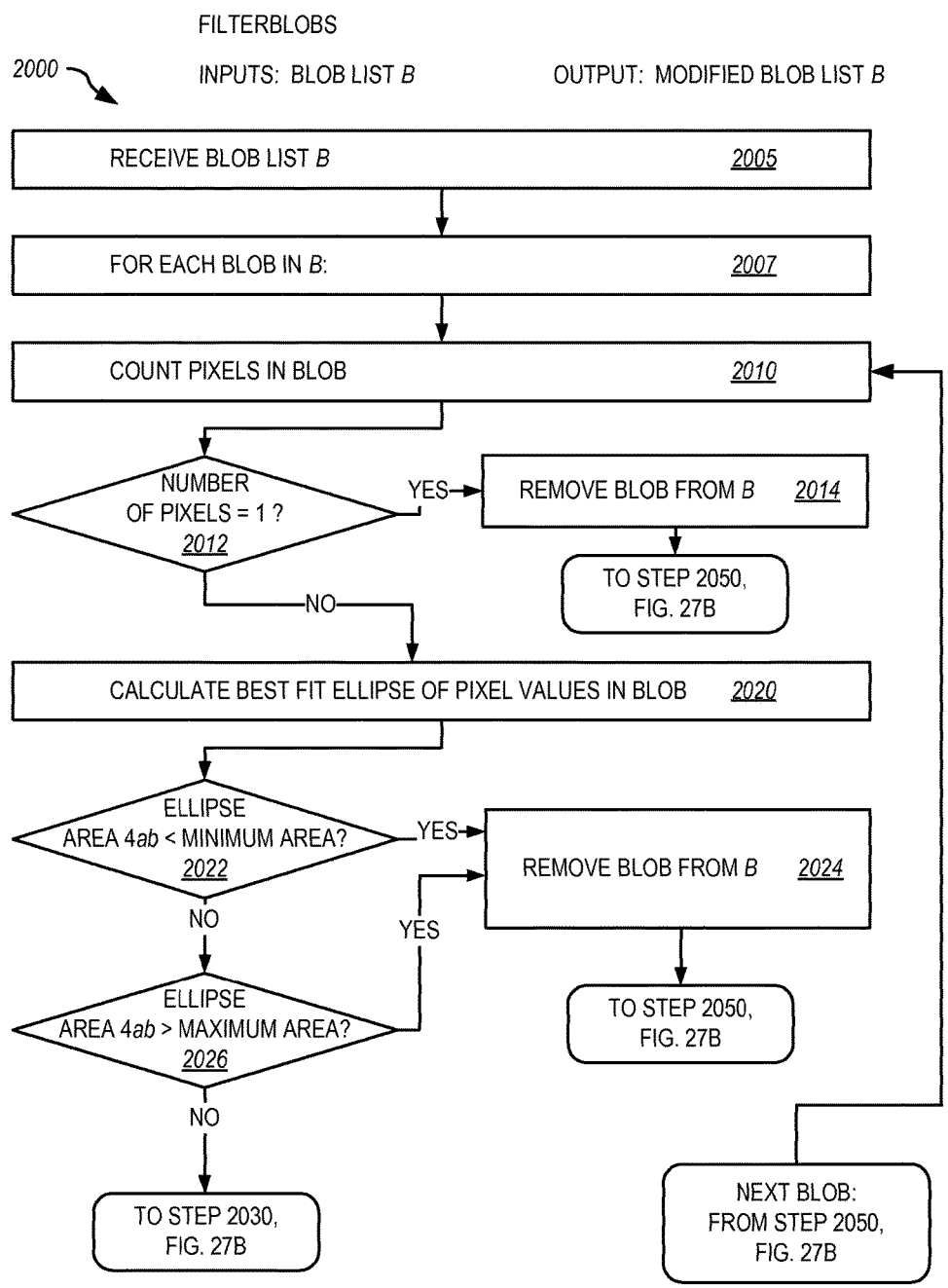
FIGS. 27A through 27C are flowcharts of a subroutine that filters a list of detected blobs to provide a modified list of blobs, in an embodiment.
Figure 27B:
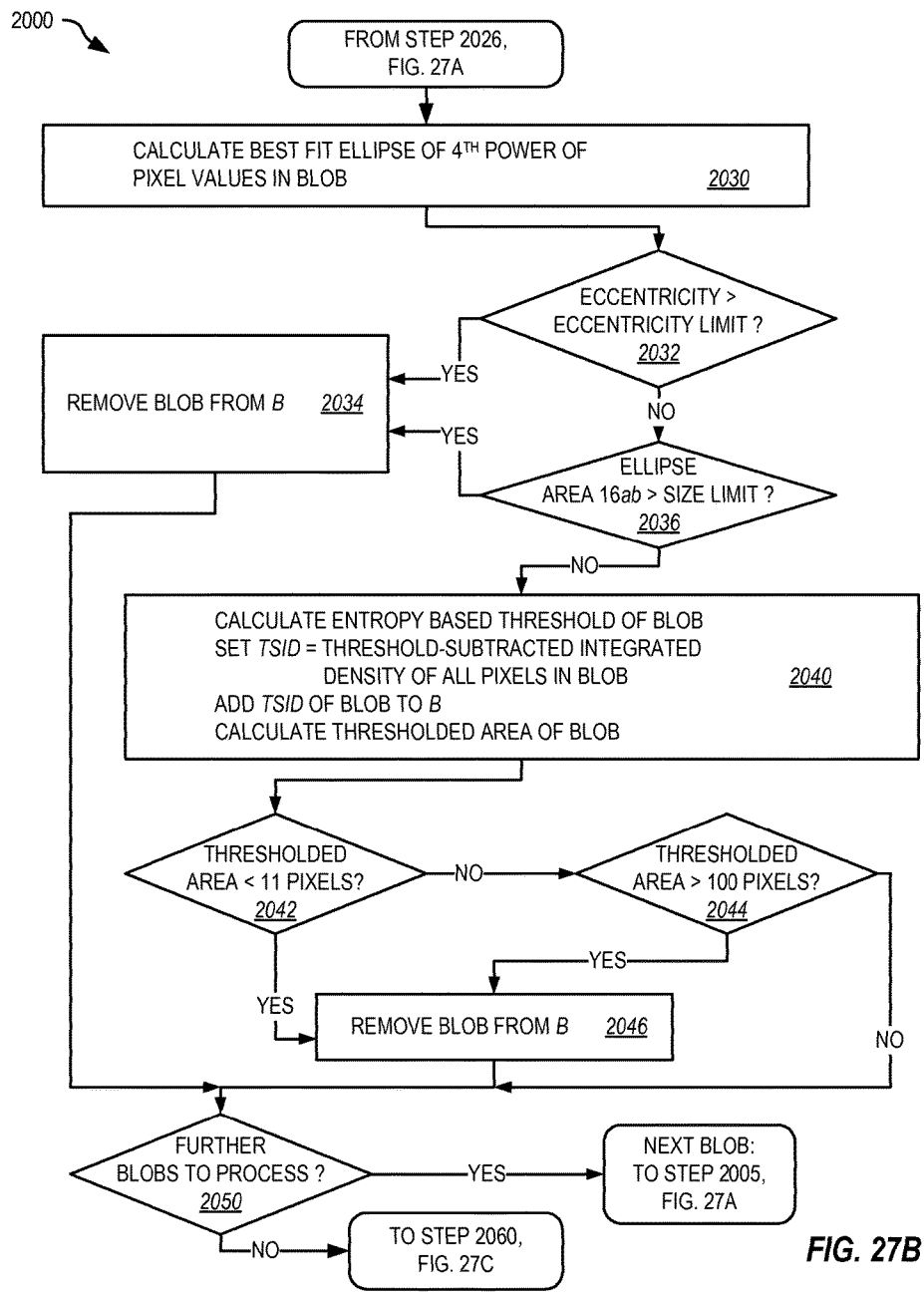
Figure 27C:
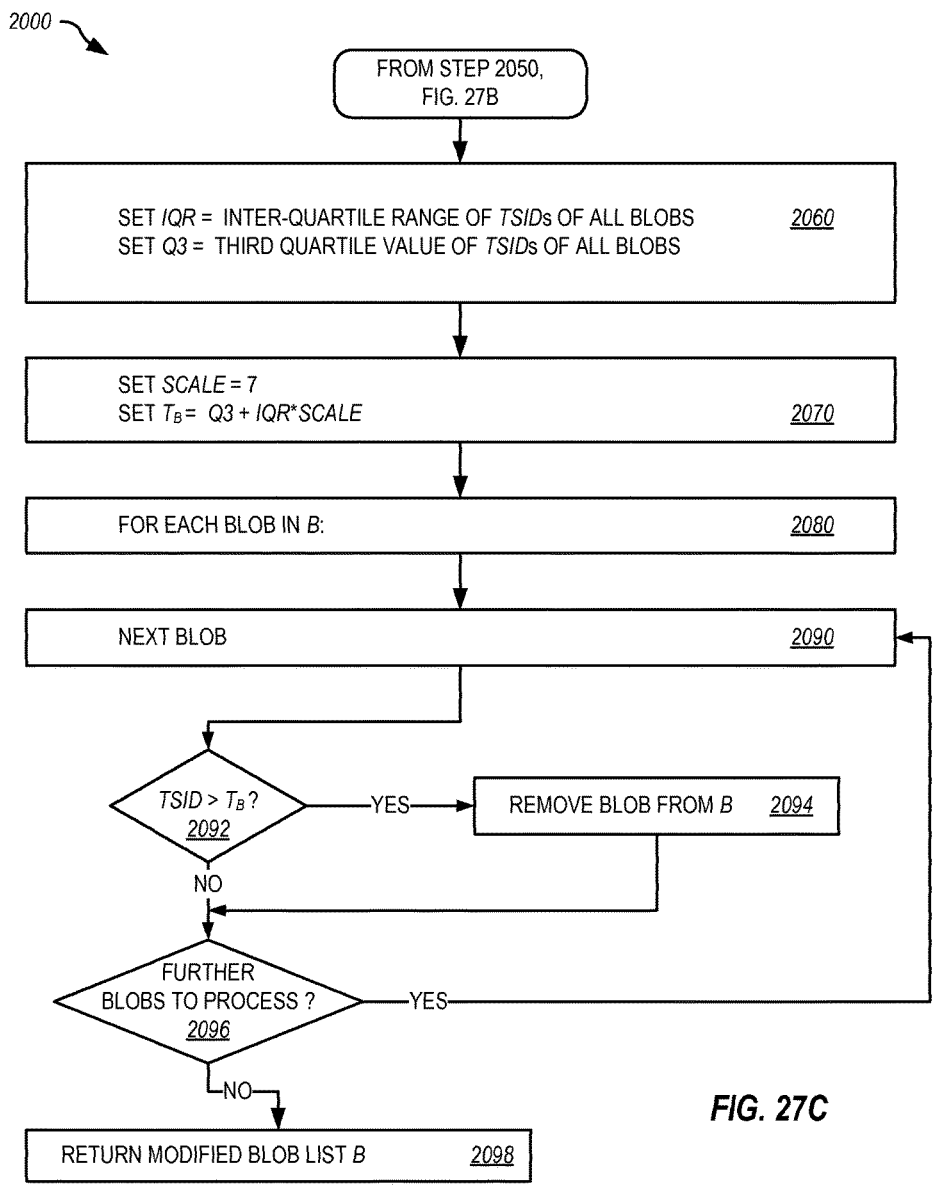

FIGS. 27A through 27C are flowcharts of an exemplary subroutine filter blobs (B) 2000 that filters blob list B of data structures that include a label for each connected region in S and the coordinates of nonzero pixels in S that belong to each of the connected regions. Filter blobs 2000 may be performed, for example, by processor 460 of systems 100, 100', taking blob list B as input.

Generally speaking, filter blobs 2000 applies moment-of-inertia type statistical measures to filter out blobs that do not behave as the particles intended to be counted. A number of the specific values used as screens may be set by considering the size of particles intended to be counted, and by analyzing images of samples and adjusting the values to include particles and exclude artifacts appropriately. The specific embodiment shown in FIGS. 27A through 27C applies to images with a scale of 2 microns per pixel and particles of interest with a diameter of about 10 microns. Meaningfulness of many of these tests is also enhanced by subtracting the background (e.g., as done in remove background 1500, described above) or by utilizing threshold-subtracted integrated density, or TSID, on a blob by blob basis, as discussed below. One skilled in the art will see that the successive screens of filter blobs 2000 are applied to the input blob list to remove blobs that are considered inappropriate as candidates for particle counting; however these screens are exemplary only and presented in an exemplary order. Therefore, these screens may be rearranged in order, or even deleted for cost savings or to reduce processing complexity. None of the particular screens described is considered essential.

Step 2005 of filter blobs 2000 receives blob list B as input (e.g., blob list B as generated at step 1910 of find blobs 1900, as described above). Step 2007 initiates a loop that increments through each blob in blob list B. Step 2010 counts the pixels in the blob. This filtering step is to remove artifact blobs that arise from "hot" (unduly sensitive) sensor pixels. Step 2012 determines whether the number of pixels is equal to 1 (and because of the rationale underlying steps 2012 and 2014, the value of 1 is appropriate for any pixelated system and will not scale with image scale or particle size). If so, step 2014 removes the blob from B and filter blobs 2000 advances to step 2050. If not, filter blobs 2000 advances to step 2020.

Step 2020 calculates a best fit ellipse of pixel values in the blob; that is, step 2020 calculates major and mirror axes a and b of the best fit ellipse. It should be noted that a and b are not limited to integer values, as the blob may be small and/or oriented at an angle with respect to horizontal and vertical axes of the imager. The intent of this screen is to remove blobs caused by residual hot pixels (e.g., hot pixels combined with other background effects), clumped hot pixels, and very small events caused by background effects.

Step 2022 determines whether the area defined by 4ab is less than a minimum area. For a system with image scale of 2 µm/pixel, the minimum area may be about 2 pixels. Unless clumping of hot pixels is the only source of small, false events, the minimum area scales with the image scale. This value depends on the density of hot pixels, as a high density of hot pixels would increase the probability of clumping of multiple hot pixels, in which case the cut would likely have to be increased beyond 2 pixels. The minimum area also depends on the size of the particles of interest as well as the size and relative frequency of smaller, false events. The size histograms for particles of interest and small, false events may or may not overlap. In either case, the cut should be placed to average a net zero error in the count of particles of interest. If the particles of interest are significantly larger than about 5 pixels, the minimum area can be increased to improve the rejection of background artifacts, including smaller particles not of interest. If any short-scale background features are present in addition to hot pixels, the performance will likely be degraded if the cut should be reduced, in which case step 2022 could be removed. The minimum area also depends on the typical size scale of background features. If the typical size scale of background features is closer to the size of the particles of interest and the relative frequency of such background features is significant, it may be difficult to achieve satisfactory performance. In that case, it may be advantageous or necessary to improve the image resolution by, for instance, decreasing the image scale or utilizing a higher-performance imaging system.

If the ellipse area 4ab is less than the minimum area, step 2024 removes the blob from B and filter blobs 2000 advances to step 2050. If not, filter blobs 2000 advances to step 2026.

Step 2026 determines whether the area defined by 4ab from step 2020 is greater than a maximum area that may be, for example, 100 pixels. This screen is set up to conservatively remove events that are much larger than particles of interest, and may be increased to about 100 since other area filters applied in steps 2036 and steps 2044, discussed below, also serve to remove events larger than the particles of interest. The purpose here is to make the best cut in a histogram where a true population and a false population may exist. In the present case, the false events are larger than the true events. The maximum area may therefore scale with the image scale and the size of the particles of interest. In systems where the occurrence of large, false events is relatively rare, no significant performance changes may be expected by varying the maximum area over a wide range.

If the ellipse area 4ab is greater than the maximum area, step 2024 removes the blob from B and filter blobs 2000 advances to step 2050. If not, filter blobs 2000 advances to step 2030.

The ellipse fit performed in step 2020 can be biased by long "tails" associated with certain blobs. The area limits in decision steps 2022 and 2026 above are accordingly loose so that valid particles are not filtered out. A further filtering step compensates for this by utilizing a similar technique based on the 4th power of pixel intensities. Step 2030 calculates a best fit ellipse of the 4th power of pixel values in the blob; that is, step 2020 calculates major and mirror axes a and b of the best fit ellipse formed by the 4th power of the pixel values. The eccentricity of this ellipse is defined as sqrt(1−(b/a)2). Blobs in images may have outlying regions of lower intensity caused by image or imaging artifacts. For instance, local background variation at or very close to a particle may not be distinguished from the actual particle. Hence, a blob may include an intensity contribution from local background in addition to the intensity contribution from the particle. Particle movement during at least a portion of the image exposure, caused for instance by general sample motion, may produce an additional lower intensity contribution to the blob. Such an effect may also be caused by mechanical motion of the cartridge or of one or more imaging system components. Likewise, aberrations in the imaging system can produce, e.g., uniform blur, directional tails of lower intensity, and halos, all of which may be included in a blob. When determining the shape and size of a particle, it is advantageous to reduce or eliminate the contribution from artificial outlying regions of lower intensity. This can be achieved, for instance, by raising the pixel intensities to a greater power, which reduces the weight of lower intensity pixels. In an embodiment, the pixels values are raised to the 4th power. For other systems with different image or imaging properties, a different power may be optimal. If the images are free of artificial, outlying regions of lower intensity, raw pixel values may be used. When CD4+ T-helper cells are the particles of interest, the eccentricity based screen removes events that are clearly too eccentric to originate from an approximately circular particle (e.g., a CD4+ T-helper cell).

Step 2032 removes events that are clearly too eccentric to originate from an approximately circular particle. The applicability of the calculated eccentricity is highly dependent on resolution of the imaging system. In an embodiment where a particle of interest has a diameter of only about 5 pixels, the eccentricity limit has to be relatively loose, such as 0.8.

In a system with improved resolution relative to the particle size, the eccentricity limit can be made tighter (lower). The eccentricity limit depends on the types of artifacts present in the image. The optimal eccentricity limit is the value that, on average, leads to a net zero error in particle count. In an embodiment, a cut value in the range 0.75-0.85 has been found to be optimal.

Therefore, in an embodiment, step 2032 determines whether the eccentricity of the ellipse exceeds 0.8. If so, step 2034 removes the blob from B and filter blobs 2000 advances to step 2050. If not, filter blobs 2000 advances to step 2036. The eccentricity based screen is dependent on resolution of the imaging system utilized (e.g., sensor 160's rendition of an image that is magnified by optics 140). In an embodiment wherein particles to be counted have a diameter of only about 5 pixels, a cutoff value used for an eccentricity screen must be loose (e.g., a range of 0.75 to 0.9) wherein if resolution of an imaging system was such that a typical particle to be counted had a larger diameter, a tighter (lower) limit could be utilized.

Step 2036 determines whether the area defined by 16ab is greater than a size limit. Step 2036 removes events that are clearly too large to be a particle of interest, but because more refined screen of particle size is performed following this step (steps 2040 to 2046, discussed below) the size limit is set conservatively loose. The screen implemented in step 2036 does, however, improve the quality of the input data to, and therefore the performance of, the procedure that follows in steps 2040 to 2046. In an embodiment, a size limit of approximately 50 has been found to work well. Due to the presence of a more refined size selection procedure following this step, the size limit value is not critical. The value of the size limit scales with the image scale and the size of the particles of interest.

Therefore, in an embodiment, step 2036 determines whether the area defined by 16ab is greater than 50 pixels. If so, step 2034 removes the blob from B and filter blobs 2000 advances to step 2050. If not, filter blobs 2000 advances to step 2040.

An entropy based threshold can be utilized to remove residual background associated with each blob such that legitimate particles will still be counted but artifacts can be screened out. The intent of the following steps is to create the best estimate of particle size and to craft limits around the size to account for natural variation of the particles, noise, resolution effects, and optical blurring.

Step 2040 first calculates an entropy based threshold utilizing the "Kapur, Sahoo, and Wong Method" described in the paper, "A Survey of Thresholding Techniques" by P. K. Sahoo, S. Soltani and A. K. C. Wong, published in Computer Vision, Graphics, and Image Processing 41, at page 237. However, instead of applying the entropy based threshold globally as in this paper, the threshold is applied locally on an individual blob basis. Generally speaking, this method defines the probabilities of original gray level distributions as pi where i is a particular grayscale value out of 1 possible levels in a grayscale range G (e.g., an integer within the range of 0 to 1-1) and a variable Pt as $$P_t = \sum_{i=0}^{t} p_i$$

for a given threshold candidate t. Further variables $H_b(t)$ and $H_w(t)$ are calculated as $$H_b(t) = -\sum_{i=0}^{t} \frac{p_i}{P_t} \log_e\left(\frac{p_i}{P_t}\right)$$

and $$H_w(t) = -\sum_{i=t+1}^{l} \frac{p_i}{1-P_t} \log_e\left(\frac{p_i}{1-P_t}\right).$$

Finally, an optimal threshold t* is calculated as the gray level that maximizes $H_b(t)+H_w(t)$, that is, $$t^* = \text{ArgMax}\{H_b(t)+H_w(t)\} \text{ for } t \in G.$$

Step 2040 also calculates a number called TSID as the threshold-subtracted integrated density of all pixels in the blob being processed, adds the TSID to the data structure of the corresponding blob in blob list B, and calculates the thresholded area of the blob.

Step 2042 determines whether the thresholded area is less than 11 pixels. If so, step 2046 removes the blob from blob list B and filter blobs 2000 advances to step 2050. If not, filter blobs 2000 advances to step 2044. Step 2044 determines whether the thresholded area is greater than 100 pixels. If so, step 2046 removes the blob from blob list B and filter blobs 2000 advances to step 2050. If not, filter blobs 2000 advances to step 2050 without removing the blob. Both the lower area limit used in step 2042 and the upper limit used in step 2044 depend on particle size, natural variation, noise, resolution effects, and optical blurring. That is, the best estimate of the actual particle area is provided by step 2040. The previous filtering on particle size has improved the data that is input to other steps in the process, or has reduced processing time by removing events that clearly are not associated with particles of interest. The lower area limit used in step 2042 and the upper limit used in step 2044 represent the size range of the particles of interest with an additional tolerance to account for imperfections due to, e.g., noise, limited resolution, and blur. The lower area limit used in step 2042 and the upper limit used in step 2044 scale with the image scale and the size of the particles of interest.

Step 2050 determines whether all blobs have been processed through the filters of filter blobs 2000 discussed above. If not, filter blobs returns to step 2005 to process the next blob in B. If all blobs have been processed, filter blobs continues to step 2060.

Step 2060 sets a variable IQR to the inter-quartile range of all TSIDs of blobs in blob list B, and a variable Q3 to the third quartile value of all TSIDs of blobs in blob list B. Step 2070 sets a scaling factor SCALE to 7, and a bright object threshold TB to Q3+IQR*SCALE. SCALE is an empirically determined parameter that may lie within the range of about 3 to 8. TB is approximately where the top value of the TSID distribution would have been, based on the bulk of the blob population, except for abnormally bright objects such as inclusions skewing the top end of the distribution. Thus, the loop defined by steps 2080 through 2094 filters a histogram of blob brightness. Images may contain multiple different classes of particles, each characterized by a typical blob brightness range. If the ranges are distinct or only partially overlap, it may be possible to separate the individual populations by making simple cuts in the histogram. In cases of overlap, TB may be set to minimize the number of blobs assigned to the wrong population. For example, in an embodiment the histogram contains the primary population, containing the particles of interest, and a class of extremely bright outliers. The overlap is statistically insignificant and TB can be placed using a simple inter-quartile approach. In this embodiment, the value of TB can be in the range from 4 to 8 and especially 7. In other embodiments with statistically significant overlap between populations, a narrower range may be required. Also, in some cases, more refined methods such as peak fitting may be applied to correctly assign blobs to individual populations.

Step 2080 initiates a loop that covers each blob in B. The next blob in B is considered in step 2090. A decision step 2092 determines whether TSID of the current blob exceeds TB. If so, step 2094 removes the blob from B. If not, and/or after step 2094, a decision step 2096 determines whether further blobs remain in B to be processed. If so, filter blobs 2000 returns to step 2090 for the next blob. If not, step 2098 returns the modified blob list B.

Figure 28A:
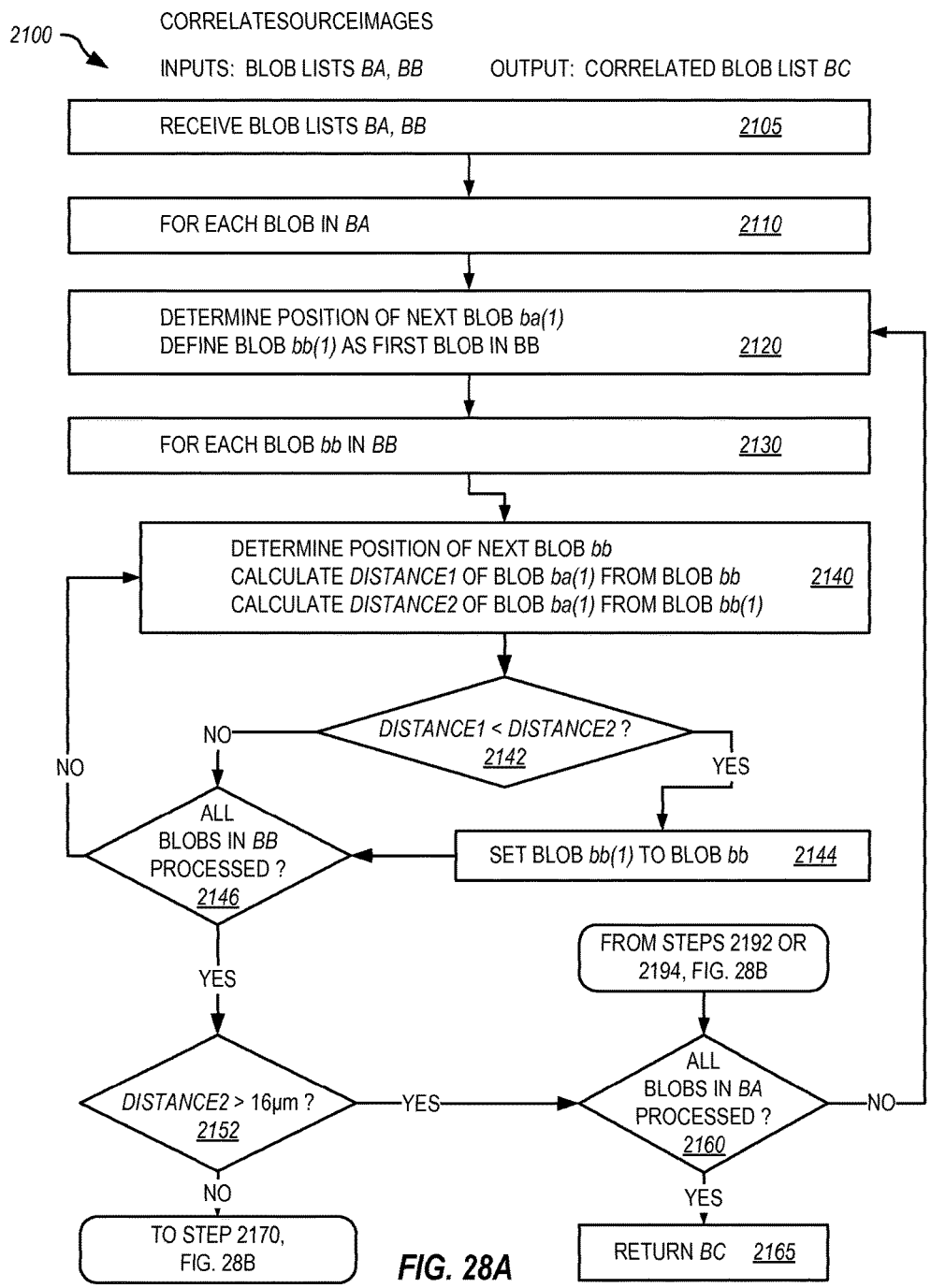
FIGS. 28 and 28B are flowcharts of a subroutine that correlates source images from two lists of blobs to create a correlated list of blobs, in an embodiment.
Figure 28B:
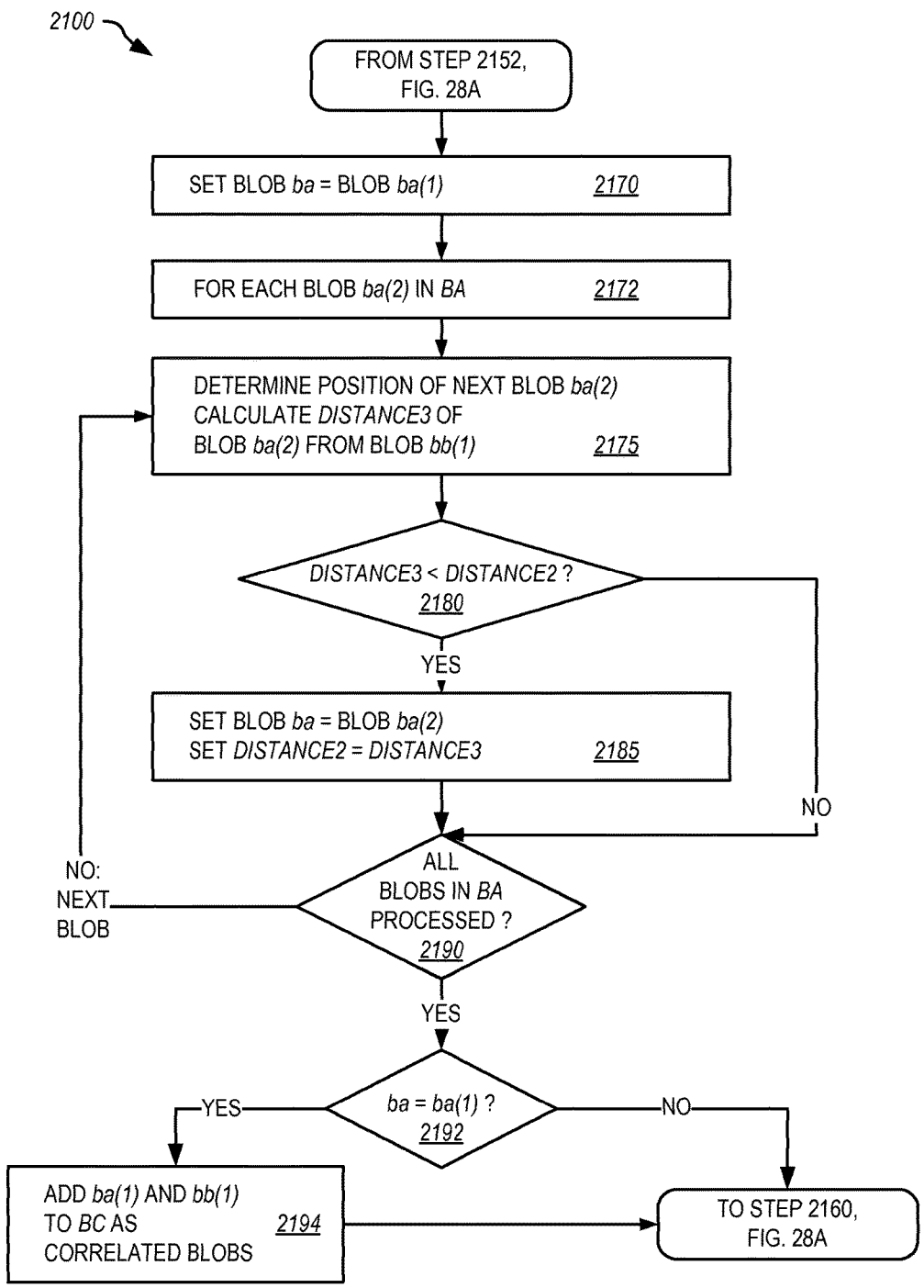

FIGS. 28A and 28B are flowcharts of an exemplary subroutine correlate source images (BA, BB) 2100 that takes blob lists BA, BB as input and generates a blob list BC of data structures that include only blobs that are spatially correlated to one another. Correlate source images 2100 may be performed, for example, by processor 460 of systems 100, 100', taking blob lists BA, BB that were generated from a given measurement field, utilizing two different illumination modules, as input. Generally speaking, correlate source images 2100 identifies objects that are within a fixed distance from each other, and identifies the "best" match of such objects if multiple possibilities exist. One skilled in the art will see that correlate source images 2100 applies a series of tests to potential combinations of blobs in the input blob lists, to match blobs that are considered optimum matches for each other as candidates for particle counting. However, these tests are exemplary only and presented in an exemplary order; these tests may be rearranged in order or even deleted for cost savings or to reduce processing complexity, and none of the particular tests described is considered essential.

Step 2105 of correlate source images 2100 receives blob lists BA, BB as input. For example, each of blob lists BA, BB may be blob lists as generated from a measurement field within a cartridge 130 or 130' imaged to sensor 160 and processed using the process source image 1300 method, as described above, with BA and BB being blob lists from the same measurement field utilizing different illumination modules 200, 300.

Step 2110 initializes a loop spanning each blob in BA; the remaining steps of correlate source images 2100 determine whether there is a match in BB for each such blob, and if a match is found, whether it is the best available match. Step 2120 determines a position of the next blob ba(1) to be considered in BA, and defines a blob bb(1) as the first blob in BB. Step 2130 initializes a loop spanning each blob bb in BB. Step 2140 determines a position of the next blob bb to be considered in BB, calculates a variable DISTANCE1 between the position of blobs ba(1) and bb, and calculates a variable DISTANCE2 between the position of blobs ba(1) and bb(1). Step 2142 is a decision step that determines whether DISTANCE2 is greater than DISTANCE1. If so, step 2144 sets blob bb(1) as the current blob bb. If not, or after step 2144, step 2146 determines whether all blobs in BB have been processed, and returns to step 2140 until all blobs BB have been processed. In this manner, steps 2130 through 2146 find at least the best spatially matched blob bb(1) for the current blob ba being processed, and identifies the distance DISTANCE2 between bb(1) and ba.

Step 2152 is a decision step that determines whether DISTANCE2 is greater than 16 µm. The choice of 16 µm as the maximum for DISTANCE2 reflects an expected maximum spatial registration tolerance between images from which blob lists BA, BB were generated and may vary in embodiments within a range of 12 to 20 microns. This allows for registration shifts between the location of a particle as imaged under different illumination sources. Such shifts can be caused by, e.g., chromatic aberration, mechanical shifts between or during exposures, or particle movement within a cartridge. In an embodiment, the choice of 16 µm as the maximum for DISTANCE2 limits such shifts to a magnitude where it is possible to generate an initial set of correlated blobs imaged under different illumination sources with satisfactory reliability using a simple correlation distance. The value of DISTANCE2 should be set large enough to encompass the registration shifts characteristic of the system, which may be approximately twice the size the particle of interest. This allows for the inclusion of some false correlations where the blobs originate from different particles. The optimal value of DISTANCE2 may also depend on parameters including particle size, magnitude of registration shifts, and particle density. A more refined analysis of the distance between the blobs in a correlated pair, discussed in connection with FIG. 29A, serves to remove blobs due to false correlations. In embodiments with greater shifts or higher particle density, correct correlation may be achieved using more advanced image registration methods, for instance relying on fiducial markers on the cartridge or recognition of corresponding particle patterns in the two images.

In an embodiment, If DISTANCE2 is greater than 16 µm, blobs ba(1) and bb are at least an initial match, and correlate source images 2100 advances to step 2170 for further processing. If DISTANCE2 is less than 16 µm, blobs ba(1) and bb are not a match, and correlate source images 2100 advances to step 2160. Step 2160 is a decision step that determines whether all blobs in BA have been processed. If no, correlate source images 2100 returns to step 2120 to try to find matches for another blob ba(1). If yes, correlate source images 2100 terminates at step 2165, returning blob list BC (defined below) as a list of blobs that correlate across blob lists BA and BB.

Step 2170 is reached only when there is a preliminary, acceptable match between blobs ba(1) and bb. At this point, further processing is done to determine whether the preliminary match is the best match, or whether there are better matches in BA for blob bb than blob ba(1). Step 2170 identifies blob ba as blob ba(1). Step 2172 initializes a loop spanning all blobs in BA; in this loop the blob being processed is identified as ba(2). Step 2175 determines a position of the next blob ba(2), and calculates a variable DISTANCE3 between the position of blobs ba(2) and bb. Step 2180 is a decision step that determines whether DISTANCE3 is less than DISTANCE2 (which was established as the distance between blobs ba(1) and bb in step 2140). If DISTANCE3 is not less than DISTANCE2, blob ba(2) is not a better match for blob bb than blob ba(1), so correlate source images 2100 advances to step 2190. But if DISTANCE3 is less than DISTANCE2, blob ba(2) is a better match for blob bb than blob ba(1). In this case, correlate source images 2100 advances to step 2185, wherein blob ba(2) is identified as the (current) "best match" of blob bb, by setting blob ba as blob ba(2) and setting DISTANCE2 as DISTANCE3. Thus, further blobs ba will not only have to be closer to blob bb than the first blob ba(1) to be considered the best match for bb, they will have to be closer to bb than ba(2).

After step 2185, correlate source images 2100 advances to step 2190, another decision step that determines whether all blobs in BA have now been processed against blob bb. If not, correlate source images 2100 returns to step 2175 to try to find a better match for blob bb. If so, correlate source images 2100 advances to step 2192.

Step 2192 is a decision step that determines whether blob ba remains the same blob ba(1) that was found to be an initial match for blob bb(1) in steps 2130 through 2152. If not, correlate source images 2100 reverts to step 2160 without adding anything to the correlated blob list (because the better match ba will eventually be found as the outer loop beginning at step 2110 advances to the appropriate ba). If ba remains the same blob ba(1), correlate source images 2100 advances to step 2194, where blobs ba(1) and bb(1) are added to blob list BC with an indication that they are correlated blobs. From step 2194, correlate source images 2100 advances to step 2160, discussed above, to finish looping through candidate blobs from BA and BB.

The correlation method discussed in relation to FIGS. 28A and 28B may be extended to correlation of more than two blob lists. This would be relevant for systems requiring correlation of events from more than two images. Exemplary embodiments include particle identification systems such as system 100, FIG. 2 (reference to system with separate beam paths) and system 100', FIG. 8, with additional illumination sources and/or conditions. For instance, a three-color fluorescence system used for counting CD4 and CD8 cells could be based on separate detection of CD3, CD4, and CD8 positive cells but would require correlating events from three images, e.g., correlating three blob lists.

Events from more than two blob lists may be correlated by applying correlatesourceimages 2100 as described above, to pairs of blob lists. In an embodiment, blob lists A, B, and C are correlated. First, blob lists A and B are correlated using correlatesourceimages 2100. This generates a blob list AB(A,B) containing correlated events. In this discussion, the notation I(I,J) means a blob list representing blobs found only in blob list I based on correlation of input blobs lists I and J, and IJ(I,J) means a blob list representing blobs correlating between blob lists I and J based on correlation of input blob lists I and J. Remaining uncorrelated events from lists A and B are placed in blob lists A(A,B) and B(A,B). Next, each event in correlated blob list AB(A,B) is assigned an image location, e.g., pixel coordinates, as the average image location of the two correlated blobs from lists A and B respectively. Blob list C is now processed three times by correlatesourceimages 2100 to correlate it with blob lists A(A,B), B(A,B), and AB(A,B). Correlation of blob lists C and A(A,B) leads to the generation of blob lists AC(A,B,C), A(A,B,C), and C(A,C), where blob list AC(A,B,C) contains blobs that spatially correlate across A and C but not B, blob list A(A,B,C) contains blobs from A that did not spatially correlate with blobs from B or C, and blob list C(A,C) contains blobs from C that did not spatially correlate with blobs from A. Likewise, correlation of blob lists C and B(A,B) leads to the generation of blob lists BC(A,B,C), B(A,B,C), and C(B,C). Correlation of C with AB(A,B) leads to the generation of blob lists ABC(A,B,C), AB(A,B,C), and C(AB,C), where blob list ABC(A,B,C) contains blobs that spatially correlated in A, B, and C, blob list AB(A,B,C) contains blobs that spatially correlate in A and B but not C, and blob list C(AB,C) contains blobs from C that did not spatially correlate with AB. Finally, the events from C(A,C), C(B,C), and C(AB,C) are combined into a single blob list C(A,B,C) containing all the blobs in C that did not spatially correlate with blobs in A or B. The final output, representing all two-way and three-way correlations and remaining uncorrelated blobs, consists of blob lists ABC(A,B,C), AB(A,B,C), AC(A,B,C), BC(A,B,C), A(A,B,C), B(A,B,C), and C(A,B,C). Throughout, image locations for correlated blobs are set to the average of the individual image locations as defined in the original blob lists A, B, and C.

If a fourth blob, D, list is present, as would be generated in a four-color system, blob list D could then be correlated with blob lists ABC(A,B,C), AB(A,B,C), AC(A,B,C), BC(A,B,C), A(A,B,C), B(A,B,C), and C(A,B,C) generated above, also using correlate source images 2100.

Figure 29A:
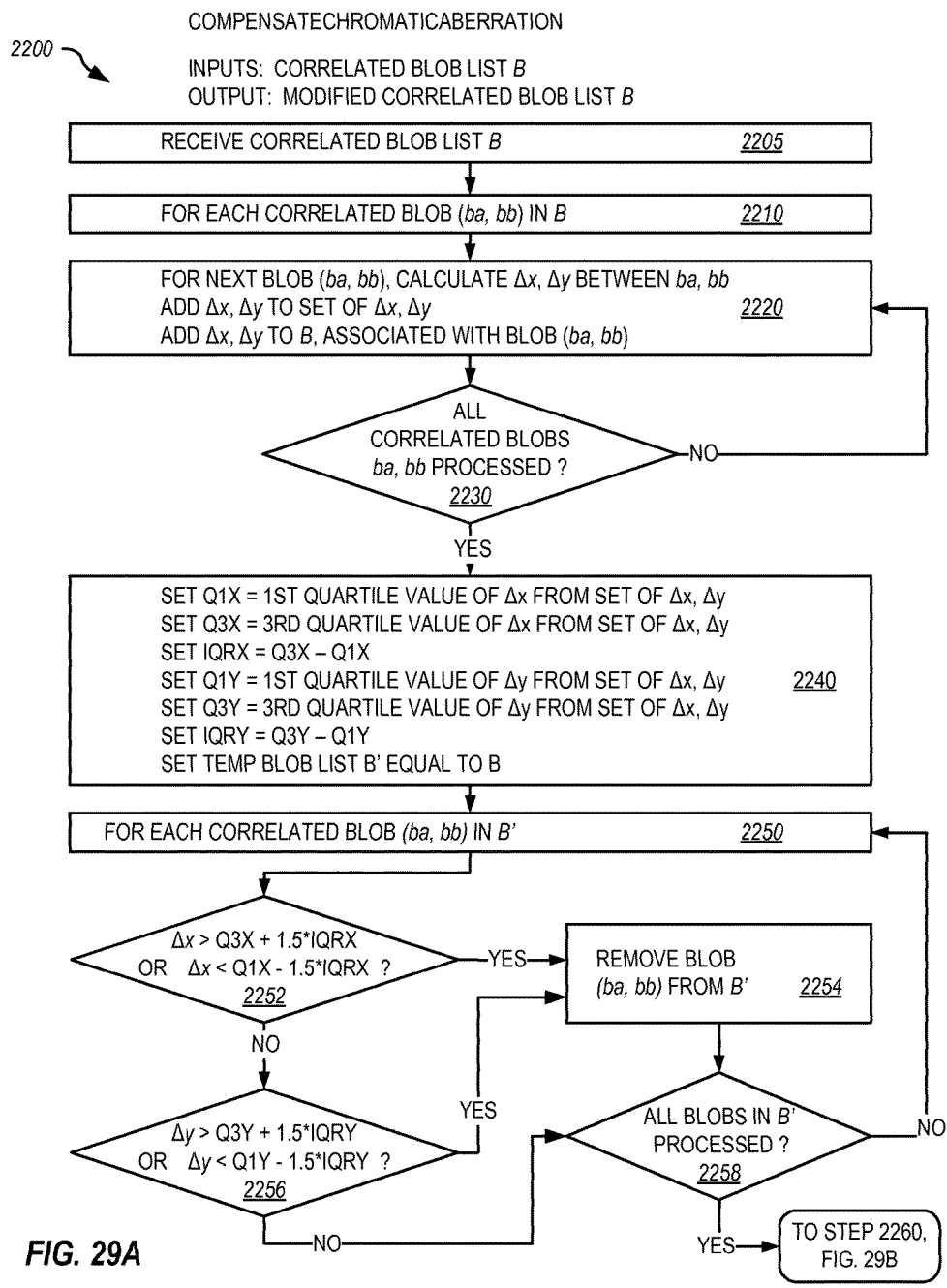
FIGS. 29A and 29B are flowcharts of a subroutine that filters a correlated list of blobs based on differences of position between correlated blobs in the list, in an embodiment.
Figure 29B:
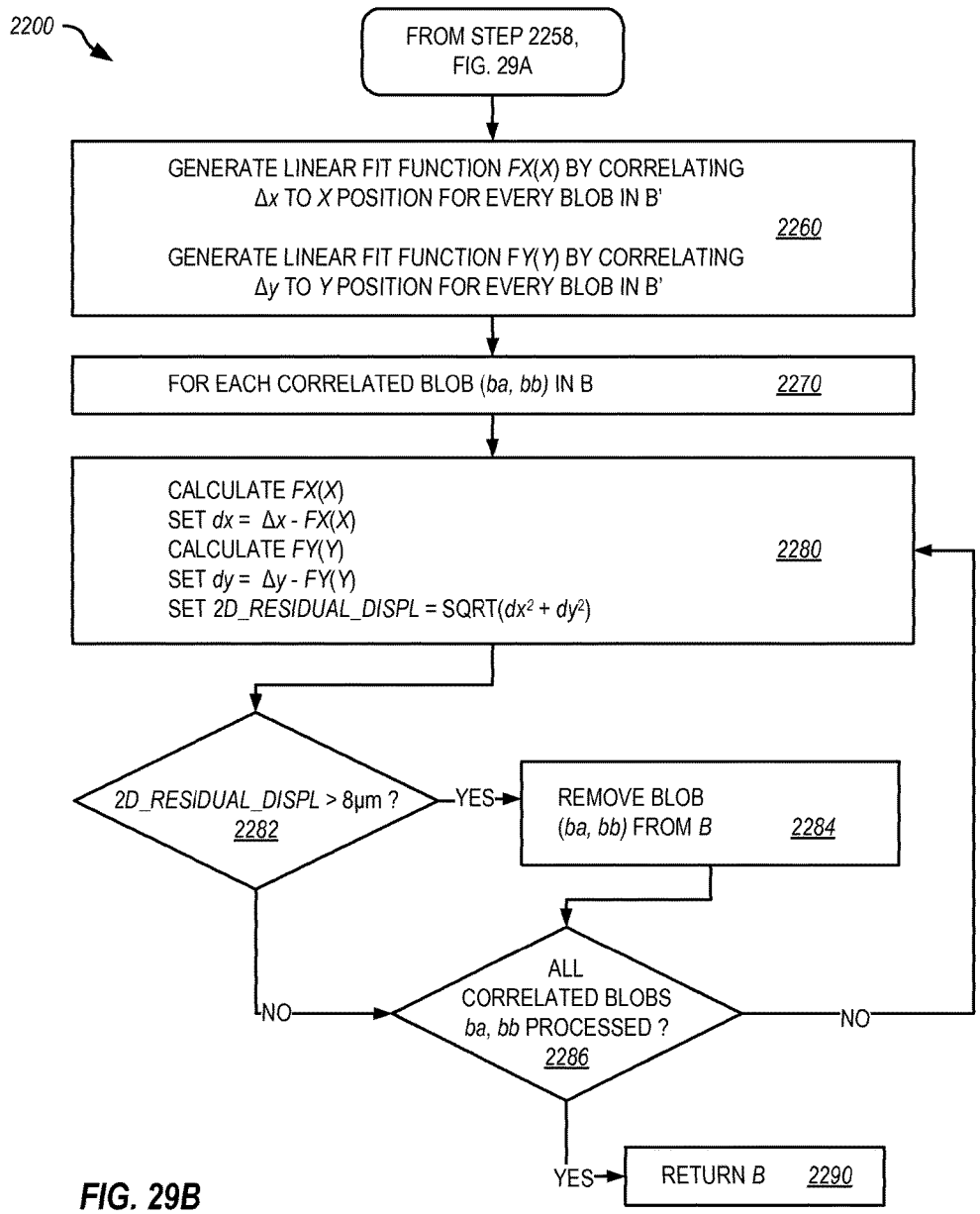

FIGS. 29A and 29B are flowcharts of an exemplary subroutine compensate chromatic aberration (B) 2200 that takes a correlated blob list B as input and modifies it by removing blobs that are outliers in terms of expected spatial matching between two source images. Compensate chromatic aberration 2200 may be performed, for example, by processor 460 of systems 100, 100', taking blob list BC, discussed above in connection with FIGS. 28A and 28B, as input. Generally speaking, compensate chromatic aberration 2200 tightens the matching criteria for acceptable correlation between blobs identified utilizing different illumination modules, by eliminating blobs that are outliers of the correlated blob population in terms of spatial shifts. Thus, compensate chromatic aberration 2200 allows "typical" registration shifts, as defined by the blob population itself, but screens out blobs with atypical registration shifts from one image to another. The "typical" registration shifts may occur due to, e.g., chromatic aberration effects between the fluorescence wavelengths in which the images are produced, localized sample heating due to light power used to illuminate the sample, evaporation, and mechanical shifts.

Step 2205 of compensate chromatic aberration 2200 receives blob list B as input. For example, blob list B may be a correlated blob list generated by the correlate source images 2100 method, as described above, wherein B contains information of matched blobs ba, bb. Step 2210 sets up a loop spanning all correlated blobs (ba, bb) in B. Step 2220 calculates registration shifts $\Delta x$, $\Delta y$ for the next blob (ba, bb), adds $\Delta x$, $\Delta y$ to a temporary set of $\Delta x$, $\Delta y$ and adds $\Delta x$, $\Delta y$ to the information associated with blob (ba, bb) in B. Step 2230 is a decision step that determines whether all blobs (ba, bb) in B have been processed; if not, compensate chromatic aberration 2200 returns to step 2220 to process another blob (ba, bb), and if so, compensate chromatic aberration 2200 advances to step 2240. Step 2240 calculates a (Q3-Q1 $\Delta x$ INTERVAL) and a (Q3-Q1 $\Delta y$ INTERVAL) from the set of $\Delta x$, $\Delta y$ established by step 2220, and sets up a temporary blob list B' that is initially equal to blob list B.

Step 2250 sets up a loop that is performed for each blob in B'. Steps 2252 and 2256 are decision steps that determine whether $\Delta x$ or $\Delta y$ for a given blob exceeds 1.5 times the respective calculated (Q3-Q1 $\Delta x$ INTERVAL) and (Q3-Q1 $\Delta y$ INTERVAL). These steps remove false correlations and/or outliers from B' such that the fit performed in step 2260 (FIG. 29B, discussed below) is based on typical, true correlations only. Hence, the choice of the values retained for the correlation is biased such that false correlations will definitely be discarded, and even potentially true correlations that are outliers may be discarded. Therefore a standard inter quartile-based outlier rejection method with relatively tight criterion, such as a multiplication factor in the range from 1 to 2, results in good performance. In an embodiment, a multiplication factor of 1.5 is applied.

If the answer to either of the decisions in steps 2252 and/or 2256 is yes, compensate chromatic aberration 2200 advances to step 2254, which removes blob (ba, bb) from B'. After step 2254, or if steps 2252 and 2256 are answered no, compensate chromatic aberration 2200 advances to step 2258, another decision step that determines whether all blobs (ba, bb) in B' have been processed. If not, compensate chromatic aberration 2200 returns to step 2250 to process another blob (ba, bb) in B', and if so, compensate chromatic aberration 2200 advances to step 2260.

Step 2260 generates linear fit functions FX(x) and FY(y) from the information associated with each blob (ba, bb) in B' by correlating Δx to x position and Δy to y position, respectively. This enables screening of blobs (ba, bb) on the basis of a fit the normal shift of a blob in both dimensions based on its position; this is useful because spatial shift effects may depend on initial position of a blob within a measurement field.

Having set up linear functions FX(x) and FY(y) based on the blobs with the most typical registration shifts as discussed in connection with steps 2240 through 2260, compensate chromatic aberration 2200 discards temporary blob list B' and utilizes FX(x) and FY(y) for further screening of blob list B. Step 2270 sets up a loop that spans all correlated blobs (ba, bb) in B. For a given blob (ba, bb), step 2280 calculates FX(x) and FY(y) from the x, y position of each blob, an associated dx=Δx−FX(x) and dy=Δy−FY(y), and a two-dimensional residual displacement 2D_RESIDUAL_DISPL=sqrt (dx2+dy2). Step 2282 is a decision step that determines whether 2D_RESIDUAL_DISPL is greater than 8 μm. As in similar screening values discussed above, the value of 8 μm used in step 2282 depends on the size of the particles being counted, the possibility of random movement and on the expected maximum spatial registration tolerance between images from which blob lists BA, BB were generated. The screening value of 8 μm could vary in other embodiments within a range of about 6 μm to 10 μm. If step 2282 determines that 2D_RESIDUAL_DISPL is greater than 8 μm, blob (ba, bb) is removed from B in step 2284. This is another screen based on shifts between the location of blobs imaged with different illuminators associated with the same particle. 2D_RESIDUAL_DISPL is set to be smaller than the diameter of the particle of interest, while allowing for some degree of random particle movement. In an embodiment where the particle of interest has a diameter of approximately 10 μm, a useful value for 2D_RESIDUAL_DISPL may be 8 μm. An optimal value of 2D_RESIDUAL_DISPL may for example be based on analysis of a tradeoff between missing true correlations due to registration errors, and including false correlations in cases with a high particle density or high likelihood of particles being clumped together. The optimal value of 2D_RESIDUAL_DISPL therefore depends on the particle size.

If step 2282 determines that 2D_RESIDUAL_DISPL is less than 8 μm, or after blob (ba, bb) is removed from B, compensate chromatic aberration 2200 advances to step 2286. Step 2286 is a decision step that determines whether all correlated blobs (ba, bb) in B have been processed. If not, compensate chromatic aberration 2200 returns to step 2280 to process another blob (ba, bb), and if so, compensate chromatic aberration 2200 returns modified blob list B in step 2290.

FIGS. 30A and 30B are flowcharts of an exemplary subroutine filter low intensity correlations (BA, B) 2300 that takes an initial blob list BA and a correlated blob list B as input, and modifies correlated blob list B by removing blobs that belong to a distribution other than an expected main blob distribution in terms of intensity. Filter low intensity correlations 2300 may be performed, for example, by processor 460 of systems 100, 100', taking blob lists BA, discussed above in connection with FIGS. 27A through 27C, and correlated blob list BC, discussed above in connection with FIGS. 28A, 28B, 29A and 29B, as input. Generally speaking, filter low intensity correlations 2300 analyzes a histogram of peak intensities of a population of blobs (optionally compensating for non-uniform illumination), to determine a number of populations detected, and may discard low-intensity populations that might result from effects such as cross-staining, cross excitation, biological properties, autofluorescence and light scattering. Like compensate chromatic aberration 2200, filter low intensity correlations 2300 screens by comparing possible outliers, in this case outlying populations, to a main distribution.

Step 2305 of filter low intensity correlations 2300 receives initial blob list BA and correlated blob list B as input. Step 2310 performs a Gaussian distribution fit, $$f(x) = f_0 \exp\left[-\left(\frac{x - x_0}{w}\right)^2\right],$$

to TSID values associated with blobs in BA (see, e.g., the explanation of step 2040, FIG. 27B). The Gaussian fit determines parameters f0, x0 and w that relate to the height, center point and width of the Gaussian peak, respectively. Step 2310 also determines the maximum intensity maxy over all intensities in BA, and calculates $$\frac{\max_y [y_{all}(x)]}{f_0}.$$

Step 2320 is a decision point that determines whether $$\frac{\max_y [y_{all}(x)]}{f_0}$$

is greater than a parameter threshold, which may be set within a range of about 1.5 to 2.0, and is typically 1.7. If not, filter low intensity correlations 2300 advances to step 2360, described below. If so, filter low intensity correlations 2300 advances to step 2330.

Step 2330 calculates a parabolic fit of the usual form ax2+bx+c to intensity data of blob list BA in the range [maxx[yall(x)]:3*maxx[yall(x)]]. Therefore, the range wherein the data is fitted starts at the peak of the intensity distribution from blob list BA, and extends to three times the peak value. The choice of 3 as the multiplier that defines the top end of the range is set to clearly exceed the extent of dim, false event populations in the event that this is the tallest peak in the histogram; in embodiments, this multiplier might vary within the range of about 2 to 5. A decision step 2340 determines whether the parabolic coefficient a is greater than zero. If so, the range [maxx[yall(x)]:3*maxx[yall(x)]] fits a parabola that is upward facing, and the vertex of the parabola indicates a demarcation between two distinct distributions. That is, the parabolic fit serves to locate the "valley" between two, possibly overlapping, populations in the histogram, if two populations exist. The fit range is set to extend across the valley. Therefore if a>0, filter low intensity correlations 2300 advances to step 2350 which removes correlated blobs from B wherein TSID<−b/2a (the parabola vertex). If a<0, or after step 2350, filter low intensity correlations 2300 advances to step 2355 and returns blob list B.

If filter low intensity correlations 2300 reaches step 2360 as a result of step 2320, further screening is attempted. Step 2360 calculates median[ycorr(x)] of TSIDs of each blob in correlated blob list B. A decision step 2370 determines whether x0+2*w (from the Gaussian fit determined in step 2310) is greater than median[ycorr(x)] from step 2360. If so, the correlated blob distribution does not include a significant population in addition to the population captured by the Gaussian distribution fit, and the population is considered well behaved. Therefore if x0+2*w>median[ycorr(x)], filter low intensity correlations 2300 advances to step 2394 without further filtering. The factor 2 used as a multiplier for w may vary, in embodiments, between values of about 1.5 and 3.

If step 2370 determines that x0+2*w≤median[ycorr(x)], the correlated blob distribution includes a population with higher values than predicted by the Gaussian distribution, and a chance remains that the distribution includes a peak of false events. In this case, filter low intensity correlations 2300 advances to step 2380, which again calculates a parabolic fit of the form ax2+bx+c, this time to data within the range of [x0: 3*x0].

A decision step 2340 determines whether the parabolic coefficient a is greater than zero. If so, the range [x0: 3*x0] fits a parabola that is upward facing, and the vertex of the parabola indicates a demarcation between two distinct distributions. Therefore if a>0, filter low intensity correlations 2300 advances to step 2392 which removes correlated blobs from B wherein TSID<−b/2a (the parabola vertex). If a<0, or after step 2392, filter low intensity correlations 2300 advances to step 2394 and returns blob list B.

The brightness of the particles of interest, e.g., CD4+ T-helper cells, may vary significantly due to both biological variation and measurement related effects. In certain embodiments, the camera sensor (e.g., sensor 160) has a wide dynamic range, for example 16 bits, to accommodate this brightness variation. Alternatively, for a system utilizing a camera sensor with a smaller dynamic range, for example 8 bits, it may not be possible to find a single exposure time for which all particles are above the detection limit without some particles reaching saturation. Saturation may affect the apparent properties of a particle of interest in such a way that it is falsely rejected by the particle identification process (e.g., the methods and subroutines called therein, as described in FIGS. 13-30).

Therefore, in an embodiment, the dynamic range of an 8-bit camera sensor is extended by acquiring multiple images at different exposure times, where the dimmest particles are properly recorded at the longest exposure time and the brightest particles are properly recorded at the shortest exposure time. For example, step 840, described in connection with FIG. 13, may consist of acquiring multiple images at different exposure times. Each of these individual images may be processed according to step 845 in FIG. 13, to generate a blob list for each individual exposure. Prior to performing step 860 in FIG. 13, the correlate source images routine described in FIG. 28 may be used to correlate blobs found in more than one exposure. If images are acquired at only two different exposure times, blob lists from each of these two exposure times may be propagated through the correlate source images routine, leading to a single correlated blob list. Alternatively, if images are acquired at more than two different exposure times, two of the exposures may be propagated through the correlate source images routine, leading to a single correlated blob list, which may then be propagated through the correlate source images routine together with the blob list associated with another exposure time. A loop defined thereby may continue until all exposures for a given light source have been incorporated in the correlation. Blobs found in only one exposure may be scaled to a common exposure time and placed in a blob list for further processing. For blobs found in more than one exposure, the brightest occurrence of the blob where all pixel intensities within the blob are less than or equal to 250 may be scaled to the same common exposure time and placed in the same blob list. This blob list may then be further processed as outlined in FIG. 13, beginning with step 860.

In another embodiment, the dynamic range of an 8-bit camera sensor is extended by, in step 840, acquiring multiple images at a constant exposure time set such that no particles of interest are saturated. Prior to performing step 860 in FIG. 13, all these images may be added pixel by pixel to provide a single, saturation free image of greater than 8 bits resolution.

III. Fluidic Features and Methods

In this section, methods and devices for reliably performing passive continuous flow in a fluidic channel are described. One method and device: (1) utilizes gravity to provide driving pressure; (2) starts and stops liquid flow in a controlled manner; and (3) delivers known quantities of liquid into the channel. Certain embodiments described herein further provide continuous flow of a known liquid volume through a channel, with flow terminating before the channel is completely drained of liquid. As disclosed herein, this effect may be achieved by the following process, beginning with filling an inlet port with a known volume. Pressure-driven flow due to gravity and surface tension moves the liquid through a channel to an outlet port. Introduction of a wicking pad located near the outlet port absorbs the liquid and ensures that flow continues until all the liquid in the inlet port has entered the channel. Proper separation of the wicking pad from the outlet port, design of outlet port geometry, and control of solid-liquid-gas surface tension ensures that flow terminates before the channel is drained of liquid. The wicking pad further prevents backflow of liquid through the outlet port into the channel.

The term "surface tension" is used herein in relation to the surface energies of the solid-liquid, liquid-gas, and solid-gas interfaces associated with the fluidic cartridge. Surface tension or surface energy impacts the ability of a liquid to wet a solid surface, characterized by a liquid-solid-gas interface. In the present disclosure, exemplary solids include plastics and plastics with modified surface properties. Exemplary liquids include aqueous solutions, including aqueous solutions with surface tensions modified by surface active components such as surfactants or amphiphilic molecules. An exemplary gas is air.

Figure 31:
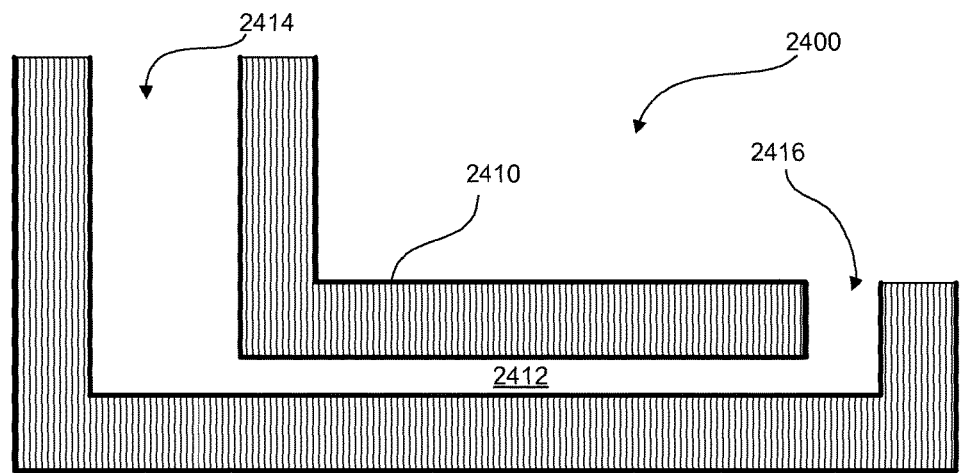
FIG. 31 is a cross-sectional view of a fluidic cartridge, in accordance with an embodiment.

FIG. 31 shows a cross-sectional view of a fluidic cartridge 2400, in accordance with an embodiment. Fluidic cartridge 2400 includes a casing 2410 defining a channel 2412 with an inlet port 2414 and an outlet port 2416. Casing 2410 may be formed as a single piece or separate pieces that cooperate to define channel 2412, inlet port 2414 and outlet port 2416. For example, casing 2410 may be formed by an injection molding process. As an alternative, casing 2410 may be formed from a combination of a lower substrate, defining the bottom of channel 2412 and an upper component defining inlet port 2414 and top of channel 2412 connecting inlet port 2414 with outlet port 2416.

Figure 32:
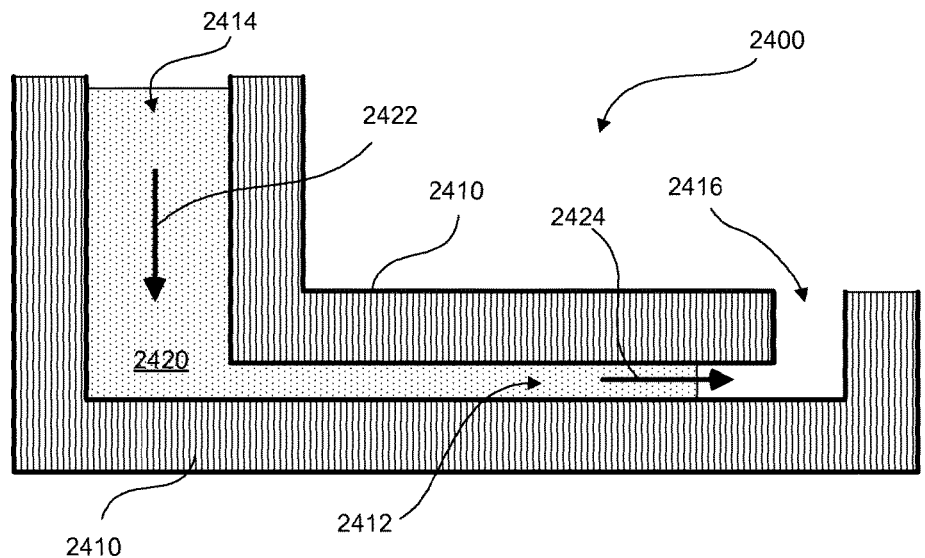
FIG. 32 shows the fluidic cartridge of FIG. 31, illustrating liquid flow into the fluidic cartridge.

For applications, such as in-vitro diagnostics, a liquid 2420 (such as an aqueous solution) may be introduced into channel 2412 at inlet port 2414 of fluidic cartridge 2400, as shown in FIG. 32. Due to characteristics such as height differences in the fluidic columns between inlet port 2414 and outlet port 2416, a differential pressure exists therebetween that drives liquid 2420 to flow from inlet port 2414 to outlet port 2416 in a direction indicated by arrows 2422 and 2424. If channel 2412 has not previously been filled with liquid, capillary forces due to surface tension may also contribute to moving liquid 2420 through channel 2412.

Figure 33:
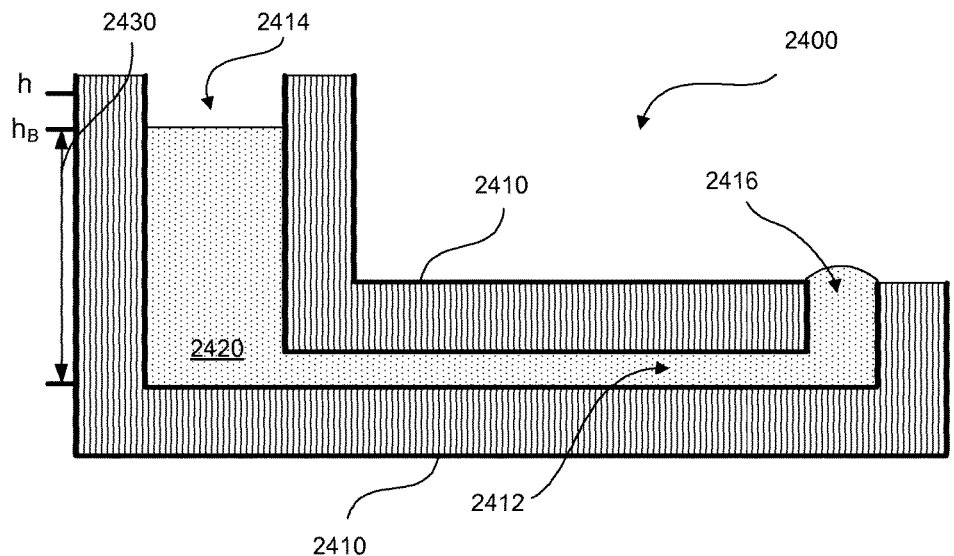
FIG. 33 shows the fluidic cartridge of FIGS. 31 and 32 at the point where the outlet port capillary valve stops liquid flow.

Depending on outlet port 2416 geometry (e.g., diameter and shape) and surface tension associated with the liquid, solid cartridge material, and gas (typically air), outlet port 2416 acts as a capillary valve with a characteristic burst pressure. Referring to FIG. 33, liquid 2420 flows through the channel then stops at a height hB 2430 as determined by the capillary valve burst pressure at outlet port 2416.

Figure 34:
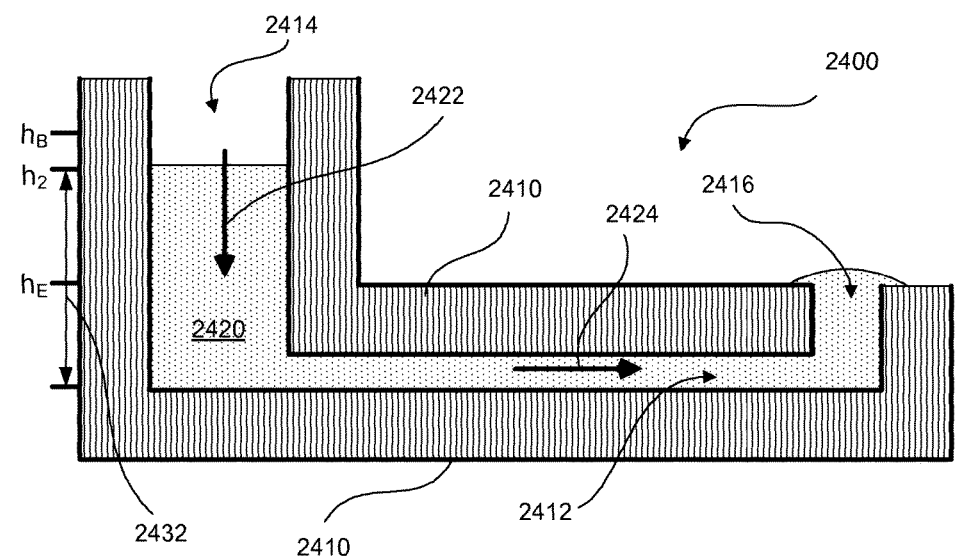
FIG. 34 shows the fluidic cartridge of FIGS. 31 and 32, shown here after the surface tension at the outlet port has been broken as the pressure at the outlet port has exceeded burst pressure.

Once surface tension at outlet port 2416 is overcome by the pressure exerted by liquid 2420 at outlet port 2416, liquid 2420 begins to flow out of outlet port 2416, as shown in FIG. 34. That is, the difference between the fluid pressure and ambient pressure exceeds a burst pressure, overcoming the surface tension at outlet port 2416. Consequently, liquid flows continuously through channel 2412 until the level of liquid 2420 at inlet port 2414 drops to equilibrium level hE 2432 (indicated by double arrows), which is lower than first level 2430. At this point, flow ceases because the pressures due to surface tension forces and gravity are balanced between inlet port 2414 and outlet port 2416. For the small dimensional sizes of channel 2412 in applications of interest (e.g., on the order of millimeters to tens of millimeters), the gravity-induced forces are comparable in magnitude to surface tension forces.

Figure 35:
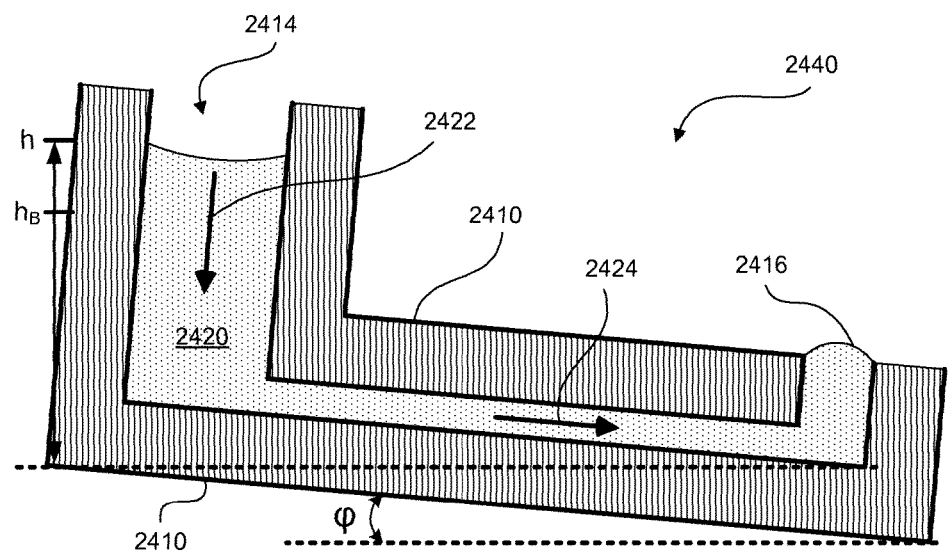
FIG. 35 shows the fluidic cartridge of FIG. 32, this time including a tilt for altering the pressure differential between the inlet port and the outlet port.

In one embodiment, a tilt may be introduced to the fluidic cartridge so as to alter the pressure differential between the inlet port and the outlet port. As shown in FIG. 35, a tilted cartridge 2440 includes components similar to those of previously-described fluidic cartridge 2400. In contrast to the embodiment illustrated in FIGS. 31-33, tilted cartridge 2440 is tilted from a level orientation by an angle φ such that the pressure differential at outlet port 2416 is greater than those shown in FIGS. 32 and 33. In effect, the column height of inlet port 2414 is increased without requiring additional liquid volume, and thus the gravity-induced pressure is increased over that of the level orientation. As a result, burst pressure is more easily attained, and liquid 2420 empties to a relatively lower liquid level in tilted cartridge 2440 as compared to level, fluidic cartridge 2400.

Figure 36:
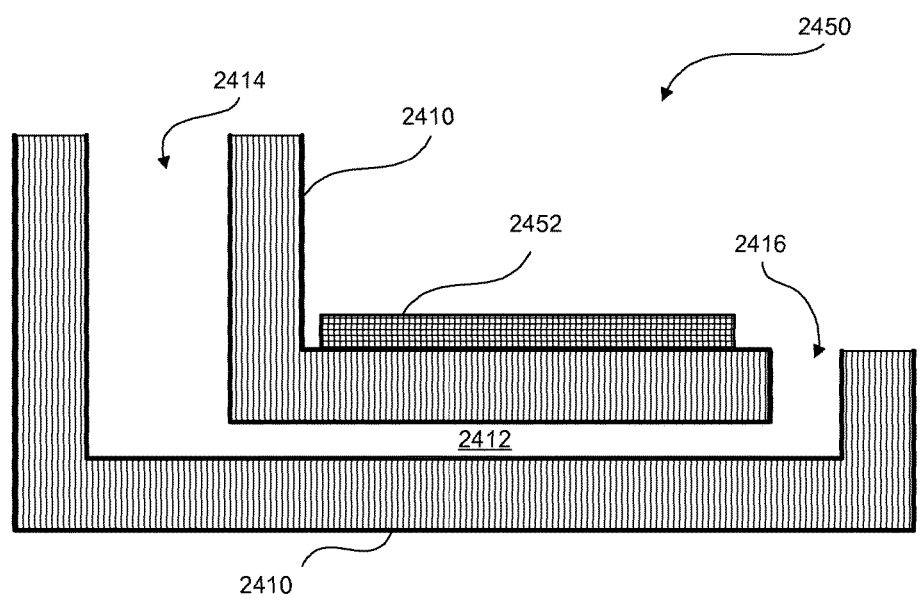
FIG. 36 is a cross-sectional view of a fluidic cartridge including a wicking pad, in accordance with an embodiment.

Regardless of the specific configuration used (e.g., level cartridge 2400 or tilted cartridge 2440), a fluidic column builds up at outlet port 2416 such that at some point liquid flow stops when the pressure at the outlet port balances the pressure at the inlet port. This condition does not always guarantee that all of the liquid in the inlet port 2414 flows through channel 2412 to outlet port 2416. One way to maintain liquid flow through channel 2412 is to introduce a wicking pad, which essentially acts as a reservoir for absorbing liquid therein. As will be explained below, the wicking pad acts to reduce the column height of the outlet port such that liquid flow is maintained. FIG. 36 is a cross-sectional view of a fluidic cartridge 2450 including a wicking pad 2452, in accordance with an embodiment.

Figure 37:
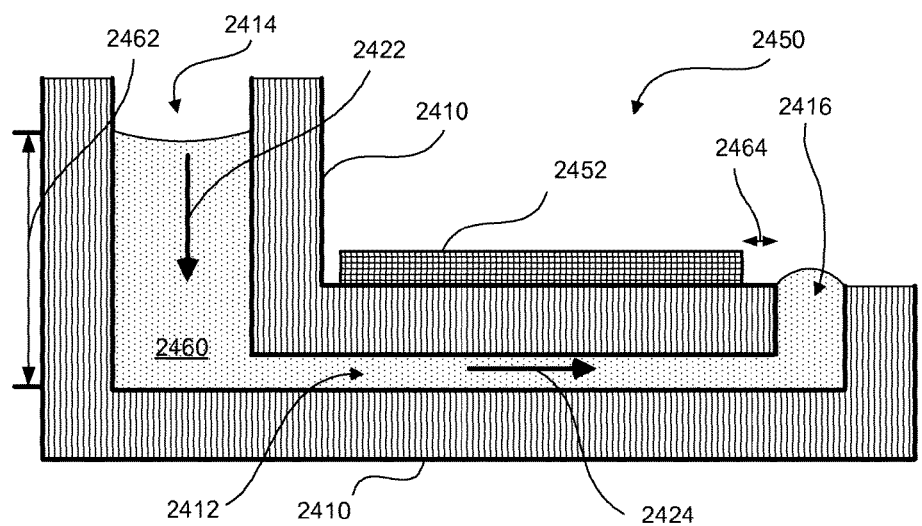
FIG. 37 shows the fluidic cartridge of FIG. 36, illustrating the liquid flow in the fluidic cartridge with the wicking pad.
Figure 38:
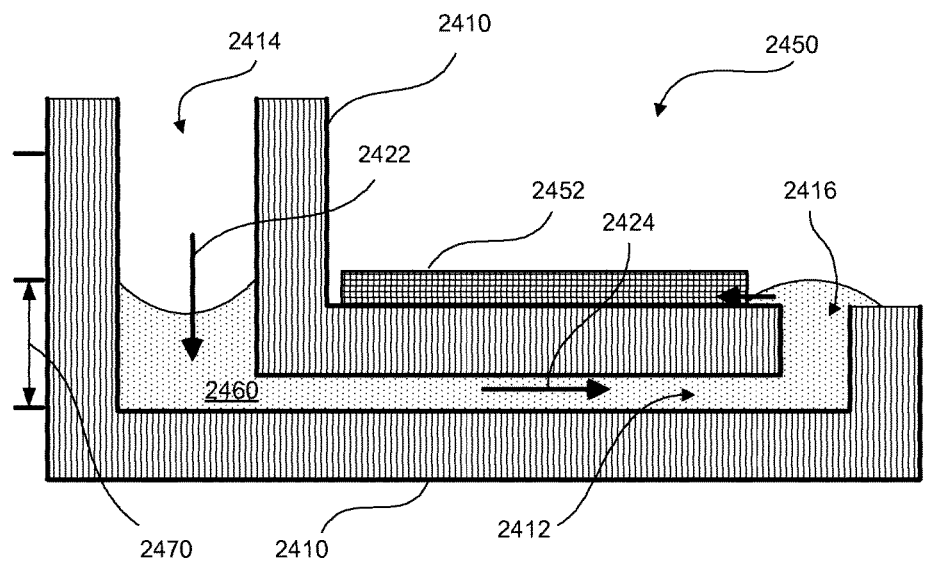
FIG. 38 shows the fluidic cartridge of FIGS. 36 and 37, shown here after the surface tension at the outlet port has been broken as the pressure at the outlet port has exceeded burst pressure such that the liquid, upon contacting the wicking pad, is absorbed into the wicking pad.

As shown in FIG. 37, liquid 2460 may be inserted into fluidic cartridge 2450 such that, at inlet port 2414, liquid 2460 reaches a level 2462 while liquid 2460 is kept within outlet port 2416 by surface tension. When the burst pressure is exceeded, as shown in FIG. 38, liquid 2460 flows out from outlet 2416 in a manner dependent on the liquid-solid-gas surface tension and solid surface geometry. As the liquid column at outlet 2416 expands, it eventually makes contact with wicking pad 2452, which quickly absorbs liquid 2460. The strong capillary forces of wicking pad 2452 absorb liquid 2460 at a rate faster than the rate at which channel 2412 can supply liquid 2460 to outlet port 2416. Due to this rate difference, the liquid column height at outlet 2416 is rapidly decreased. After absorption by wicking pad 2452, the liquid column height at outlet 2416 is decreased and then subsequently replenished by flow through channel 2412. Provided that the column height 2470 of inlet 2414 provides enough pressure for liquid 2460 to repeatedly overcome the burst pressure and re-contact wicking pad 2452, back pressure from the liquid column of outlet 2416 is avoided and continuous flow occurs in channel 2412. Flow through channel 2412 is maintained until the liquid column height 2470 of inlet 2414 drops such that there is insufficient pressure to overcome the burst pressure of outlet 2416. Careful choice of material surface energies, tilt angle, and liquid column heights enables the entire volume of liquid 2460 in inlet 2414 to be completely emptied through channel 2412. In this manner, prescribed amounts of liquid 2460 can be flowed from inlet port 2414 through channel 2412, despite large surface tensions from dimensionally small fluidics geometries that might be encountered in a diagnostic device.

Certain embodiments require that the liquid remain in the channel at all times during liquid flow and after the inlet has emptied. For instance, an in-vitro diagnostic may require the biological sample in the liquid to incubate in the channel for a period of time so as to allow the sample to chemically react with reagents that are immobilized to the channel surface. Capillary pressures obtained by wicking pad 2452 can be large enough to pull liquid 2460 from channel 2412 in an unrestrained or uncontrollable manner, causing channel 2412 to go dry or be filled with detrimental gas bubbles. Liquid flow from outlet port 2416 to wicking pad 2452 is affected by a number of factors: absorbance properties of wicking pad 2452 (determined by material composition), geometrical placement of wicking pad 2452 with respect to outlet 2416, the physical geometry of cartridge features like outlet and inlet ports 2414 and 2416, and the surface energies of cartridge materials and liquids (determined by material composition, surface treatments, and time-dependent surface adsorption). One or more of these properties can be optimized for desired performance. For instance, surface energies around outlet port 2416 can be modified by plasma treatment to promote wetting of the solid material by liquid 2460.

In an embodiment, a small gap 2464 is introduced between wicking pad 2452 and outlet port 2416 to prevent draining of channel 2412 (see FIG. 37). When the rate of liquid 2460 from outlet port 2416 is less than absorbance rate of wicking pad 2452 (such as happens when the inlet port empties), surface tension forces in gap 2464 around outlet port 2416 "break" the liquid flow to wicking pad 2452. To restore flow, inlet 2414 can be filled with sufficient liquid 2460 so that once again the inlet pressure exceeds the burst pressure. Flow then resumes as wicking pad 2452 once again absorbs excess liquid 2460 from outlet port 2416. In this manner, flow can be started and stopped multiple times in a controlled manner without draining channel 2412 completely of liquid 2460. A key aspect of the embodiment is that wicking pad 2452 does not actively pump liquid 2460 through channel 2412, but only acts a reservoir to store excess liquids. Gravity provides pressure-driven flow through cartridge channel 2412.

Figure 39:
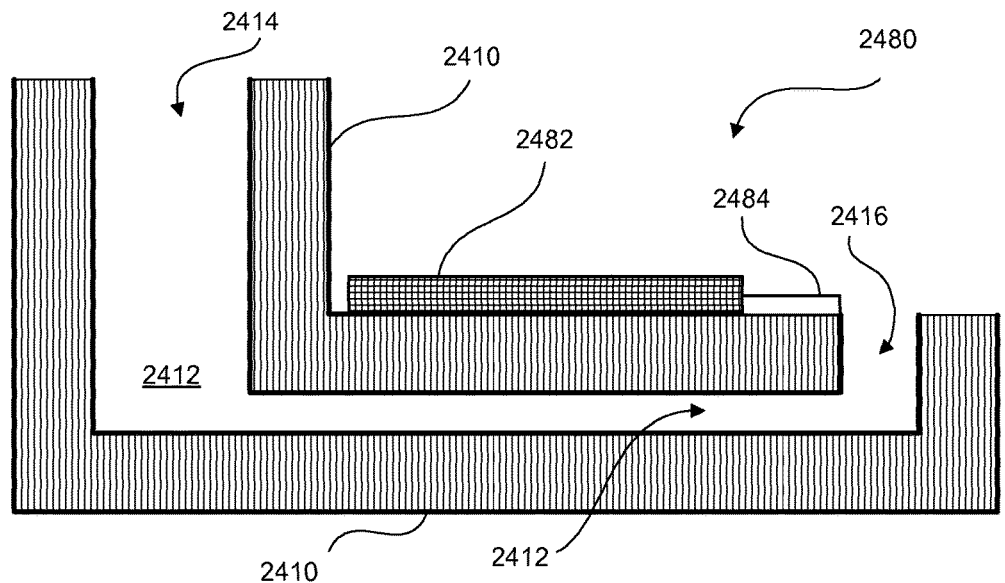
FIG. 39 is a cross-sectional view of a fluidic cartridge including a combination of a wicking pad and a rail, in accordance with an embodiment.

An embodiment also employs the use of ridge or rail features at the outlet port to directionally steer the liquid to the wicking pad. Surface tension forces associated with the sharp corners of the rail preferentially direct the liquid along the rail towards the wicking pad in a more controlled manner. FIG. 39 is a cross-sectional view of a fluidic cartridge 2480, including a combination of a wicking pad 2482 and a rail 2484, in accordance with an embodiment.

Figure 40:
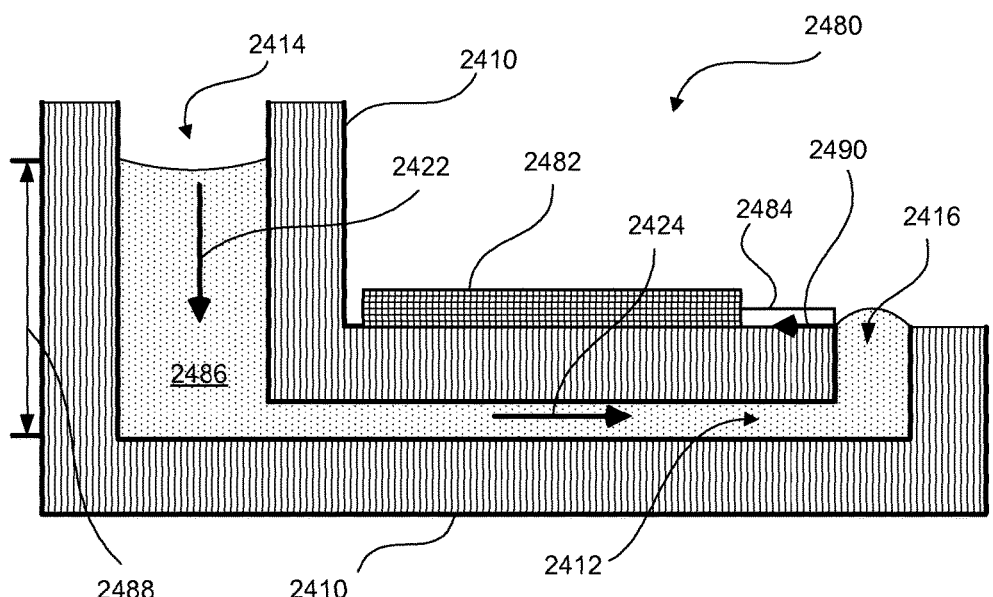
FIG. 40 shows the fluidic cartridge of FIG. 39, illustrating liquid flow within the fluidic cartridge and the effect of capillary action as the liquid is drawn along the rail.
Figure 41:
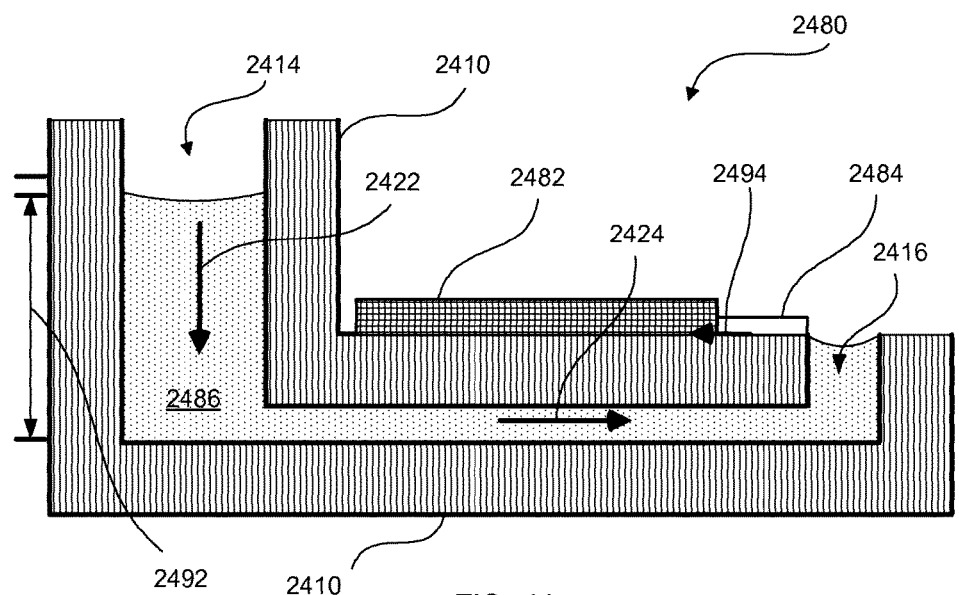
FIG. 41 shows the fluidic cartridge of FIGS. 39 and 40, illustrating the effect of capillary action as the portion of the liquid along the rail is absorbed into the wicking pad.
Figure 42:
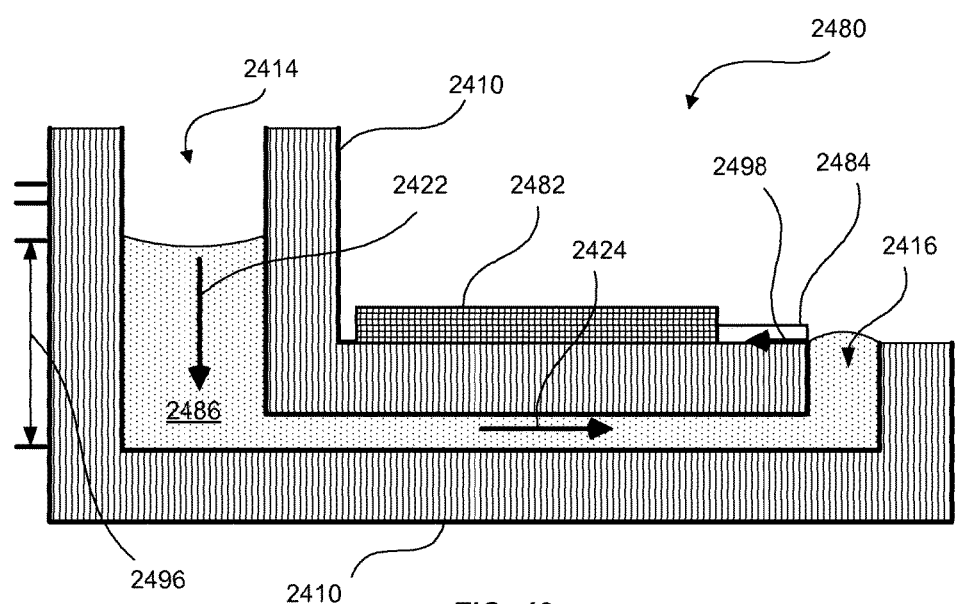
FIG. 42 shows the fluidic cartridge of FIGS. 39-41, illustrating the consequent effect of capillary action along the rail as liquid is drawn along the rail.

FIGS. 40-42 illustrate a process of liquid flow through fluidic cartridge 2480, in accordance with an embodiment. FIG. 40 shows fluidic cartridge 2480 with a liquid 2486 inserted therein such that, initially, liquid 2486 is at a first level 2488 (indicated by a double-headed arrow) at inlet port 2414. When liquid 2486 contacts rail 2484, a portion of liquid 2486 is drawn along rail 2484 by capillary action 2490 (indicated by an arrow). Once this portion of liquid 2486 reaches wicking pad 2482, that portion of liquid 2486 immediately in contact with rail 2484 is drawn into wicking pad 2482 by capillary action 2494 (indicated by an arrow), as shown in FIG. 41. Consequently, the level of liquid 2486 at inlet port 2414 drops incrementally to a second level 2492 (indicated by a double-headed arrow). Then, due to a combination of the pressure exerted by liquid 2486 and ambient pressure, the process illustrated in FIGS. 40 and 41 is repeated, as liquid level at inlet port 2414 drops to a third level 2496 (indicated by a double-headed arrow) and another portion of liquid 2486 is drawn along rail 2484 by capillary action 2498 (indicated by an arrow), as shown in FIG. 42.

Figure 43:
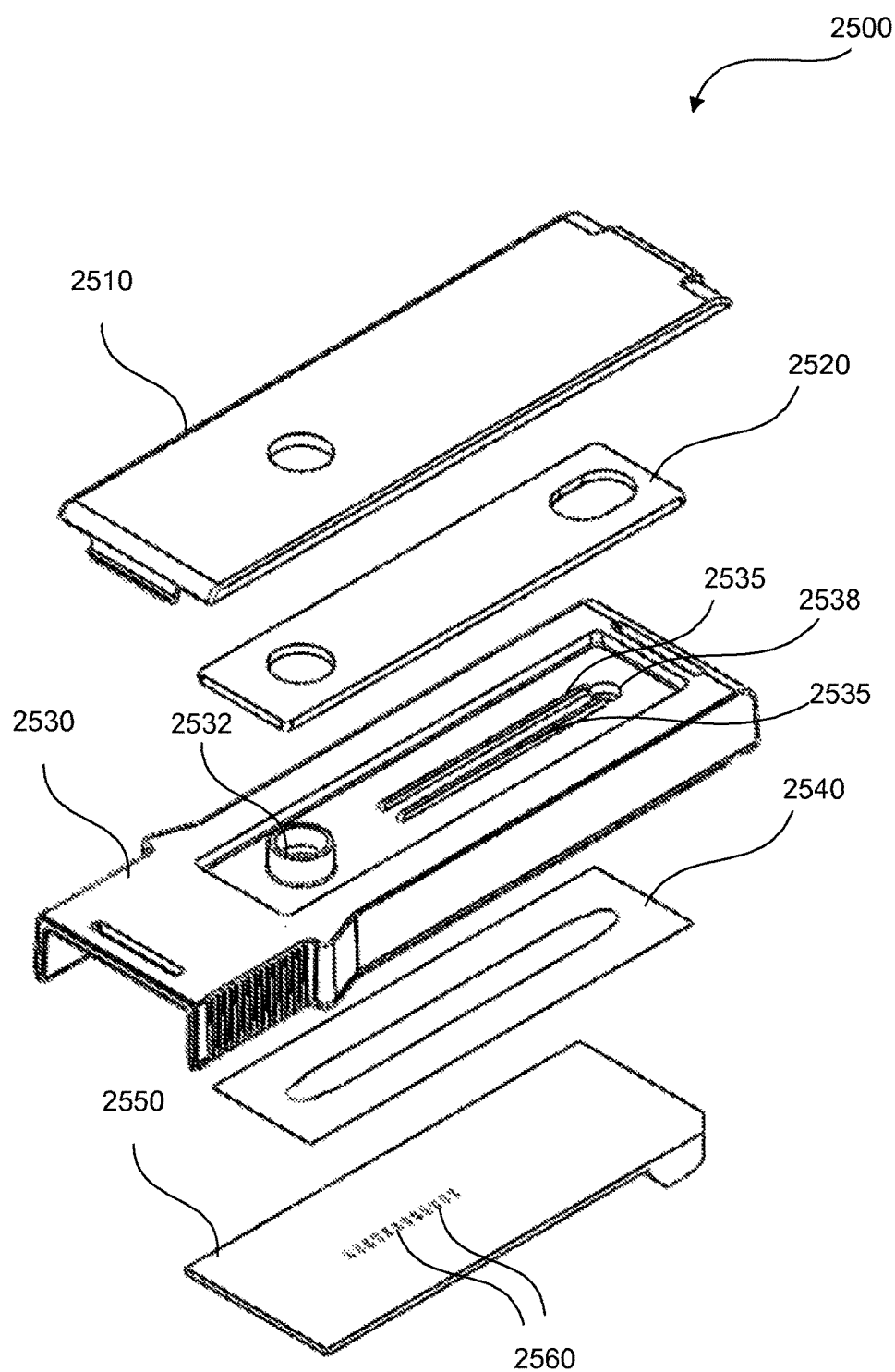
FIG. 43 shows an exploded view of an exemplary fluidic cartridge, in accordance with an embodiment.
Figure 44:
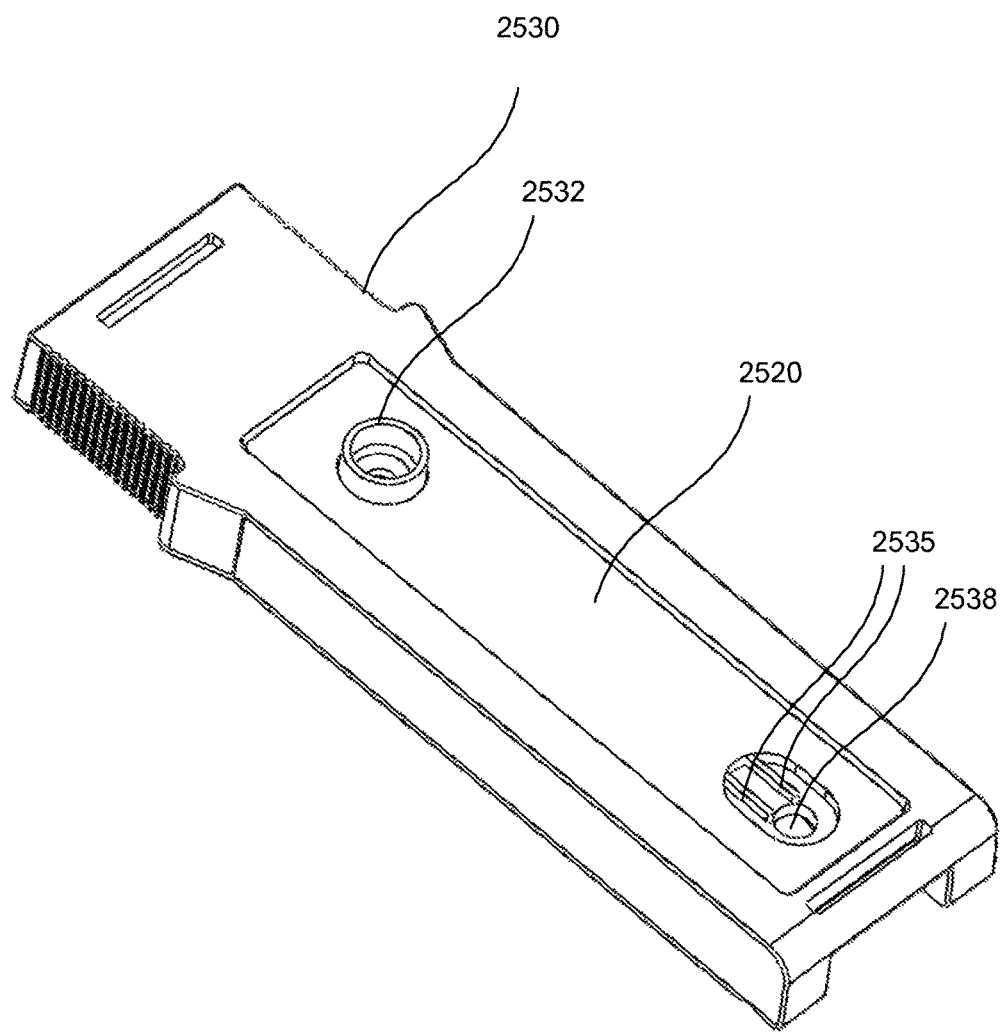
FIG. 44 shows an elevated view of a portion of the exemplary fluidic cartridge of FIG. 43, shown here to illustrate assembly of the upper component and wicking pad, in accordance with an embodiment.

FIG. 43 shows an exploded view of an exemplary cartridge 2500 including a wicking pad 2520 and rails 2535, in accordance with an embodiment. Cartridge 2500 includes a lid 2510 and a wicking pad 2520, both of which fit over an upper component 2530. Upper component 2530 defines an inlet port 2532, a pair of rails 2535, and an outlet port 2538. Upper component 2530 is attached via an adhesive gasket 2540 to a planar waveguide arrangement 2550, shown here with a plurality of a microarray of protein "spots" 2560 printed thereon. FIG. 44 further shows upper component 2530 in combination with wicking pad 2520. As shown in FIG. 44, wicking pad 2520 fits around inlet port 2532 and outlet port 2538 such that the combination of features functions to provide the flow control mechanism described in FIGS. 39-42.

IV. Cartridge Features and Methods

This section is divided into the following subsections: Cartridge and Lid Visual and Tactile Features; Uniform Dried Reagent Placement in Inlet Port; Exemplary Performance of Uniform Dried Reagent Placement in Inlet Port; Demonstrations of Uniform and Nonuniform Staining in Dried Reagent Cartridges; Sample Hold and Release Cartridge; Exemplary Performance of Sample Hold and Release Cartridge; and Cartridge/Instrument Control Features.

Cartridge and Lid Visual and Tactile Features

Figure 45:
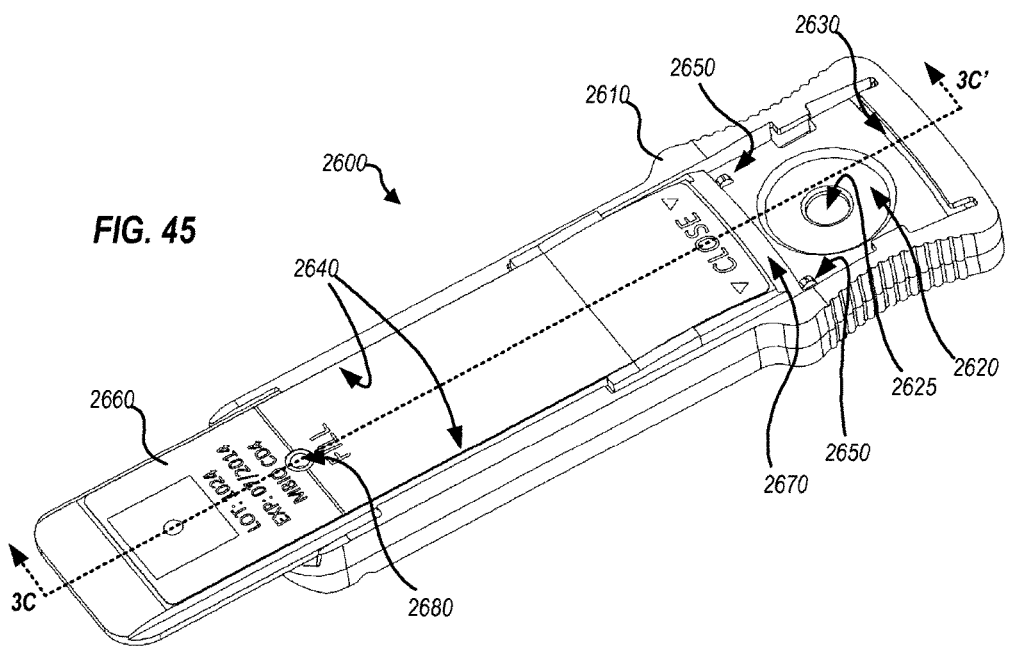
FIGS. 45 and 46 are schematic, isometric views of a cartridge for acquiring and/or processing a whole blood sample, in an embodiment, with a lid thereof shown in an open position and a closed position.
Figure 46:
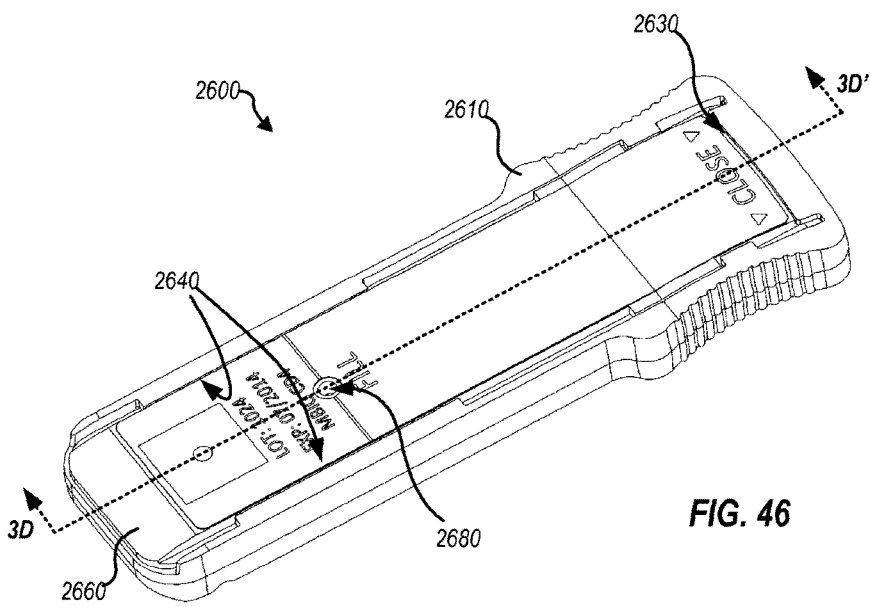
Figure 47:
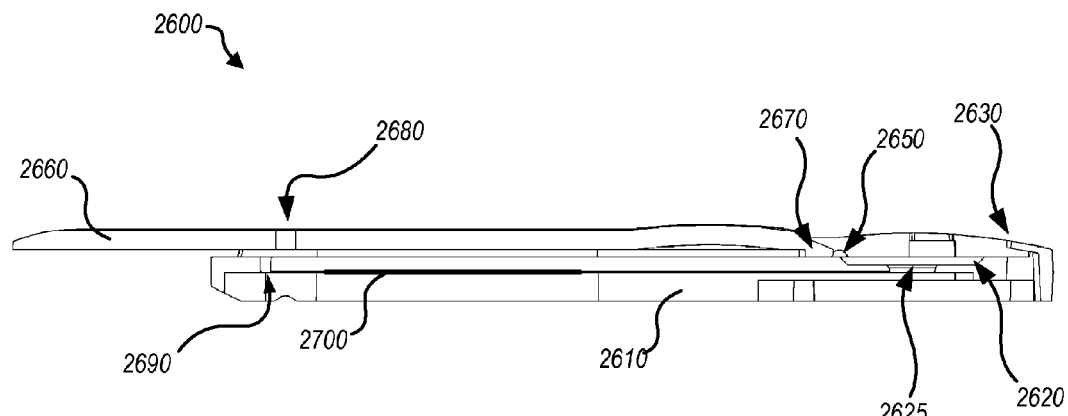
FIGS. 47 and 48 are schematic cross-sectional views of the cartridge shown in FIGS. 7 and 8.
Figure 48:
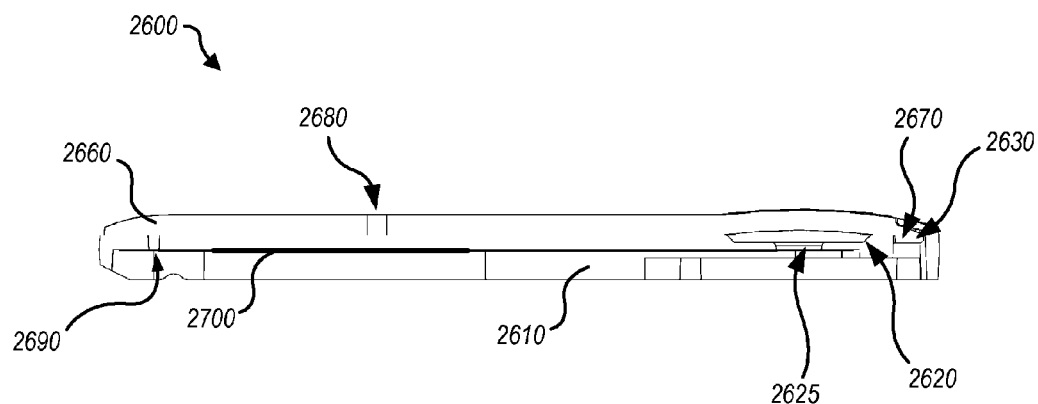

FIGS. 45 and 46 illustrate a cartridge 2600 for acquiring and/or processing a sample, in an isometric view; FIGS. 47 and 48 show cross-sectional illustrations of cartridge 2600. Cartridge 2600 may be utilized, for example, as a cartridge 130 or 130' of FIG. 2 or 8. Cartridge 2600 includes a cartridge body 2610 and a cartridge lid 2660. FIGS. 45 and 47 show lid 2660 in an open position relative to body 2610, while FIGS. 46 and 48 show lid 2660 in a closed position. Lid 2660 slides within a channel 2640 formed by body 2610. Lid 2660 includes a flange 2670 at a leading edge thereof, that is adapted for capture by a capture feature 2630 of cartridge body 2610, thus forming a locking mechanism, as discussed below.

When lid 2660 is in the open position shown in FIGS. 45 and 47, an inlet port 2620 is exposed. Inlet port 2620 has a volume capacity that is greater than the volume of liquid required for proper operation of cartridge 2600 in systems 100, 100'. Inlet port 2620, and other features of cartridge 2600 that are exposed to the sample, are treated (e.g., with plasma) to make them hydrophilic such that the sample is drawn through a fluidic path of cartridge 2600. Inlet port 2620 forms an inner region 2625 that is sized such that its hydrophilic surfaces provide an interfacial tension that exceeds the force of gravity (for a sample of a volume up to a maximum volume that exceeds the required sample volume as well as the volume of a typical fingerstick). This feature enables acquisition of such sample by simply inverting cartridge 2600 and placing inlet port 2620 onto a sample droplet, such as a blood droplet on an upturned finger. Alternatively, the sample droplet can be contacted with cartridge inlet port 2620 while the cartridge is on a surface such as a table top. Alternatively, the sample can be transferred into port 2620 using a transfer device such as a transfer pipette or other dedicated device (e.g., DIFF-SAFE® blood tube adapter).

Inner region 2625 of inlet port 2620 connects with a fluidic channel that forms a detection region 2700 that extends for a distance down the length of the cartridge, providing multiple fields of view for imaging thereof. Downstream of detection region 2700, the fluidic channel connects with a vent 2690. Vent 2690 has a small channel cross section such that the expansion at the outlet of vent 2690 forms a capillary gate, thereby stopping flow of the fluid sample. Alternatively, vent 2690 may be configured with a cross section much larger than that of fluid channel such that the expansion at the inlet to vent 2690 will result in a capillary gate.

FIGS. 45 and 47 also show bumps 2650 that provide resistance to lid 2660 at a known location as lid 2660 slides along channel 2640. Lid 2660 may be of a flexible material such that it can slide over bumps 2650 while providing resistance and tactile feedback. Bumps 2650 serve two functions: (1) they discourage accidental locking of lid 2660 into the locked position (described below) by a user or during shipping and handling; and (2) bumps 2650 provide a reference location for a window 2680 formed in lid 2660. When flange 2670 abuts bumps 2650, as shown in FIGS. 45 and 47, a window 2680 is positioned over a terminal region of the fluidic path of cartridge 2600. When a sample (e.g., blood) is loaded into inlet port 2620, the visual appearance of the sample under window 2680 indicates that sufficient volume has been supplied to enable analysis. Upon seeing the sample under window 2680, a user of cartridge 2600 can push lid 2660 such that flange 2670 rides over bumps 2650 and covers inlet port 2620, until capture feature 2630 captures flange 2670. Lid 2660 may be of a flexible material and, prior to capturing flange 2670, lid 2660 may be in a stressed state, such that upon flange 2670 being captured by capture feature 2630, lid 2660 changes to a less stressed state. This irreversibly closes lid 2660 over inlet port 2620 so that potentially biohazardous samples can be handled safely, and prevents reuse of cartridge 2600. In the embodiment shown in FIGS. 45 through 48, capture feature 2630 includes a ridge that rides up over flange 2670 as lid 2660 moves into the closed position, generating a downward force thereon. When a trailing edge of flange 2670 reaches a leading edge of cartridge body 2610, flange 2670 is captured, with the ridge forming a locking mechanism that prevents flange 2670 from being easily dislodged. Other embodiments may have different physical features on either a cartridge body or lid that perform the functions of covering an inlet port and locking the lid to the cartridge, making the cartridge safe to handle even with a biohazardous substance therein.

In its closed position, lid 2660 may function to reduce evaporation from cartridge 2600, which may result in an extension of the time allowed to pass between sample loading and readout of cartridge 2600 using, e.g., systems 100, 100' shown in FIGS. 2 and 8. Another embodiment of a cartridge lid allows for addition of fluid to cartridge 2600 to enhance the humidity inside cartridge 2600, thereby reducing evaporation. Yet another embodiment of a cartridge lid has sealing functionality as well as features to allow for fluid addition to cartridge 2600.

Figure 49:
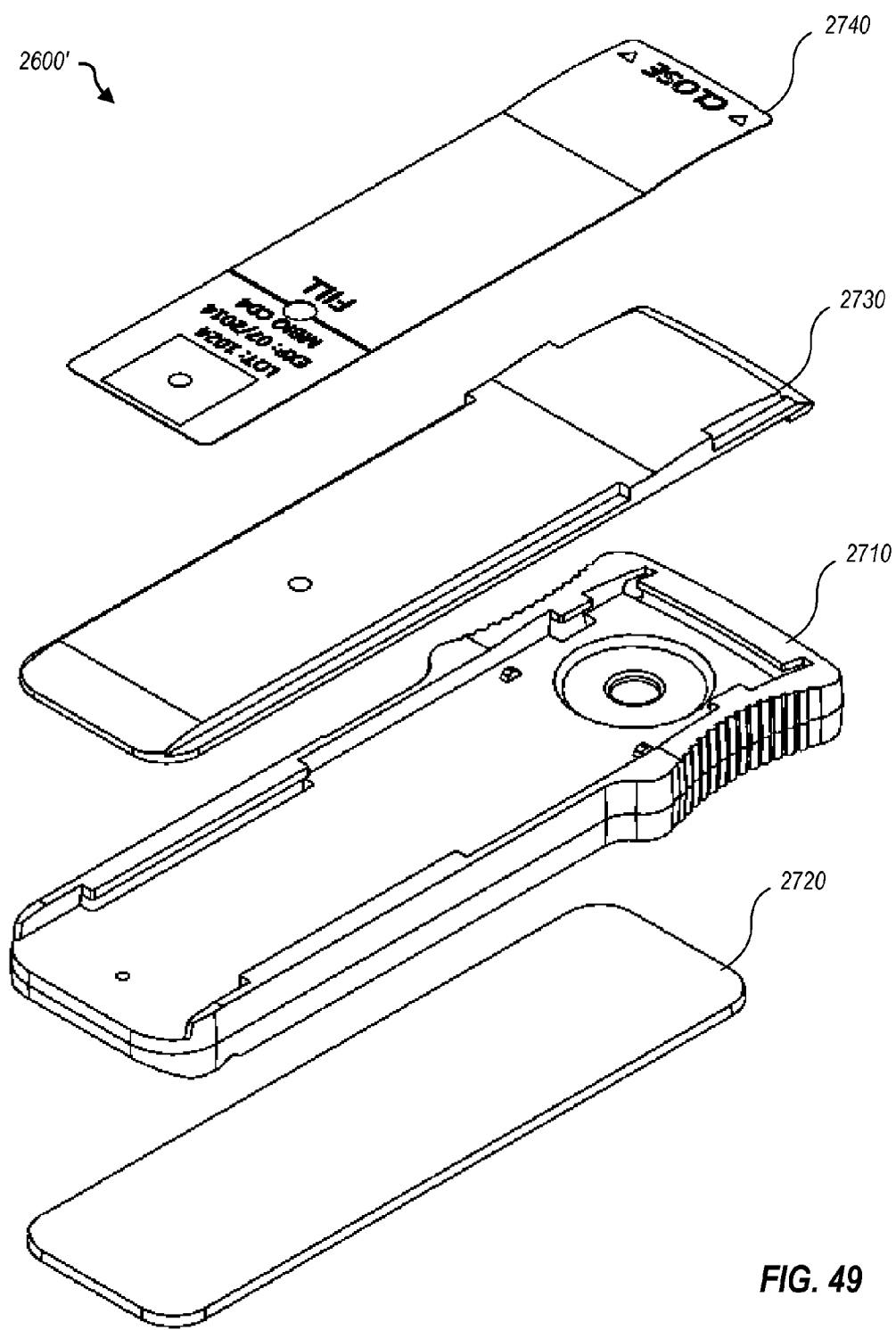
FIG. 49 shows an exploded view of a cartridge, in an embodiment.

FIG. 49 shows an exploded view of a cartridge 2600' that may be utilized as a cartridge 130 or 130', FIG. 2 or 8, or cartridge 2600, FIGS. 45-48. Cartridge 2600' includes a top cartridge element 2710, a bottom cartridge element 2720, a lid 2730 and a label 2740. Top cartridge element 2710 has an indentation feature (not visible in FIG. 49) that forms a fluid channel when connected, for instance by laser welding, to bottom cartridge element 2720.

Figure 50:
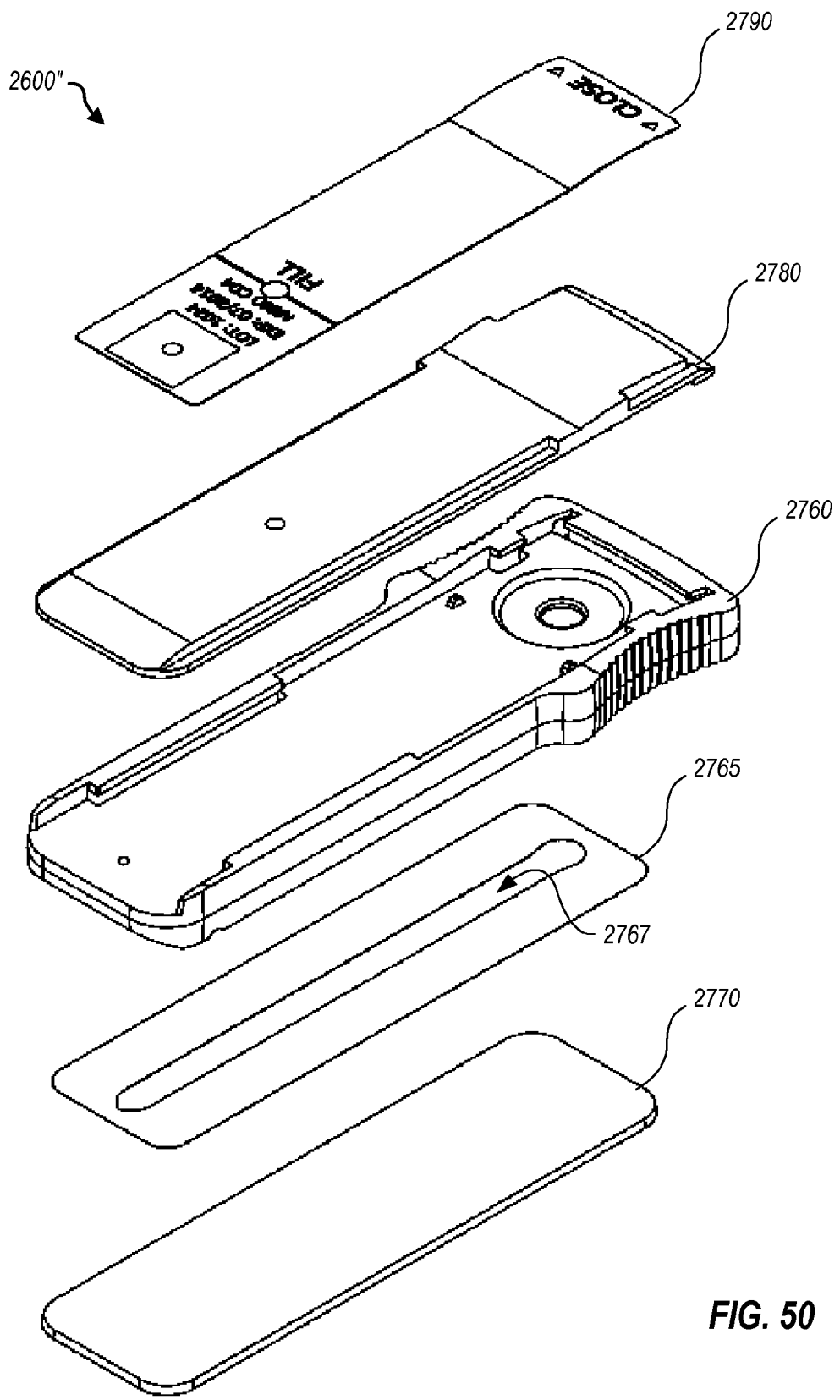
FIG. 50 shows an exploded view of a cartridge, in an embodiment.

FIG. 50 shows an exploded view of a cartridge 2600" that may be utilized as a cartridge 130 or 130', FIG. 2 or 8, or cartridge 2600, FIGS. 45-48. Cartridge 2600" includes a top cartridge element 2760 and a bottom cartridge element 2770 with a gasket 2765 between. Inner surfaces of top cartridge element 2760 and bottom cartridge element 2770 are planar surfaces, such that thickness of gasket 2765 may be tightly controlled to set channel height 385, FIG. 6. Alternatively, one or both of top cartridge element 2760 and bottom cartridge element 2770 may include a standoff that defines channel height 385. Cartridge 2600" also includes a lid 2780 and a label 2790. In cartridge 2600", top cartridge element 2760 does not include an indentation feature. Instead, gasket 2765 forms an aperture 2767 that, when gasket 2765 connects top cartridge element 2760 with bottom cartridge element 2770, forms a fluid channel.

Lid 2730 of cartridge 2600' (shown in FIG. 49) or a portion thereof and, equivalently, lid 2780 of cartridge 2600" (shown in FIG. 50) or a portion thereof may be manufactured of an optical grade, clear material to allow for loss free and distortion free illumination from above, if for instance used in systems 100, 100' shown in FIG. 3. If lid 2730 or lid 2780 includes a label thereon, the label's impact on the optical system should be considered. For example, any label through which illumination beams would pass may have to be formed of a material of optical quality and controlled thickness so that placement of the illumination beam at the measurement field would be controllable. For this reason, it may be advantageous for the label not to be placed over the detection region, or to form apertures or cutouts in the label to keep the label out of the way of the illumination beams. In another embodiment, illumination and detection may be performed from below, in which case lid 2730 of cartridge 2600' and lid 2780 of cartridge 2600" may be opaque, of lesser than optical quality, and/or include features, labels, etc. over the detection region.

Uniform Dried Reagent Placement in Inlet Port

Figure 51A:
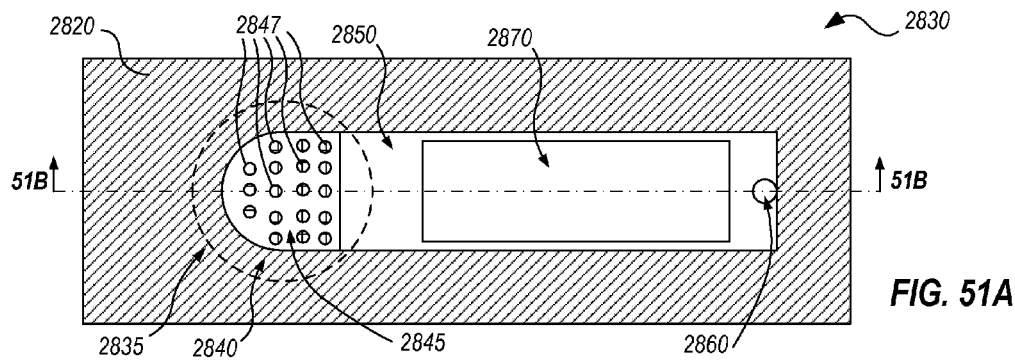
FIGS. 51A and 51B schematically illustrate a cartridge, in an embodiment.
Figure 51B:
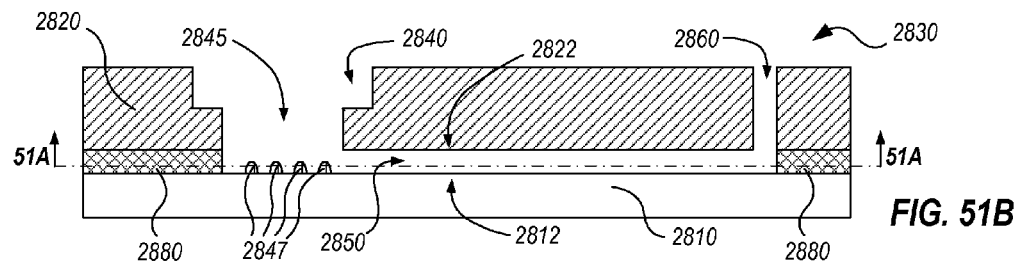

A cartridge embodiment is now described that utilizes engineered dried reagent methods to deliver accurate analyte detection directly from a small volume liquid sample, e.g., a volume of about 10 microliters. Examples of analytes include particle analytes such as CD4+ T-helper cells, other cell types, bacteria, viruses, fungi, protozoa, and plant cells, and non-particle analytes such as proteins, peptides, prions, antibodies, micro RNAs, nucleic acids, and sugars. FIGS. 51A and 51B schematically illustrate a cartridge 2830 that includes a planar plastic substrate 2810 and a plastic upper housing component 2820. FIG. 51A is a plan view of cartridge 2830 looking upwards from a line 51A-51A in FIG. 52, while FIG. 51B is a cross-sectional view taken at line 51B-51B in FIG. 51A; features in FIGS. 51A and 51B are not necessarily drawn to scale. Although the examples described here are generally in the context of whole blood analysis, the cartridge with dried reagent has utility for other sample types and is not limited to use with whole blood samples.

Planar plastic substrate 2810 and plastic upper housing component 2820 are formed of cyclic olefin polymer (COP), although other plastics (e.g., polystyrene) have been successfully used in the same configuration. Planar plastic substrate 2810 has approximate dimensions of 1 mm×20 mm×75 mm. Cartridge 2830 features a "bulls-eye" inlet port 2835 that has an outer region 2840 adjoining an inner region 2845 that may be D-shaped, as shown. Inner region 2845 may also be shaped differently from the D-shape shown, in particular an O-shape has been successfully demonstrated. Inner region 2845 connects with a fluidic channel 2850, leading to a vent opening 2860. A detection region 2870 forms part of fluidic channel 2850, as shown. In the embodiment shown in FIGS. 51A and 51B, cartridge 2830 is manufactured by aligning substrate 2810 and upper housing component 2820 with an adhesive gasket 2880 that sets height of fluidic channel 2850; in an embodiment, gasket 2880 is approximately 35 µm thick. Once aligned, substrate 2810, upper housing component 2820 and gasket 2880 are pressed together. In alternative embodiments, a plastic substrate and an upper housing component may be laser welded together; in such embodiments one or the other of the substrate and the upper housing component may have a channel feature molded therein to form the fluidic channel.

Part or all of inner surfaces 2812, 2822 of planar plastic substrate 2810 and plastic upper housing component 2820 respectively may be treated with an argon/oxygen plasma to render these surfaces hydrophilic. A hydrophilic surface promotes uniform capillary driven flow in the final assembled cartridge 2830. Experiments have shown that immediately following plasma treatment, a water contact angle of surfaces 2812, 2822 is less than 10 degrees; relaxation in dry air results in a stable contact angle of approximately 30 degrees.

In the embodiment shown in FIGS. 51A and 51B, a liquid reagent is deposited as an array of droplets 2847 on surface 2812; FIGS. 51A and 51B schematically show droplets 2847 immediately after deposition. Size and arrangement of droplets 2847 are controlled such that the spots are close enough to spread and merge before drying, to form a relatively uniform coating, as described below with respect to FIGS. 52A and 52B.

Figure 52A:
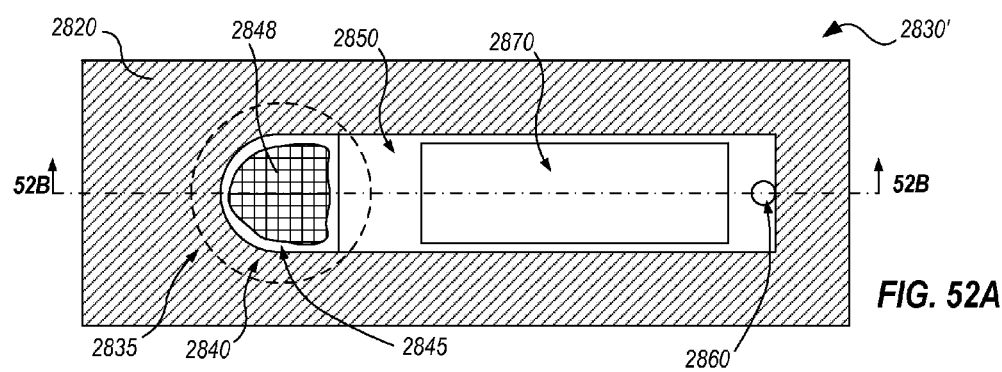
FIGS. 52A and 52B schematically illustrate a cartridge that results from the cartridge of FIGS. 52A and 52B after sufficient time for reagent spots to spread, merge and dry, in an embodiment.
Figure 52B:
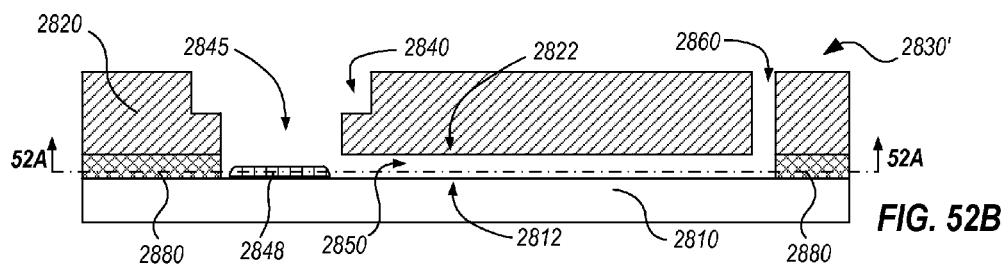

FIGS. 52A and 52B schematically illustrate cartridge 2830' that results from cartridge 2830 after sufficient time for droplets 2847 to spread, merge and dry, forming dried reagent coating 2848. Temperature and humidity control may be balanced such that droplets 2847 have just enough time to spread and merge to form coating 2848 before the reagent completely dries. This is advantageous because the reagent optimally spreads into a uniform coating, but remains within inlet port 2845 for good contact with liquid samples loaded into the inlet port enroute to fluidic channel 2850. It may be advantageous to further process the dried reagent coating by freeze-drying or lyophilization, to promote uniform reagent-sample interactions across the detection region in the fluidic channel.

Figure 53A:
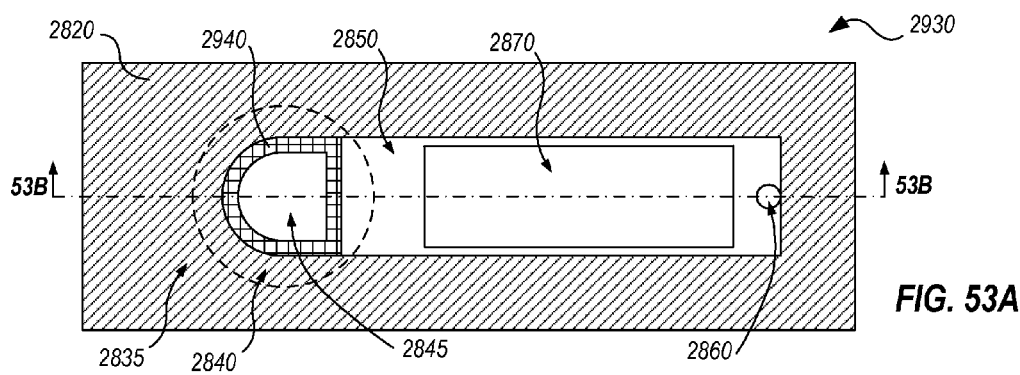
FIGS. 53A and 53B schematically illustrate a cartridge that has a D-shaped dried reagent coating, in an embodiment.
Figure 53B:
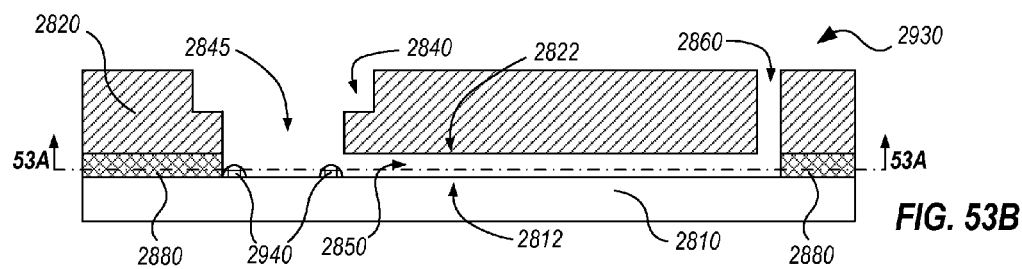
Figure 54A:
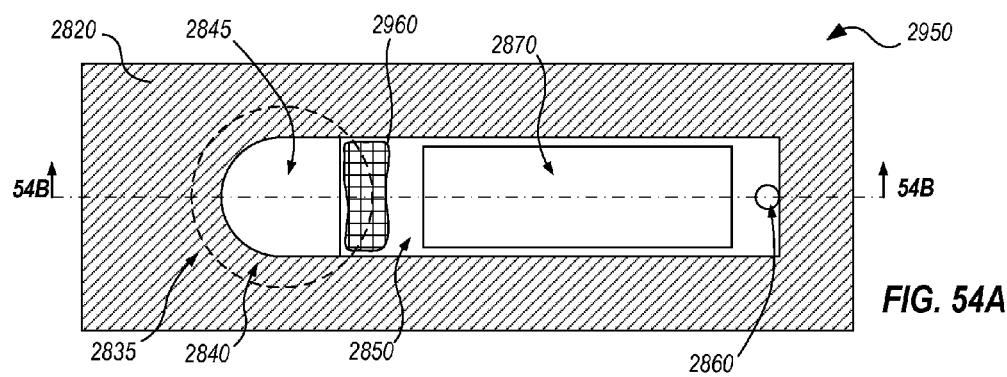
FIGS. 54A and 54B schematically illustrate a cartridge that has a dried reagent coating that is located within a fluidic channel, in an embodiment.
Figure 54B:
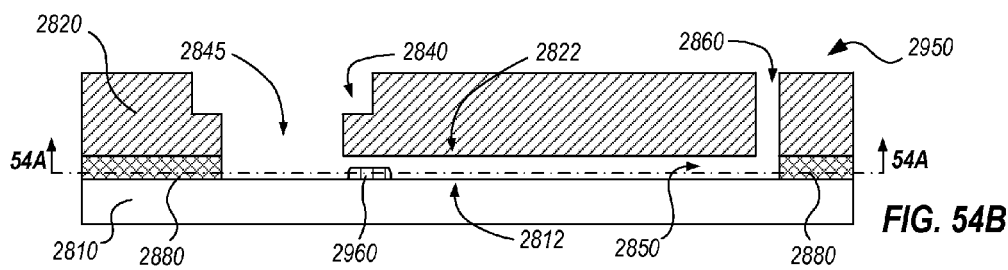

FIGS. 53A and 53B schematically illustrate an alternative cartridge 2930 that has many features common to cartridges 2830, 2830' but has a D-shaped dried reagent coating 2940 that matches the shape of inner region 2845 of inlet port 2835. FIGS. 54A and 54B schematically illustrate an alternative cartridge 2950 that has many features common to cartridges 2830, 2830', 2930 but has a dried reagent coating 2960 that is located within fluidic channel 2850, downstream of inlet port 2835.

Exemplary Performance of Uniform Dried Reagent Placement in Inlet Port

This example provides a demonstration of using engineered dried reagent methods to deliver a useful, single-step assay cartridge that delivers an accurate CD4 T-cell count directly from a small volume of whole blood, e.g., a volume of 10 microliters. A liquid reagent formulation containing 1% sucrose, 0.2% PEG8000, 1% bovine serum albumin (mass/volume %'s), phycoerythrin-labeled anti-CD3 monoclonal antibody (0.4 µg/mL), Alexa647-labeled anti-CD4 monoclonal antibody (0.4 µg/mL), and 25 mM HEPES buffer was prepared. A robotic non-contact micro-dispenser equipped with a pressure driven solenoid valve print head (Biojet, Bio-Dot, Inc.) was used to deposit the liquid reagent formulation into an array of droplets 2847 in a pre-determined pattern on substrates 2810. Individual droplets 2847 were 25 nanoliters in volume, positioned with a center-to-center spacing of 0.5 millimeters in a 62-spot pattern that approximated the D-shaped inlet opening 2845. The microdispenser included a temperature and humidity-controlled enclosure. Deposition of the 62-spot pattern was performed at 21 to 24° C. and 65% relative humidity. The print pattern is conceptually shown in FIG. 51A. At this temperature, humidity, and substrate surface energy, the 25 nanoliter droplets 2847 simultaneously spread while rapidly drying. Droplets 2847 contacted and merged while quickly stopping in an interim "dry" deposition coating 2848 with relative uniformity across the D-geometry, as schematically represented in FIGS. 52A, 52B. Substrates with the 62-spot printed array were processed in a 9 hour lyophilization protocol using a SP Scientific Virtis Vantage Plus EL lyophilizer. After lyophilization, the substrates were aligned with custom tooling and bonded together with a gasket 2880 approximately 35 micrometers thick. Gasket 2880 was manufactured with a cutout that defines a fluidic channel and with two liners that are removed as part of the assembly process. The cartridge components (e.g., substrates 2810 with coatings 2848, gasket 2880 and upper housing component 2820) were assembled using a pneumatic press to form cartridges 2830'. After assembly, cartridges 2830' were packaged in heat sealed barrier pouches until use.

Figure 55:
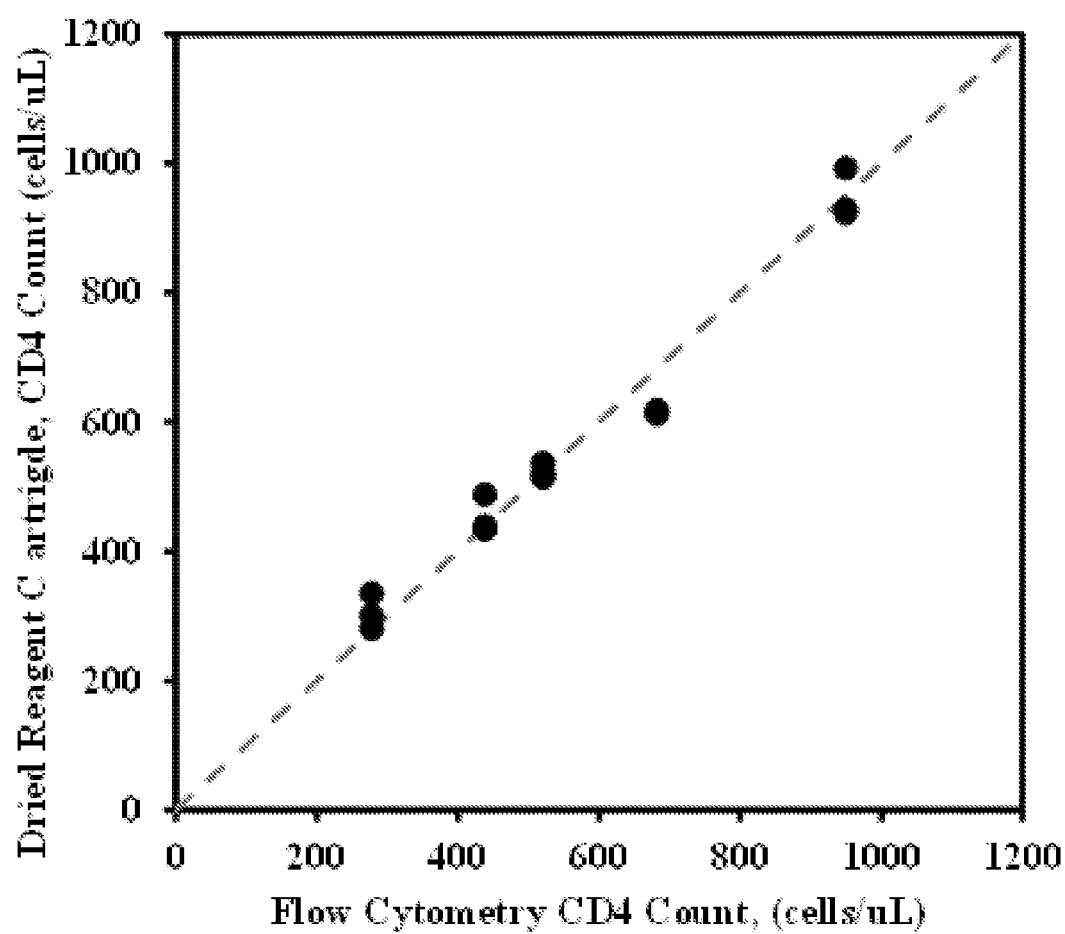
FIG. 55 shows results comparing a CD4 count from assembled cartridges to results obtained from a reference flow cytometer, in an embodiment.

Each assembled cartridge 2830' was placed on a flat surface and approximately 10 microliters of whole blood was added via transfer pipet to inlet port 2840 containing dried reagent coating 2848. This step initiated rehydration of dried reagent 2848. When the blood contacted the entrance to fluidic channel 2850, it was drawn in by capillary forces. Blood-filled cartridges 2830' were allowed to incubate on a bench top at ambient temperature (~21° C.) for 20 minutes. Absolute CD4+ T cell counts were generated using a reader instrument as described above (e.g., system 100', FIG. 8, utilizing imaging and analysis methods such as described above). Results comparing the CD4 count from the assembled cartridges 2830' to results obtained from a reference flow cytometer are provided in FIG. 55. The count accuracy and precision shown in FIG. 55 demonstrate utility of dried reagent cartridge 2830'.

Demonstrations of Uniform and Nonuniform Staining in Dried Reagent Cartridges

In this subsection, descriptions and schematics related to the use of dried reagents integrated in a cartridge are provided. Specifically, schematic representations of uniform and non-uniform sample staining by rehydrated dried reagents are described. A dried reagent coating should be positioned to yield spatially uniform reagent-sample interactions within a detection region of a cartridge. Reagent-sample interactions include for example rehydration of a dried reagent and staining of the sample. Because fluid flow is generally laminar in the cartridges herein, mixing in a width direction of fluidic channels of these cartridges is minimal (e.g., primarily diffusion). Thus, when a dried reagent layer is nonuniform, the resulting sample staining may be non-uniform across the channel width. This phenomenon may be observed by visual analysis of fluorescence images in the detection region. Uniform staining is important because particle counts (e.g., CD4+ T-helper cell counts) may be affected by staining; that is, when a particle identification system (e.g., systems 100, 100') counts particles and in particular counts particles in multiple measurement fields, the statistical validity of the counts and variation among the counts per measurement field will be adversely affected if staining is nonuniform.

When dried reagent deposition is spatially uniform and rehydration rates have been properly designed into a lyophilization formulation, a liquid sample will stain uniformly throughout a detection region. Uniform staining was observed, for example, in the example discussed above. Fluorescence images in the detection region were analyzed and uniform staining was confirmed by visual analysis of sets of digital images, and count accuracy, illustrated in FIG. 55, matched results obtained by flow cytometry.

Figure 56A:
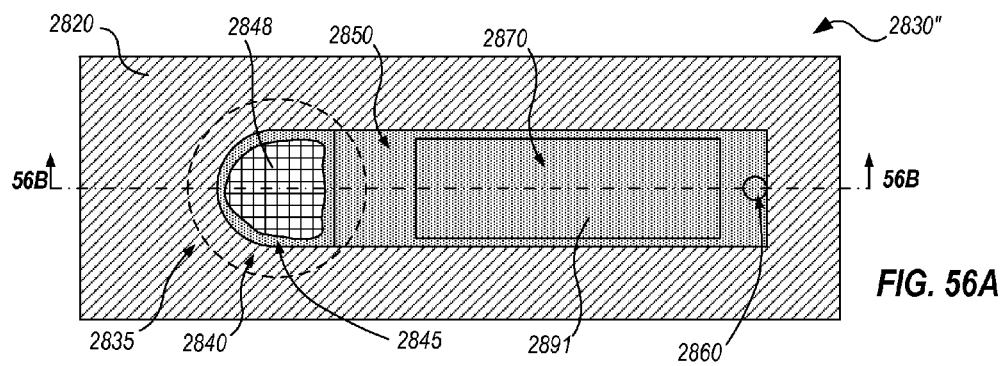
FIGS. 56A and 56B schematically illustrate the cartridge of FIGS. 54A and 54B after addition of a blood sample.
Figure 56B:
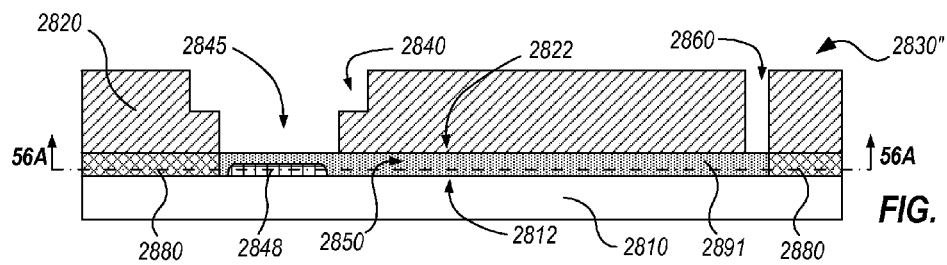

FIGS. 56A and 56B schematically illustrate cartridge 2830" that represents cartridge 2830 after addition of a blood sample. In FIGS. 56A and 56B, fluidic channel 2850 and detection region 2870 therein are shown containing a sample 2891 that is uniformly stained.

Figure 57A:
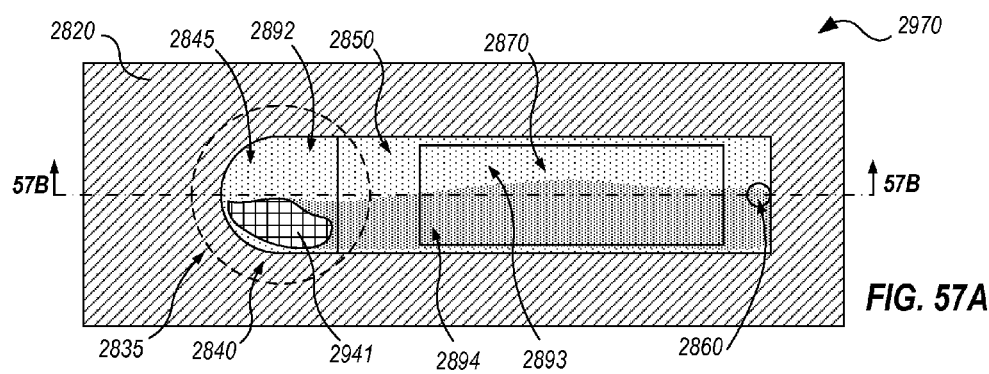
FIGS. 57A and 57B schematically illustrate a cartridge having a dried reagent region that is poorly formed.
Figure 57B:
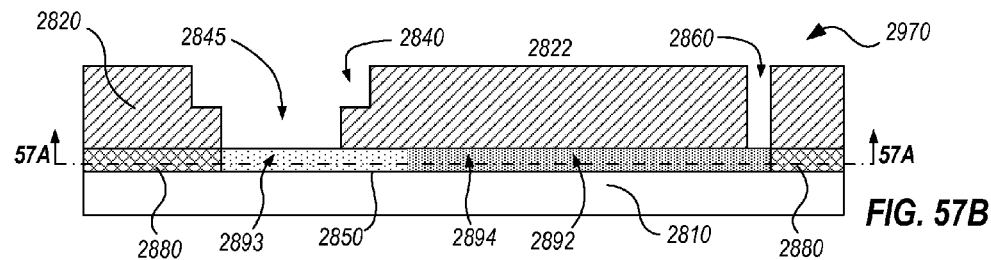

FIGS. 57A and 57B schematically illustrate a cartridge 2970 after addition of a blood sample 2892. Cartridge 2970 includes the same plastic and gasket parts as cartridges 2830, 2830' and 2830" but includes a dried reagent region 2941 that is poorly formed, and covers only one side of inner region 2845 of inlet port 2835, as shown. Consequently, in FIGS. 57A and 57B, fluidic channel 2850 including detection region 2870 are shown as containing a sample that is nonuniformly stained; region 2893 of the sample has a much smaller amount of reagent than region 2894. This undesirable effect, and similar effects described in connection with FIGS. 58A, 58B, 59A and 59B, may be detectable by the techniques in the Cartridge Instrument/Control subsection below, described in connection with FIGS. 64-66. A similar effect may result from a dried reagent layer that, although spanning the inlet port opening, is non-uniform in thickness.

Figure 58A:
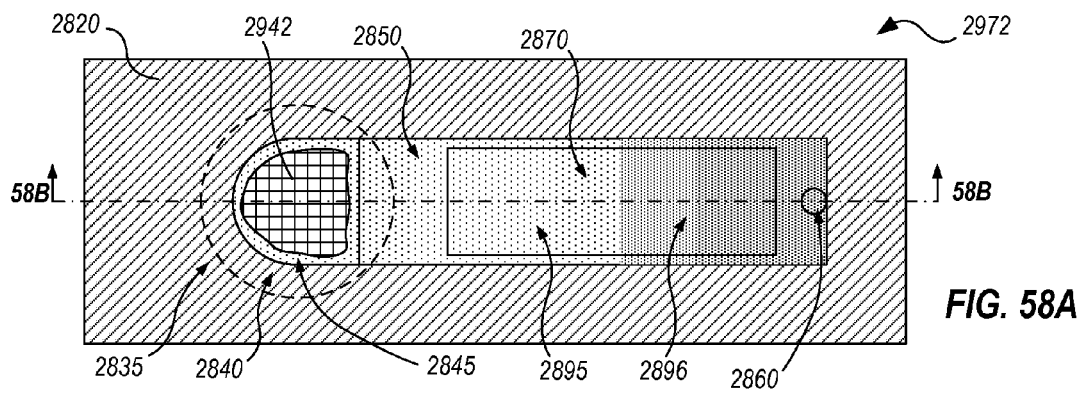
FIGS. 58A and 58B schematically illustrate a cartridge in which reagent rehydration is too rapid with respect to fluid flow, or the cartridge does not contain enough dried reagent.
Figure 58B:
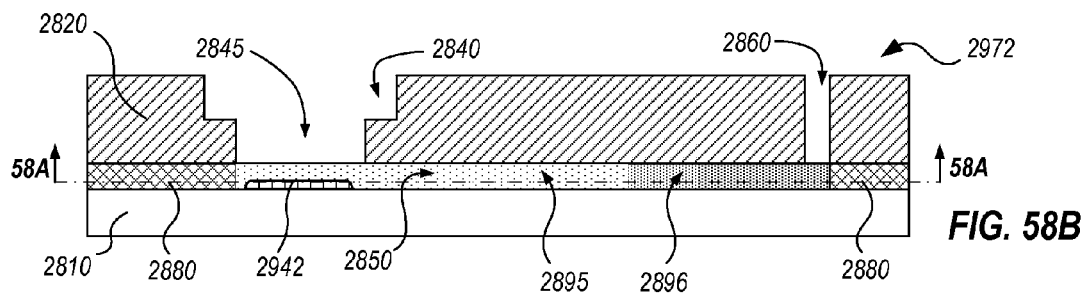

FIGS. 58A and 58B schematically illustrate a cartridge 2972 after addition of a blood sample. Cartridge 2972 includes the same plastic and gasket parts as cartridges 2830, 2830' and 2830" but includes a dried reagent region 2942 in which reagent rehydration is too rapid with respect to fluid flow, or does not contain enough dried reagent. Rapid rehydration leads to complete dissolution of reagent into a leading edge of the liquid sample. In this case, the trailing volume does not get properly stained. The result is non-uniform staining down the length of fluidic channel 2850. Consequently, in FIGS. 58A and 58B, fluidic channel 2850 including detection region 2870 are shown as containing a sample that is nonuniformly stained; region 2895 of the sample has a smaller amount of reagent than region 2896. In embodiments, rehydration rate may be slowed by additives such as sugars.

Figure 59A:
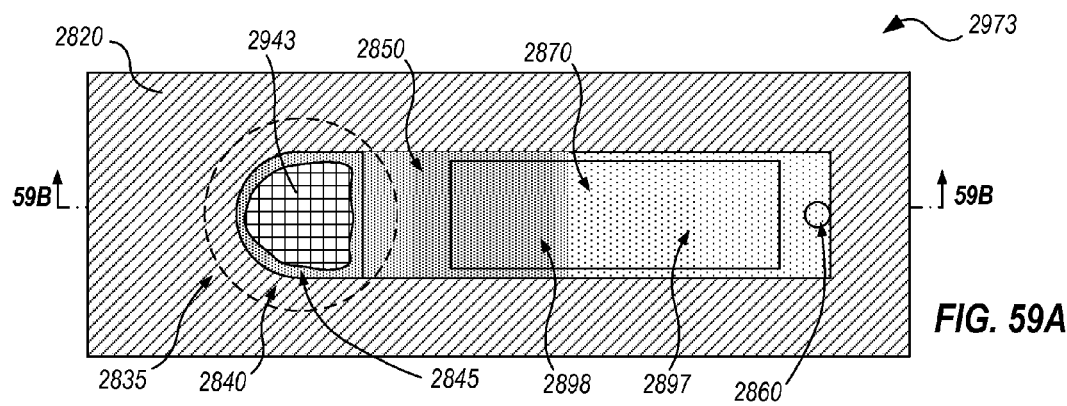
FIGS. 59A and 59B schematically illustrate a cartridge after addition of a blood sample in which reagent rehydration is too slow with respect to fluid flow.
Figure 59B:
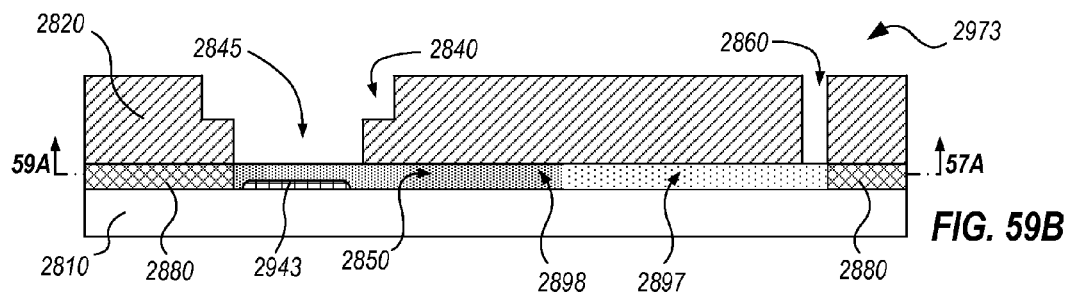

FIGS. 59A and 59B schematically illustrate a cartridge 2973 after addition of a blood sample. Cartridge 2973 includes the same plastic and gasket parts as cartridges 2830, 2830' and 2830" but includes a dried reagent region 2943 in which reagent rehydration is too slow with respect to fluid flow. Rapid rehydration leads to complete dissolution of reagent into a leading edge of the liquid sample. In this case, the leading edge of liquid sample moves into the fluidic channel without picking up stain. Again, the result is non-uniform staining down the length of fluidic channel 2850. Consequently, in FIGS. 59A and 59B, fluidic channel 2850 including detection region 2870 are shown as containing a sample that is nonuniformly stained; region 2897 of the sample has a smaller amount of reagent than region 2898.

Sample Hold and Release Cartridge

In this subsection, cartridge features and methods of their use for selectively holding and releasing fluid flow in a cartridge are disclosed. Such features are useful because they facilitate control of incubation time of a sample within a cartridge, for example to control rehydration of a reagent and/or exposure of the sample to a reagent. That is, holding a liquid sample in the inlet port may be advantageous in certain applications in which a reagent dissolution step is required. The hold time can be selected for optimum dissolution/rehydration. One way to provide such control is to provide a frangible surface connected with a fluidic path such that before the surface is broken, air trapped in the fluidic path stops the advancement of fluid, but after the surface is broken, the air may escape such that capillary forces can draw the fluid towards the broken surface. Upon addition of a liquid sample, the liquid "seals" the slot-shaped entrance to the fluidic channel and there is no path for the air in the channel to escape. As a result, the sample sits in the inlet port without substantively entering the fluidic channel.

Figure 60A:
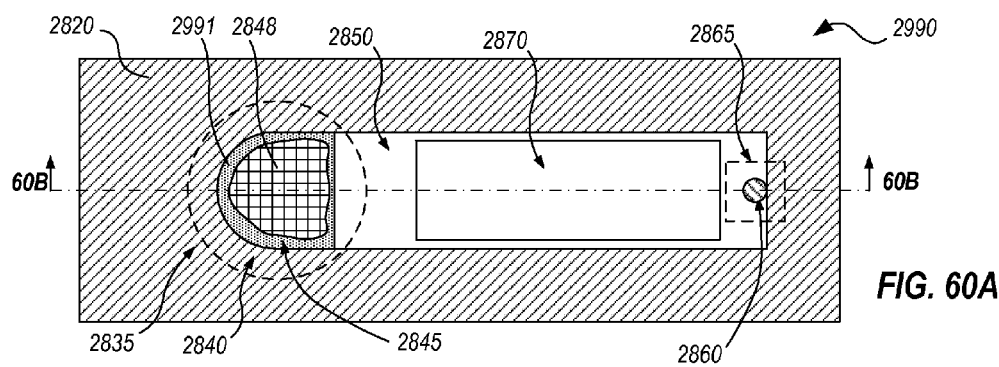
FIGS. 60A and 60B are schematic representations of a liquid sample being held in an inlet port of a cartridge, in an embodiment.
Figure 60B:
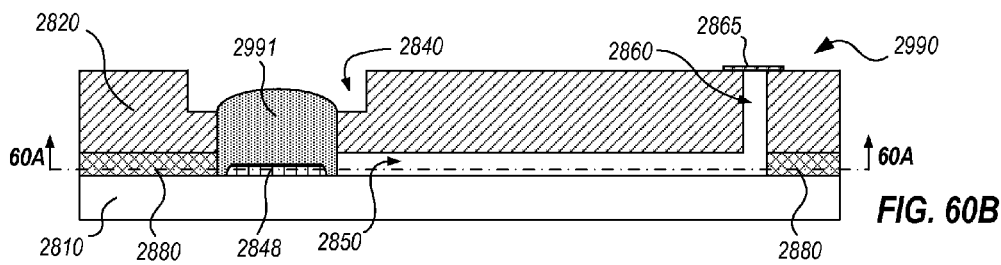
Figure 61A:
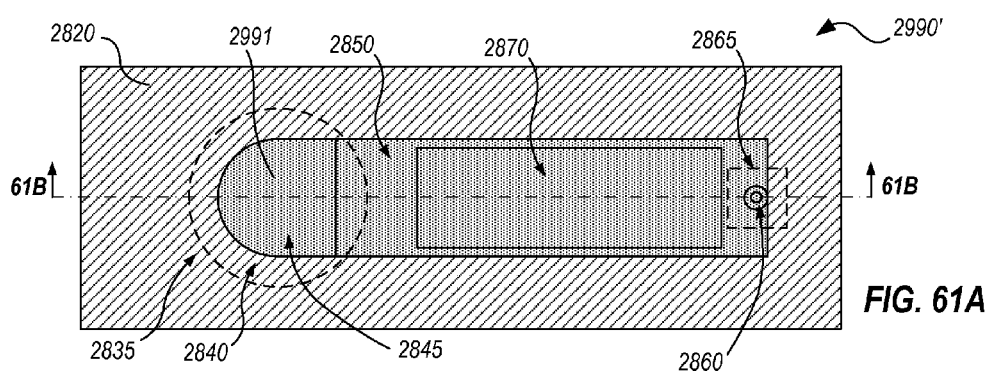
FIGS. 61A and 61B show the liquid sample being drawn into a fluidic channel of the cartridge of FIGS. 60A and 60B, in an embodiment.
Figure 61B:
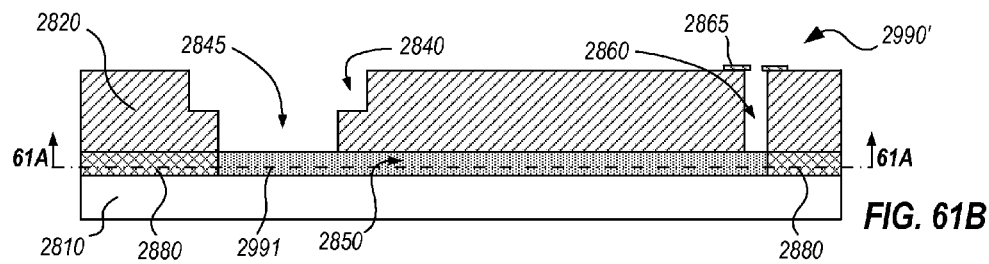

FIGS. 60A and 60B are schematic representations of a liquid sample 2991 being held in inlet port 2835 of a cartridge 2990. Cartridge 2990 includes the same plastic and gasket parts as cartridges 2830, 2830' and 2830" but includes a frangible seal 2865 covering vent 2860. Frangible seal 2865 may be for example an adhesive vent cover. After a user-determined time, frangible seal 2865 is punctured. Capillary forces draw liquid sample 2991 into fluidic channel 2850, as shown in cartridge 2990', FIGS. 61A and 61B. Displaced air escapes through vent 2860.

Figure 62A:
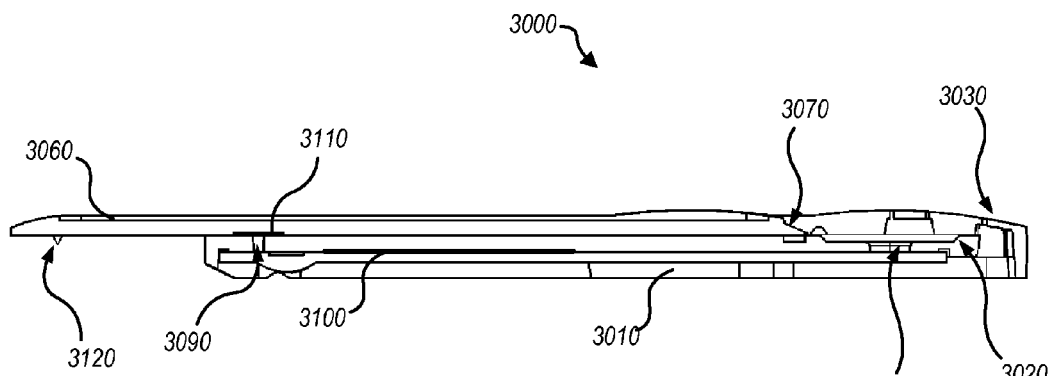
FIGS. 62A and 62B are cross-sectional illustrations showing a cartridge that has features to hold and release a liquid sample into a fluidic channel, in an embodiment.
Figure 62B:
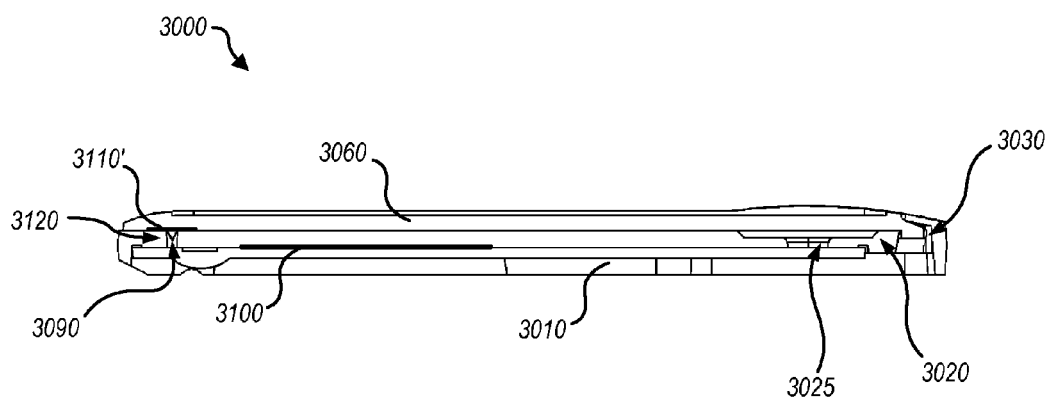

FIGS. 62A and 62B are cross-sectional illustrations showing a cartridge 3000 that has features to hold and release a liquid sample into a fluidic channel. Cartridge 3000 includes a cartridge body 3010 and a cartridge lid 3060. FIG. 62A shows lid 3060 in a first, open position relative to body 3010, while FIG. 62B shows lid 3060 in a second, closed position. Lid 3060 slides within a channel formed by body 3010. Lid 3060 includes a flange 3070 at a leading edge thereof, that is adapted for capture by a capture feature 3030 of cartridge body 3010, as discussed above in connection with FIGS. 45-48.

When lid 3060 is in the open position shown in FIG. 62A, an inlet port 3020 is exposed. Inlet port 3020 has a volume capacity that is greater than the volume of whole blood required for proper operation of cartridge 3000 in systems 100, 100'. Inlet port 3020, and other features of cartridge 3000 that are exposed to a sample, are treated (e.g., with plasma) to make them hydrophilic. Inner region 3025 of inlet port 3020 connects with a fluidic channel 3100 that extends down the length of the cartridge, providing multiple fields of view for imaging thereof. Fluidic channel 3100 connects with a vent 3090 that is covered with an unbroken frangible seal 3110 in FIG. 62A. Lid 3060 includes a protrusion 3120 on an underside thereof, which breaks frangible seal 3110 when lid 3060 is moved to a closed position, as discussed below.

The hydrophilic surfaces of inlet port 3020 generate a capillary force that enables acquisition of a sample by simply inverting cartridge 3000 and placing inlet port 3020 onto a blood droplet on an upturned finger. Alternatively, the blood droplet can contact cartridge inlet port 3020 while the cartridge is on a surface such as a table top. Alternatively, the sample can be transferred into port 3020 using a transfer device such as a transfer pipette or other dedicated device (e.g., DIFF-SAFE® blood tube adapter). If trapped air within fluidic channel 3100 did not stop the sample, the hydrophilic surfaces and small surface geometry of fluidic channel 3100 will continue to draw the sample through fluidic channel 3100. However, in the lid position shown in FIG. 62A, the back pressure of trapped air within fluidic channel 3100, blocked by frangible seal 3110, keeps the sample from proceeding down fluidic channel 3100.

After a sample is loaded into inlet port 3020 while cartridge 3000 has lid 3060 in the first or open position shown in FIG. 62A, lid 3060 can be moved to the second or closed position shown in FIG. 62B. In closing lid 3060, the features of cartridge 3000 cooperate to produce several useful outcomes: (1) Lid 3060 covers inlet port 3020, sealing the sample within cartridge 3000 for safety purposes, since the sample may be biohazardous. (2) Capture feature 3030 captures flange 3070, preventing accidental reopening of cartridge 3000. This is a safety feature and prevents accidental re-use of cartridge 3000, which may lead to unreliable results since the initial sample would have dissolved and mixed with reagents therein. (3) Protrusion 3120 pierces frangible seal 3110, resulting in perforated frangible seal 3110'. Perforated frangible seal 3110' is not airtight and allows air to escape from fluidic channel 3100, so that capillary forces draw the sample from inlet port 3020 into fluidic channel 3100. This positions the sample over a detection region (not labeled in FIGS. 62A and 62B) for imaging and particle counting, as described above.

Exemplary Performance of Sample Hold and Release Cartridge

Figure 63:
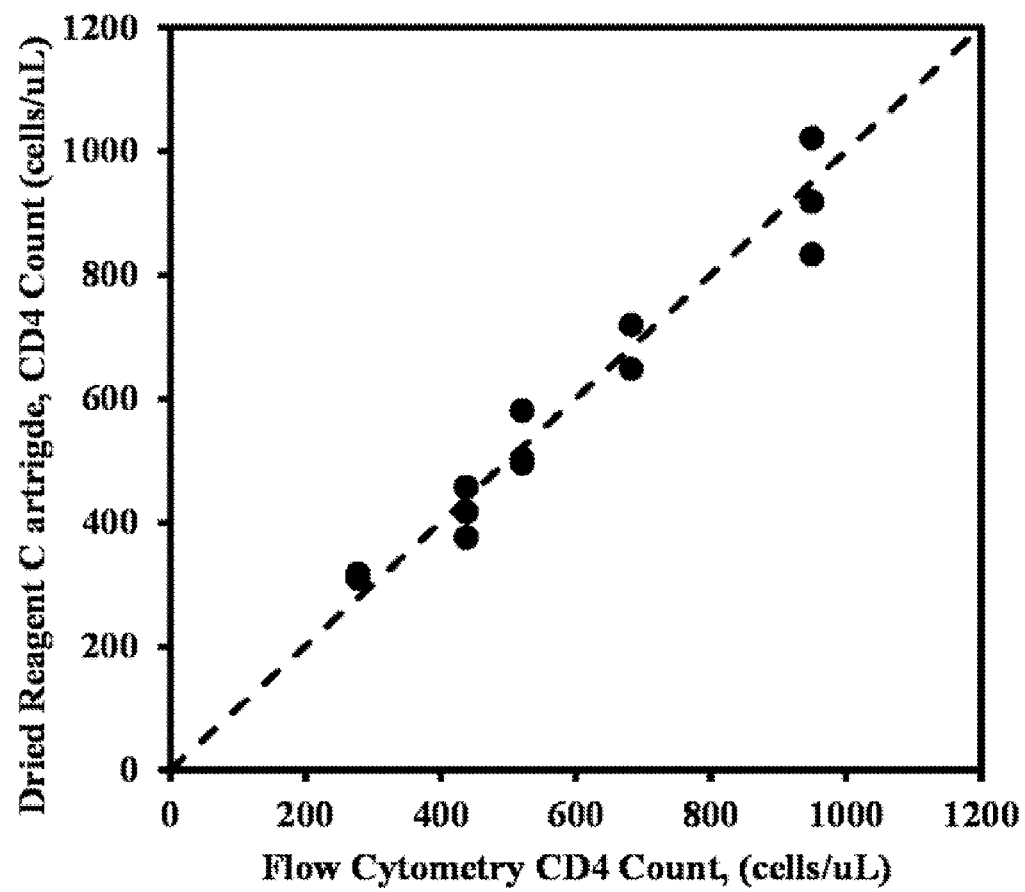
FIG. 63 shows results comparing a CD4 count from assembled cartridges having features to hold and release a liquid sample into a fluidic channel, to results obtained from a reference flow cytometer, in an embodiment.

Cartridges 2990 with integrated dried reagents were prepared and assembled as described in connection with FIGS. 60A, 60B above. Prior to performing an assay with the cartridge, each vent hole 2860 was sealed with adhesive tape (Nunc Aluminum Seal Tape), forming a frangible seal 2865. By covering vent hole 2860, the fluidic channel became a closed end, effectively hermetically sealed chamber. In this specific example, a 10 microliter whole blood sample was added to each inlet port 2835 using a transfer pipet. The blood samples sat in inlet ports 2835 without entering fluidic channels 2850. After a ten second hold, each vent 2860 was opened by manually puncturing each respective frangible seal 2865. Immediately upon puncturing frangible seal 2865, blood flowed into each respective fluidic channel 2850. The resulting blood-filled cartridges 2990' were then allowed to incubate on the bench top at ambient temperature (~21° C.) for 20 minutes. Absolute CD4+ T cell counts were generated using the reader instrument described in the present invention. Results comparing the CD4 count from cartridges 2990' to results obtained from a reference flow cytometer are provided in FIG. 63. The achieved count accuracy and precision demonstrate utility of cartridges 2990, 2990'. Cartridge 3000 implements similar features to those of cartridges 2990, 2990' to simplify sample collection and processing in a clinical environment (e.g., by facilitating sample collection, integrating protrusion 3120 for piercing frangible seal 3110 into the cartridge lid, and facilitating sealing of the cartridge simply by closing lid 3060 with respect to cartridge body 3010).

Cartridge/Instrument Control Features

In many applications, it is desirable to incorporate system features that ensure proper operation of an assay protocol, cartridge, and instrumentation. In this subsection, various embodiments associated with system quality controls are described.

The embodiments described here are based on a cartridge (e.g., one of cartridges 130, 130', 2500, 2600, 2600') that incorporates one or more fluidic channels that serve as sample chambers with detection regions. By incorporating inlet and outlet ports, the fluidic channels facilitate performing sequential fluidic assay steps. In many instances, it is desirable to know if a fluidic channel has sufficient liquid volume for performing a particular assay operation.

Detection of a liquid in a certain region, such as the detection region in a cartridge, may rely on for example, electrical or optical methods. Presence of a fluid may be detected optically by relying on properties of the fluid that differ from properties of a material replaced by the fluid, such as air or another liquid or fluid. If the fluid is more or less absorptive at least at a certain wavelength, its presence may be detected by an absorption measurement. If the fluid contains fluorescent material, its presence may be detected by performing a fluorescence measurement. Thus, sample addition, rehydration of dried reagents and proper staining of the sample by the reagents may all be considered control features for evaluating assay validity. These features are viewable by an imager within one or more measurement fields of a cartridge.

In an embodiment, a fluorescence measurement is performed to read out the results of an assay such as a fluorescent immunoassay or a fluorescent immunostaining assay. The assay itself may involve incubating a sample with fluorescent material prior to the sample entering a detection region of a cartridge. Presence of the sample may be detected by detecting the fluorescent material utilizing the same fluorescence measurement system that is used for the assay. This method has the benefit that it will detect the presence of a required assay reagent and may be configured to determine a value indicative of the amount of fluorescent material present in the detection region. This value may be used for calibration purposes. In cases where it is possible for the fluorescent material to populate the region without actual sample addition, this method may be utilized exclusively for detecting presence, and optionally, an amount of fluorescent material present.

It is also possible to deduce sample presence from detecting properties of an assay requiring the presence of both sample and assay reagents. In an embodiment, a cartridge is used to measure certain analytes. Successful detection of at least some of these analytes may be used as a measure of sample presence, as well as presence of assay reagents and validity of the assay. The detection scheme utilized may be the same as that used to read out actual assay results. In another embodiment, the presence of sample, and optionally the presence of reagents as well as assay validity, may be deduced from data recorded to determine the assay results, with no need to perform measurements in addition to those being done to perform the assay.

Analytical methods are, for example, used to detect one or more changes in parameters, that can indicate incomplete liquid fill of a fluidic channel or sample chamber. In one embodiment, a cartridge and reader system are used to identify and/or count a certain particle type within a sample. By counting the particles in discrete locations (e.g., measurement fields) in a fluidic channel, count statistics can be used to identify changes indicative of incomplete channel fill. For example, a sudden change in particle count that exceeds a predetermined amount (e.g., empirically derived) may indicate incomplete channel fill. In another embodiment, a large percent coefficient of variation (% CV, defined as the ratio of sample standard deviation to the mean, expressed as %) for a series of measurement fields across a fluidic channel may indicate incomplete liquid fill. Therefore, in an embodiment, count % CV across a fluidic channel is compared to a Poisson-limited % CV. A count % CV that exceeds the Poisson-limited % CV by a given amount can be interpreted as an incomplete channel fill. A demonstration of this embodiment is now provided.

Example: Presence of Sample and Detection Reagent in Cartridge Evaluated Through Image Analysis Tests were performed on a system that included a cartridge configured for detection of T-helper cells in a whole blood sample, and an instrument for identification and counting of the T-helper cells in the cartridge through fluorescence imaging. The cartridge included a fluidic channel with a detection region, such as the cartridges described herein. A blood sample was provided; before the blood sample entered the detection region, the sample was mixed with an immunostain including anti-CD3 antibodies labeled with Phycoerythrin (PE) and anti-CD4 antibodies labeled with Alexa647 (A647). The instrument recorded PE fluorescence images and A647 fluorescence images of twelve measurement fields along the fluidic channel. The images were analyzed using parts or all of the software routine described in FIGS. 13 through 30B. The instrument also calculated average fluorescence signal in images obtained under illumination from each of two illumination sources (e.g., illumination sources 200, 300, FIG. 2) and a number of T-helper cells identified from the images. T-helper cells have CD3 and CD4 receptors, and therefore produce signal under illumination from each of the two illumination sources.

Figure 64:
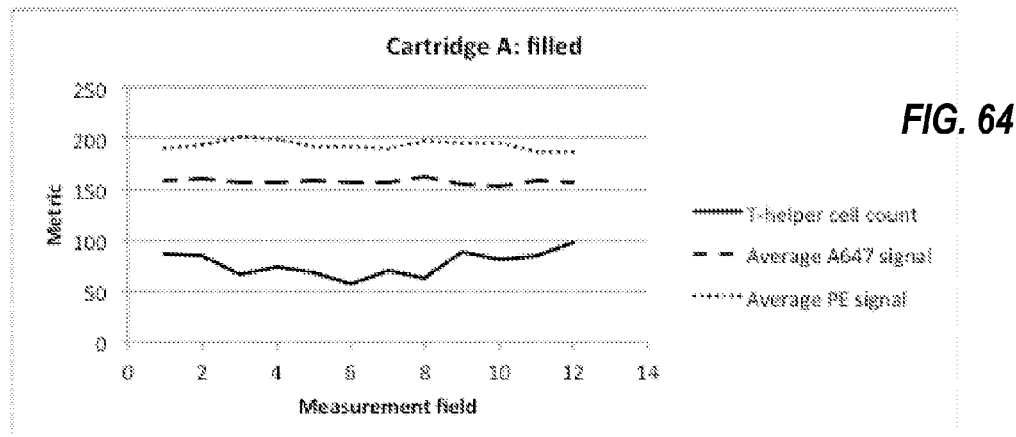
FIGS. 64, 65 and 66 show average signal recorded in both fluorescence channels, as well as the number of T-helper cells for each measurement field, for each of three cartridges, in an embodiment.
Figure 65:
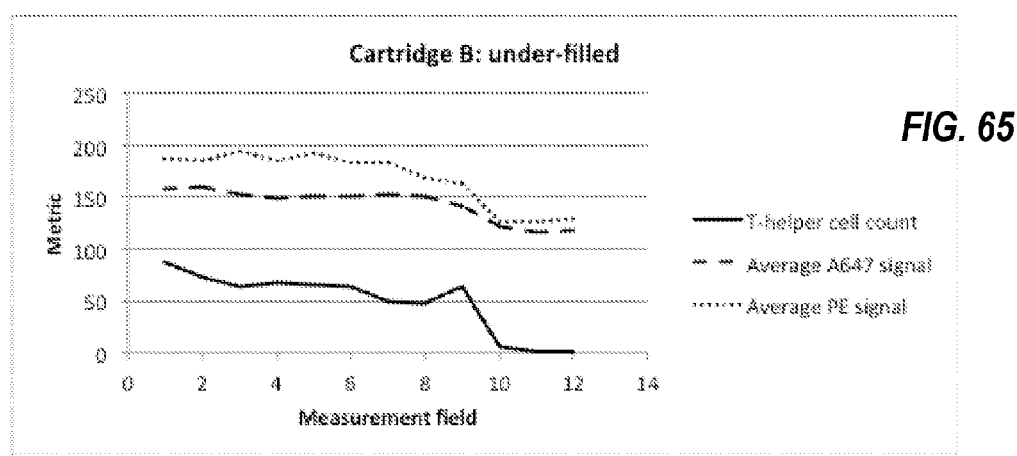
Figure 66:
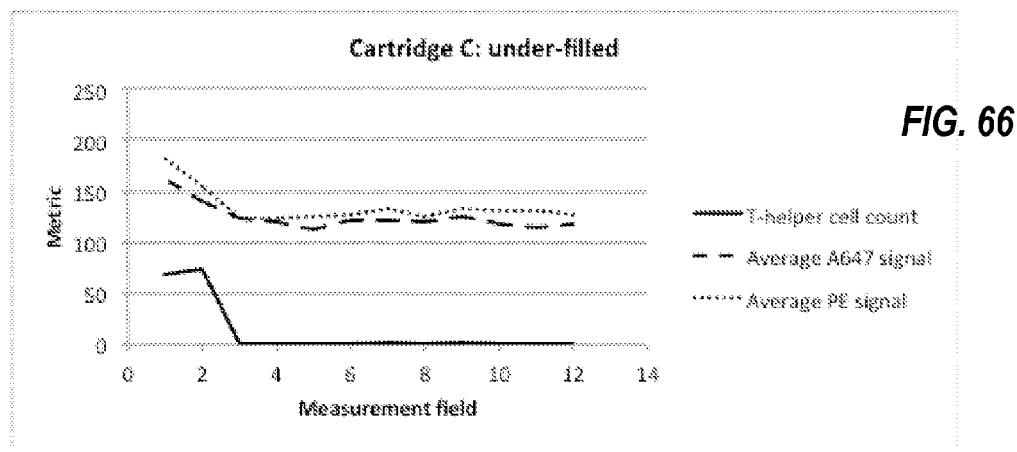

These tests demonstrated the use of image analysis to determine that sufficient sample and/or detection reagent was added to a fluidic channel in an assay cartridge. In an experiment, three cartridges were imaged. Cartridge A was known to have a properly filled detection region, whereas cartridges B and C were intentionally under-filled such that some measurement fields contained no sample. FIGS. 64, 65 and 66 show average signal recorded in both fluorescence channels, as well as the number of T-helper cells for each measurement field, for each of the three cartridges (both the T-helper cell counts and the fluorescence channel signals are referred to below as metrics). Measurement fields 1 and 12 were the extreme upstream and downstream measurement fields, respectively, in the detection region of each cartridge. When comparing cartridges A, B, and C, it is clear that cartridge A produced relatively consistent levels for all three metrics, while cartridges B and C exhibited a clear drop in all three metrics at a certain point along the length of the channel. The most distinct drop was exhibited by the T-helper cell count that dropped from a level of 50-100, to a near zero value for both cartridges B and C.

Numerous methods may be used to identify sudden value changes as well as their location. In the present experiment, the presence of a sudden change in the number of T-helper as a function of channel position was identified by calculating the coefficient of variation (% CV) for the T-helper cell count. Cartridges A, B, and C had % CVs of 16%, 61%, and 223%, respectively. For comparison, the Poisson limited % CV is 11%, e.g., the expected % CV for a measurement subject only to counting statistics type errors will average 11%. Clearly, cartridges B and C had abnormally large % CVs, indicating a partially filled channel.

Further analysis was performed in order to determine if the investigation revealed only a single, sudden T-helper cell count drop, or if the large % CVs for cartridges B and/or C were caused by highly variable T-helper cell counts. For measurement fields 2-12, a relative change compared to the preceding measurement field was calculated as [count(i)−count(i−1)]/[count averaged over all measurement fields], where i is the measurement field number. The results are shown in Table 1 below.

tridges B and C showed a relative change smaller than −100 at measurement fields 10 and 3, respectively. It was deduced from these results that the detection region of cartridge A was properly filled while the detection region of cartridges B and C were filled only through measurement fields 9 and 2, respectively.

A similar method may be applied to the average PE signal to determine a cartridge underfill condition. In the case of the PE signal, a criterion that can be used to determine underfill is a −12% relative change in PE signal from one measurement field to the next.

Another embodiment of the cartridge is provided describing a device (e.g., cartridge) for analyzing an analyte in a sample. The device may include at least a first substrate, a second substrate, a fluidic channel, an inlet port, and an outlet port. In one aspect, the first substrate and said second substrate each has an inner surface and an outer surface. The inner surface of the first substrate may form, at least in part, the lower wall of the fluidic channel, while the inner surface of the second substrate may form, at least in part, the upper wall of the fluidic channel. In another aspect, the fluidic channel is connected to both the inlet port and the outlet port. In another aspect, the fluidic channel includes at least a reagent region and a detection region, and at least a portion of the reagent region is coated with one or more dried reagents, which contain at least a detection molecule that binds the analyte in the sample. In another aspect, the device also contains a wicking pad located on the outer surface of the second substrate, and the wicking pad is positioned at a pre-determined distance from the outlet port. In another aspect, the reagent region is located between the inlet port and the detection region, such that the sample, when added to the inlet port, passes through the reagent region before entering the detection region. In another aspect, the analyte bound with the detection molecule may be detected in the detection region.

In another aspect, the one or more dried reagents may form a spatially uniform layer at the reagent region. In another aspect, the dried reagent coating may be distributed evenly along the width of the fluidic channel that is perpendicular to the sample flow path from the inlet port to the

TABLE 1

Relative count change and average PE signal change, compared to previous measurement field, for T-helper cells counted in cartridges A, B and C

| Measurement field | Relative change in T-helper cell count | | | Relative change in average PE signal | | |
|---|---|---|---|---|---|---|
| | Cartridge A | Cartridge B | Cartridge C | Cartridge A | Cartridge B | Cartridge C |
| 1 | | | | | | |
| 2 | −4% | −31% | 10% | 2% | −2% | −16% |
| 3 | −37% | −20% | −151% | −5% | 6% | −18% |
| 4 | 14% | 8% | 0% | 0% | −5% | 0% |
| 5 | −12% | −4% | 0% | −1% | 3% | 1% |
| 6 | −22% | −4% | 2% | 4% | −5% | 1% |
| 7 | 27% | −27% | 2% | 0% | 0% | 4% |
| 8 | −14% | −6% | −4% | −1% | −8% | −4% |
| 9 | 53% | 35% | 4% | −4% | −3% | 4% |
| 10 | −14% | −121% | −2% | −2% | −22% | −1% |
| 11 | 6% | −8% | −2% | 5% | 0% | 1% |
| 12 | 27% | 0% | 0% | 2% | 2% | −2% |

Since an empty measurement field is expected to lead to a near-zero count, a partially filled channel was diagnosed by relative changes smaller than −100% and/or greater than +100%. Cartridge A showed no such changes, while caroutlet port. This uniform layer may be formed by depositing liquid reagents onto the reagent region forming a plurality of single spots, and by allowing the plurality of single spots to merge before the liquid in each single spot evaporates. In another aspect, each of the single spots may receive from 1 to 50 nanoliters of liquid reagents, and the center-to-center spacing of the single spots and the volume deposited to each spot are collectively controlled to ensure that droplet-to-droplet contact occurs following deposition. In another aspect, the dried reagent coating may have a rehydration rate and physical dimension that collectively yield spatially uniform reagent-sample interaction within the detection region. The rehydration rate of the dried reagent coating may be determined by the reagent formulation and the composition of the sample. In another aspect, the dried reagent may contain an additive, such as sucrose, that slows the rehydration rate of the dried reagent coating.

In another aspect, the inlet port may have a volume greater than the volume of the fluidic channel, which may generate capillary action that facilitates movement of the sample from the inlet port to the fluidic channel. In another aspect, the walls of the inlet port, the walls of the fluidic channel, or both may be coated, either entirely or in part, with a hydrophilic layer. In another aspect, the walls of the inlet port and the walls of the fluidic channel may be rendered hydrophilic by its building material, by the coating of the hydrophilic layer, or by other treatment of the building material such as plasma treatment, so that they have a water contact angle of less than 50 degrees, less than 40 degrees, less than 30 degrees, or less than 10 degrees.

In another aspect, the cartridge may have an internal tilt relative to a level orientation, which is sufficient to drive flow of the liquid sample from the inlet port to the outlet port. In another aspect, one, two, and/or three of the factors, namely, the tilt, the capillary action, and the wicking pad, may contribute to driving the flow of the liquid sample from the inlet port to the outlet port. In another aspect, the tilt is at an angle between 2 and 45 degrees relative to a level orientation.

In another aspect, the distance between the wicking pad and the outlet port is sufficient to prevent the wicking pad from draining the fluidic channel. In another aspect, the wicking pad is made of a material having a wicking rate of between 10 and 200 seconds per 4 centimeters (cm) of the material. In another aspect, the wicking pad is made of a material having a certain absorbance rate, wherein the surface tension of the liquid sample emerging from the outlet port breaks the fluidic connection between the wicking pad and the outlet port when the absorbance rate exceeds the rate at which the liquid sample emerges from the outlet port, thereby preventing further fluidic flow from the outlet port to the wicking pad. In another aspect, the distance between the wicking pad and the outlet port is between 1 and 5 mm.

In another aspect, the detection region includes a plurality of capture molecules bound to the inner surface of the first substrate. In another aspect, the plurality of capture molecules are arranged as an array including at least two reaction sites, each of the at least two reaction sites being formed by depositing a composition onto the inner surface of the first substrate, wherein the composition contains at least one of the capture molecules. In another aspect, binding of the dried reagent to the analyte in the sample does not prevent binding of the same analyte to the plurality of capture molecules. Details of the capture molecules and the array may be found in U.S. patent application Ser. No. 13/233,794 as filed on Sep. 15, 2011, which is incorporated herein by reference in its entirety.

The changes described above, and others, may be made in the particle identification systems, cartridges and methods described herein without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A device for analyzing an analyte in a liquid sample, said device comprising,
   a first substrate,
   a second substrate,
   a fluidic channel,
   an inlet port through the second substrate, and
   an outlet port through the second substrate,
   wherein said first substrate and said second substrate each has an inner surface and an outer surface, the inner surface of the first substrate forming, at least in part, a lower wall of said fluidic channel, the inner surface of said second substrate forming, at least in part, an upper wall of said fluidic channel, said fluidic channel being connected to said inlet port and said outlet port,
   wherein said fluidic channel comprises a reagent region and a detection region, at least a portion of the reagent region having a coating with one or more dried reagents,
   wherein the outlet port forms a capillary valve having burst pressure exceeded when the device is oriented at a tilt relative to a level orientation, to break the capillary valve and drive flow of said liquid sample from the inlet port to the outlet port, and
   wherein said device further comprises a wicking pad configured to absorb excess liquid sample emerging from the outlet port, the wicking pad being characterized by an absorbance rate and being located on the outer surface of said second substrate at a distance from said outlet port, the absorbance rate and the distance cooperating to prevent draining the fluidic channel into the wicking pad, the outlet port and the outer surface of said second substrate between the outlet port and the wicking pad being characterized by surface tension forces that cooperate with the distance to break fluidic connection between the wicking pad and the outlet port when rate at which the liquid sample emerges from the outlet port is less than the absorbance rate, thereby preventing further fluidic flow from the outlet port to the wicking pad.

2. The device of claim 1, wherein the reagent region is located between the inlet port and the detection region, such that the liquid sample, when added to the inlet port, passes through the reagent region before entering the detection region.

3. The device of claim 1, wherein the one or more dried reagents comprise a detection molecule that binds to the analyte in the liquid sample.

4. The device of claim 3, wherein the coating is formulated to release the detection molecule into the liquid sample for detection of the analyte bound with the detection molecule in the detection region.

5. The device of claim 1, wherein the one or more dried reagents form a single spatially uniform, continuous layer at the reagent region.

6. The device of claim 1, wherein the coating with one or more dried reagents is distributed evenly along the width of the fluidic channel that is perpendicular to a sample flow path from the inlet port to the outlet port.

7. The device of claim 5, wherein the single spatially uniform, continuous layer is formed by depositing liquid reagents onto the reagent region forming a plurality of single spots, wherein the plurality of single spots merge before the liquid in each single spot evaporates thereby forming the single spatially uniform, continuous layer of dried reagents.

8. The device of claim 7, wherein each of the single spots receives 1-50 nanoliters of liquid reagents in volume, wherein the center-to-center spacing of the single spots and the volume deposited to each spot collectively ensure droplet-to-droplet contact following deposition.

9. The device of claim 1, wherein the coating with one or more dried reagents has a rehydration rate and physical dimension that collectively yield spatially uniform reagent-sample interaction within the detection region.

10. The device of claim 1, wherein rehydration rate of the one or more dried reagents is determined by reagent formulation of the coating and composition of the liquid sample.

11. The device of claim 10, wherein the one or more dried reagents comprise an additive that slows the rehydration rate of the coating with one or more dried reagents.

12. The device of claim 11, wherein the additive is sucrose.

13. The device of claim 1, wherein the coating with one or more dried reagents comprises sucrose, polyethylene glycol, and a dye-labeled antibody.

14. The device of claim 1, wherein the inlet port has a volume greater than the volume of the fluidic channel.

15. The device of claim 1, wherein walls of the inlet port and walls of the fluidic channel are coated, at least in part, with a hydrophilic layer.

16. The device of claim 15, wherein the walls of the inlet port and the walls of the fluidic channel are hydrophilic having a water contact angle of less than 50 degrees.

17. The device of claim 1, further comprising a lid that irreversibly closes over the inlet port.

18. The device of claim 1, wherein said tilt is at an angle between 2 and 45 degrees relative to a level orientation.

19. The device of claim 1, the absorbance rate being between 10 and 200 seconds per 4 centimeters (cm).

20. The device of claim 1, wherein said distance between the wicking pad and the outlet port is between 1 and 5 mm.

21. The device of claim 1, wherein the detection region comprises a plurality of capture molecules bound to the inner surface of the first substrate.

22. The device of claim 1, wherein a plurality of capture molecules are arranged as an array including at least two reaction sites, each of the at least two reaction sites being formed by depositing a composition onto the inner surface of the first substrate, said composition comprising at least one of the capture molecules.

23. The device of claim 1, the outer surface of the second substrate comprising rails for creating capillary forces to steer, from the outlet port to the wicking pad, a portion of the liquid sample located on the outer surface of the second substrate.

* * * * *